(12) United States Patent
Cha et al.

(10) Patent No.: US 11,563,181 B2
(45) Date of Patent: *Jan. 24, 2023

(54) AMINE COMPOUNDS FOR ORGANIC LIGHT-EMITTING DIODE AND ORGANIC LIGHT-EMITTING DIODE INCLUDING THE SAME

(71) Applicant: SFC CO., LTD., Cheongju (KR)

(72) Inventors: Soon-Wook Cha, Goyang (KR); Yoona Shin, Seoul (KR); Jea-Geon Lim, Cheongju (KR); Sang-Woo Park, Seoul (KR); Ji-Hwam Kim, Anyang (KR); Jung-Ho Yoo, Seosan (KR); Young-Hwan Park, Cheongju (KR)

(73) Assignee: SFC CO., LTD., Cheongju (KR)

( * ) Notice: Subject to any disclaimer, the term of this patent is extended or adjusted under 35 U.S.C. 154(b) by 365 days.

This patent is subject to a terminal disclaimer.

(21) Appl. No.: 15/334,791

(22) Filed: Oct. 26, 2016

(65) Prior Publication Data

US 2017/0141322 A1    May 18, 2017

(30) Foreign Application Priority Data

Nov. 13, 2015 (KR) .......................... 10-2015-0159347
Sep. 26, 2016 (KR) .......................... 10-2016-0123313

(51) Int. Cl.
*H01L 51/00* (2006.01)
*C07D 307/77* (2006.01)
(Continued)

(52) U.S. Cl.
CPC ........ *H01L 51/0061* (2013.01); *C07D 307/77* (2013.01); *C07D 307/91* (2013.01);
(Continued)

(58) Field of Classification Search
CPC ... C07C 211/54; C07C 211/55; C07C 211/60; C07D 307/77; C07D 307/91;
(Continued)

(56) References Cited

U.S. PATENT DOCUMENTS 10,014,479 B2 * 7/2018 Kim .................... H01L 51/0061
2011/0210315 A1 * 9/2011 Goel .................. C07D 207/327
257/40
(Continued)

FOREIGN PATENT DOCUMENTS

CN    102046598 A    5/2011
CN    102558121 A    7/2012
(Continued)

OTHER PUBLICATIONS

Office Action from Chinese National Intellectual Property Administration, Nov. 7, 2018.
(Continued)

*Primary Examiner* — Sean M DeGuire
(74) *Attorney, Agent, or Firm* — STIP Law Group, LLC

(57) ABSTRACT

Disclosed herein are provided an amine compound represented by the following [Chemical Formula A] or [Chemical Formula B], and an organic light-emitting diode comprising the same.

(Continued)

US 11,563,181 B2

Page 2

(52) U.S. Cl.
CPC ........ *C07D 493/10* (2013.01); *H01L 51/0073* (2013.01); *H01L 51/5056* (2013.01); *H01L 51/5096* (2013.01)

(58) Field of Classification Search
CPC .......... C07D 405/14; C09K 2211/1011; H01L 51/0059; H01L 51/0072; H01L 51/0073; H01L 51/0074
See application file for complete search history.

(56) References Cited

U.S. PATENT DOCUMENTS

| | | | | |
|---|---|---|---|---|
| 2012/0112174 | A1* | 5/2012 | Lee | C07D 307/93 257/40 |
| 2012/0168734 | A1* | 7/2012 | Park | C09K 11/06 257/E51.026 |
| 2014/0332787 | A1* | 11/2014 | Hong | C07D 307/91 549/330 |
| 2015/0060785 | A1* | 3/2015 | Kim | H01L 51/0074 257/40 |
| 2016/0190466 | A1* | 6/2016 | Pfister | H01L 51/0061 252/500 |
| 2017/0012214 | A1* | 1/2017 | Pyo | H01L 51/0061 |
| 2017/0062729 | A1* | 3/2017 | Cha | H01L 51/0094 |
| 2017/0133600 | A1* | 5/2017 | Pyo | H01L 51/0061 |
| 2017/0141321 | A1* | 5/2017 | Pyo | C07D 307/91 |

FOREIGN PATENT DOCUMENTS

| | | | |
|---|---|---|---|
| JP | 2012028548 A | * | 2/2012 |
| KR | 1020110000006 A | | 1/2011 |
| KR | 10-1074193 | | 10/2011 |
| KR | 1020120047706 A | | 5/2012 |
| KR | 1020140046303 A | | 4/2014 |
| KR | 10-1455156 | | 10/2014 |
| KR | 1020150130206 A | | 11/2015 |
| KR | 1020160141361 A | | 12/2016 |
| WO | WO-2014185751 A1 | * | 11/2014 ........ C07D 239/26 |
| WO | WO2015174682 A1 | | 11/2015 |

OTHER PUBLICATIONS

Office Action from Korean Intellectual Property Office of PCT/KR2016/015277, dated May 29, 2017.
International Search Report of PCT/KR2016/015277, dated May 29, 2017.
Office action from China National Intellectual Property Administration of 201601974600, dated Jun. 17, 2019.
O.S Wolfbeis, G. Zacharias Etal, Synthesis with Nitriles, XL: The Reaction of 2-Indanone with Malononitrile, Ethyl Cyanoacetate and Tetracyanoethylene, resp, Monaishefte fuer Chemie, Dec. 31, 1975, vol. 106, pp. 1207-1202, Sprinter-Verlag, New York City, USA.
ACS, Database Registry, Jun. 7, 2001, vol. CAS, 339997-35-2, Reaction Database.

* cited by examiner

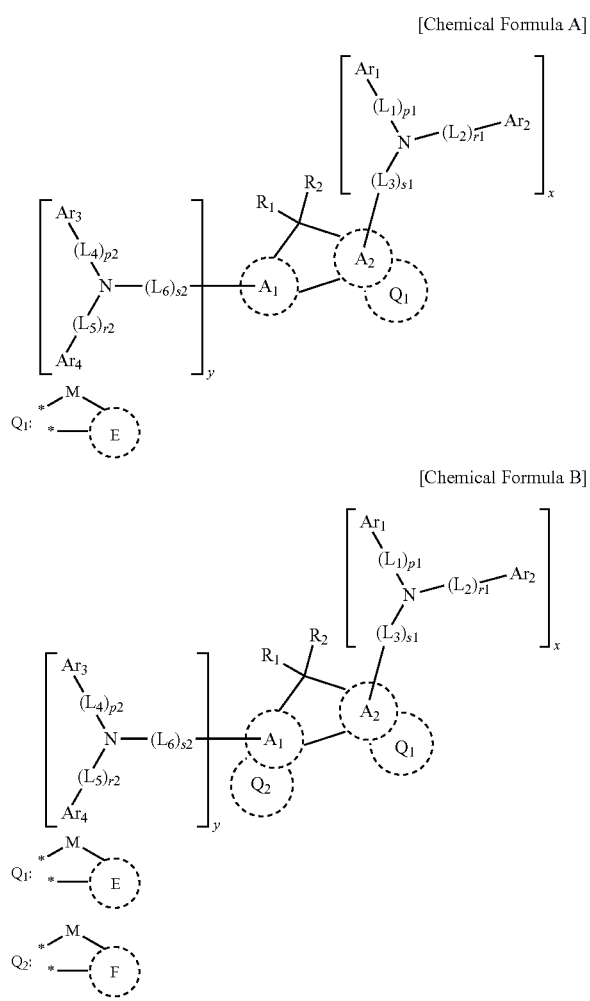

[Chemical Formula A]

[Chemical Formula B]

wherein, the ring moieties, $A_1$, $A_2$, $Q_1$, $Q_2$, E, F, $L_1$ to $L_6$, $Ar_1$ to $Ar_4$, p1, p2, r1, r2, s1, s2, x, and y are each as defined in the Specification.

11 Claims, 2 Drawing Sheets

(51) Int. Cl.
*C07D 307/91* (2006.01)
*C07D 493/10* (2006.01)
*H01L 51/50* (2006.01)

AMINE COMPOUNDS FOR ORGANIC LIGHT-EMITTING DIODE AND ORGANIC LIGHT-EMITTING DIODE INCLUDING THE SAME

CROSS REFERENCE TO RELATED APPLICATION(S)

This application claims priority to and incorporates herein by reference all disclosure in Korean Patent Applications No. 10-2015-0159347 filed Nov. 13, 2015, and No. 10-2016-0123313 filed Sep. 26, 2016.

BACKGROUND OF THE INVENTION

1. Field of the Invention

The present disclosure relates to a novel amine suitable for use in organic light-emitting diodes. More particularly, the present disclosure relates to a novel amine compound that secures excellent properties, such as high luminous efficiency, long lifespan and low driving voltages, for an organic light-emitting diodes when used in a hole transport layer or an electron-blocking layer in the organic light-emitting diode, and an organic light-emitting diode including the same.

2. Description of the Related Art

Organic light-emitting diodes (OLEDs), based on self-luminescence, are used to create digital displays having the advantage of being able to be made thinner and lighter than liquid crystal displays (LCDs). In addition, an OLED display exhibits a much faster response time than an LCD. Accordingly, organic light-emitting diodes find applications in the illumination field as well as the full-color display field.

In general, the term organic light-emitting phenomenon refers to a phenomenon in which electric energy is converted to light energy by means of an organic material. An organic light-emitting diode using the organic light-emitting phenomenon has a structure usually comprising an anode, a cathode, and an organic material layer interposed therebetween.

In this regard, the organic material layer may be of a multilayer structure consisting of different materials, for example, a hole injection layer, a hole transport layer, a light-emitting layer, an electron transport layer, and an electron injection layer, in order to improve efficiency and stability of the organic light emitting diode. In the organic light-emitting diode having such a structure, when a voltage is applied between the two electrodes, a hole injected from the anode migrates to the organic layer while an electron is released from the cathode and moves toward the organic layer. In the luminescent zone, the hole and the electron recombine to produce an exciton. When the exciton returns to the ground state from the excited state, the molecule of the organic layer emits light. Such an organic light emitting diode is known to have characteristics such as self-luminescence, high luminance, high efficiency, low driving voltage, wide viewing angle, high contrast and high-speed response.

The materials used as organic layers in organic light-emitting diodes may be divided into luminescent materials and charge-carrying materials, for example, a hole injection material, a hole transport material, an electron injection material, and an electron transport material and, as needed, further into an electron-blocking material or a hole-blocking material.

With regard to related arts pertaining to hole transport layers, reference may be made to Korean Patent No. 10-1074193 (issued Oct. 14, 2011), which describes an organic light-emitting diode using a carbazole structure fused with at least one benzene ring in a hole transport layer, and Korean Patent No. 10-1455156 (issued Oct. 27, 2014), which describes an organic light-emitting diode in which the HOMO energy level of an auxiliary light-emitting layer is set between those of a hole transport layer and a light-emitting layer.

In spite of enormous effort for fabricating organic light-emitting diodes having more effective luminous properties, there is still continued need to develop novel organic light-emitting materials suitable for use in hole injection layers and hole transport layers of organic light-emitting diodes that can operate at lower voltage with higher light emission efficiency and longer lifetime, compared to those developed based on conventional technology.

RELATED ART DOCUMENT

Korean Patent No. 10-1074193 (Oct. 14, 2011)

Korean Patent No. 10-1455156 (Oct. 27, 2014)

SUMMARY OF THE INVENTION

Therefore, it is an object of the present disclosure to provide a novel amine compound, available for use in a hole transport layer, a hole injection layer, or an electron-blocking layer.

It is another object of the present disclosure to provide an organic light-emitting diode (OLED) that comprises the amine compound in a hole transport layer, a hole injection layer, or an electron-blocking layer, thereby exhibiting excellent diode properties, such as high luminous efficiency, long lifespan, and low driving voltages.

In accordance with an aspect thereof, the present disclosure provides an amine compound represented by the following Chemical Formula A or B:

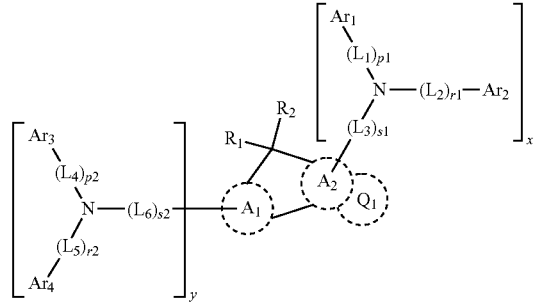

[Chemical Formula A]

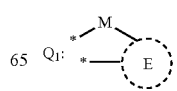

-continued

[Chemical Formula B]

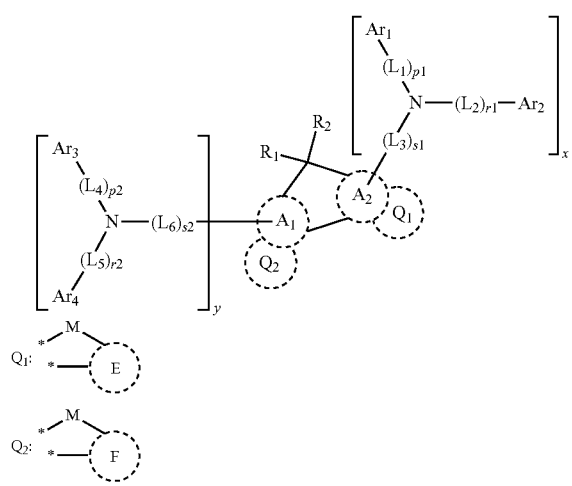

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which the substituents $R_1$ and $R_2$ are bonded;

linkers $L_1$ to $L_6$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_4$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 6 to 30 carbon atoms, a cyano, a nitro, and a halogen, with the proviso that $R_1$ and $R_2$ together may form a mono- or polycyclic aliphatic or aromatic ring, which may be a heterocyclic ring containing a heteroatom selected from among N, O, P, Si, S, Ge, Se, and Te as a ring member;

p1, p2, r1, r2, s1, and s2 are each independently an integer of 1 to 3, with the proviso that when any of them is 2 or greater, the corresponding linkers may be the same or different;

$Ar_1$ may form a ring with $Ar_2$, and Ara may form a ring with $Ar_4$;

x and y are each 0 or 1 with the proviso that x+y=1;

two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions of * of Structural Formula $Q_1$ to form a fused ring, wherein the term 'substituted' in the expression 'substituted or unsubstituted' for Chemical Formulas A and B means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

In accordance with another aspect thereof, the present disclosure provides an organic light-emitting diode, comprising: a first electrode; a second electrode facing the first electrode; and an organic layer interposed between the first electrode and the second electrode, wherein the organic layer comprises at least one of the amine compounds of the present disclosure:

BRIEF DESCRIPTION OF THE DRAWINGS

The above and other objects, features and advantages of the present disclosure will be more clearly understood from the following detailed description taken in conjunction with the accompanying drawing, in which.

DESCRIPTION OF THE PREFERRED EMBODIMENTS

Figure 1:
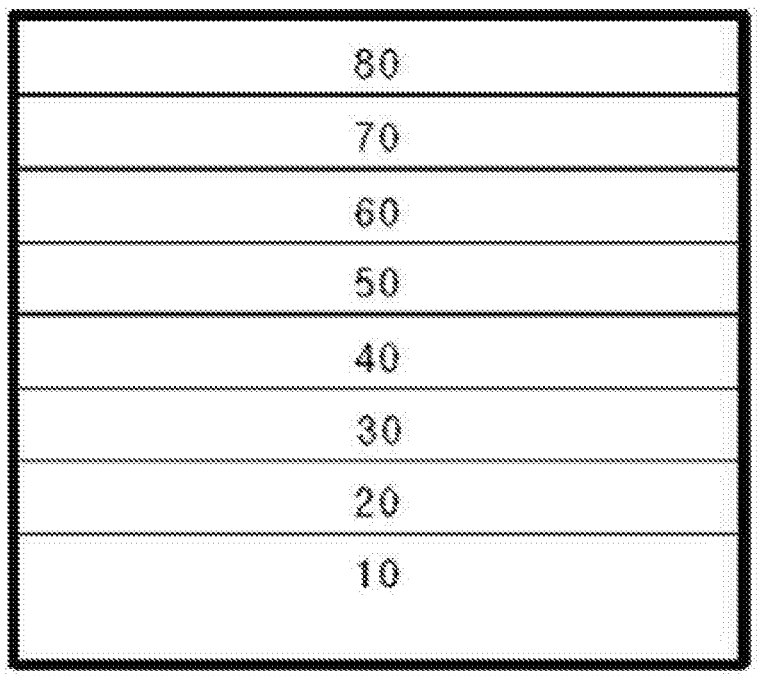
FIG. 1 is a schematic cross-sectional view of the structure of an organic light-emitting diode according to an embodiment of the present disclosure.

Hereinafter, some embodiments which can be easily embodied by those skilled in the art will be described with reference to the accompanying drawings. In the drawings of the invention, the sizes and dimensions of structures are illustrated by enlarging or reducing them relative to the actual sizes and dimensions to clarify the invention, the known configurations are not illustrated in order to emphasize characteristic configurations, and the invention is not limited to the drawings. In describing the phenomena of the preferred embodiments of the invention in detail, when it is determined that a detailed description of related known functions or configurations may unnecessarily obscure the gist of the invention, such a detailed description is omitted.

In addition, the size and thickness of each configuration illustrated in the drawings are arbitrarily illustrated for the sake of convenience of explanation, and thus the present disclosure may not be necessarily limited to what is shown in the illustration. Further, in the drawings, the thicknesses of layers and regions may be exaggerated for clarity. It will be understood that when an element such as a layer, film, region or substrate is referred to as being "on" another element, it may be directly on the other element or intervening elements may also be present.

Throughout the specification, when a portion may "include" a certain constituent element, unless specified otherwise, it may not be construed to exclude another constituent element but may be construed to further include other constituent elements.

In addition, unless explicitly described to the contrary, the word "comprise" and variations such as "comprises" or "comprising" will be understood to imply the inclusion of stated elements but not the exclusion of any other elements. Further, throughout the specification, the word "on" means positioning on or below the object portion, but does not essentially mean positioning on the lower side of the object portion based on a direction of gravity.

The present disclosure addresses a novel amine compound represented by the following Chemical Formula A or B:

[Chemical Formula A]

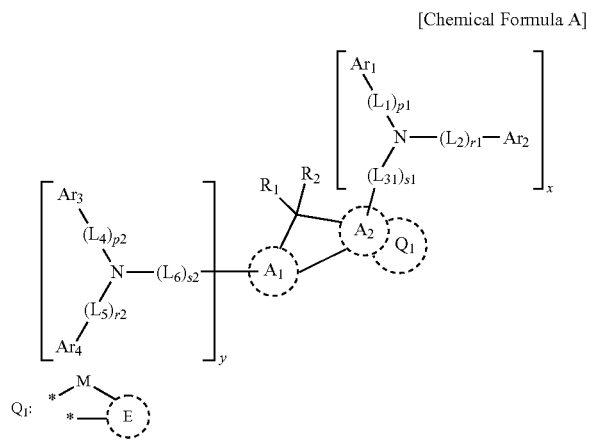

[Chemical Formula B]

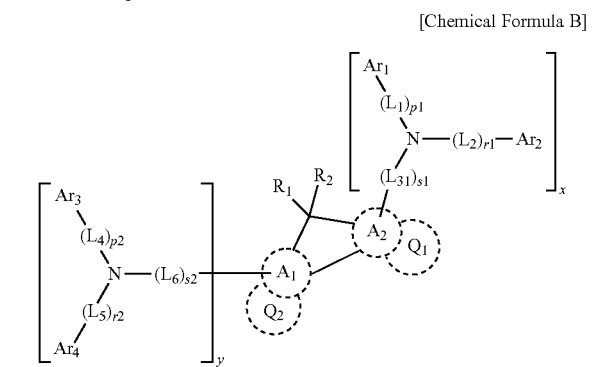

-continued

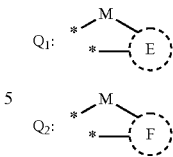

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring A and two adjacent carbon atoms of the aromatic ring $A_2$ form a 5-membered fused ring together with a carbon atom to which the substituents $R_1$ and $R_2$ are bonded;

linkers $L_1$ to $L_6$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_4$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 6 to 30 carbon atoms, a cyano, a nitro, and a halogen, with the proviso that $R_1$ and $R_2$ together may form a mono- or polycyclic aliphatic or aromatic ring, which may be a heterocyclic ring containing a heteroatom selected from among N, O, P, Si, S, Ge, Se, and Te as a ring member;

p1, p2, r1, r2, s1, and s2 are each independently an integer of 1 to 3, with the proviso that when any of them is 2 or greater, the corresponding linkers may be the same or different;

$Ar_1$ may form a ring with $Ar_2$, and $Ar_3$ may form a ring with $Ar_4$;

x and y are each 0 or 1 with the proviso that x+y=1;

two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring, and two adjacent carbon atoms of the $A_2$ ring moiety of Chemical Formula B may occupy respective positions of * of Structural Formula $Q_1$ to form a fused ring, wherein the term 'substituted' in the expression 'substituted or unsubstituted' for Chemical Formulas A and B means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms such as in "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" means an organic radical, derived from an aromatic hydrocarbon by removing one hydrogen atom. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—$NH_2$, —NH(R), —N(R')(R") wherein R' and R" are each independently an alkyl of 1 to 10 alkyl, in this case called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms containing one to three heteroatoms selected from among N, O, P, Si, S, Ge, Se, and Te. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atom of the silyl may be substituted by the same substituent as in the aryl.

The amine compound represented by Chemical Formula A or B used in the organic light-emitting diode of the present disclosure is characterized by a structure in which the amine group exists only on one of the $A_1$ and $A_2$ ring moieties. The use of the amine compound according to the present disclosure in a hole transport layer, a hole injection layer or an electron blocking layer guarantees that the organic light-emitting diode exhibits high luminous efficiency, a long lifespan, and a low driving voltage.

In one embodiment, when x is 1 and y is 0 in Chemical Formula A while Structural Formula $Q_1$ is connected to the $A_2$ ring moiety, only the amine moiety containing $Ar_1$ and $Ar_2$ can be connected to the $A_2$ ring moiety.

In another embodiment, when x is 0 and y is 1 in Chemical Formula A while Structural Formula $Q_1$ is connected to the $A_2$ ring moiety, only the amine moiety containing $Ar_3$ and $Ar_4$ can be connected to the $A_1$ ring moiety.

In another embodiment, when x is 1 and y is 0 in Chemical Formula B while Structural Formulas $Q_2$ and $Q_1$ are respectively connected to the $A_1$ and $A_2$ ring moieties, only the amine moiety containing $Ar_3$ and $Ar_2$ can be connected to the $A_2$ ring moiety.

In another embodiment, when x is 0 and y is 1 in Chemical Formula B while Structural Formulas $Q_2$ and $Q_1$ are respectively connected to the $A_1$ and $A_2$ ring moieties, only the amine moiety containing $Ar_3$ and $Ar_4$ can be connected to the $A_1$ ring moiety.

According to a particular embodiment of the present disclosure, $A_1$, $A_2$, E, and F in Chemical Formula A or B may be the same or different, and are independently a substituted or unsubstituted aromatic hydrocarbon ring of 6 to 50 carbon atoms.

When $A_1$, $A_2$, E, and F in Chemical Formula A or B may be the same or different, and are independently a substituted or unsubstituted aromatic hydrocarbon ring of 6 to 50 carbon atoms, the substituted or unsubstituted aromatic hydrocarbon ring of 6 to 50 carbon atoms may be selected from the group consisting of [Structural Formula 10] to [Structural Formula 21]:

[Structural Formula 10]

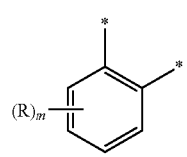

[Structural Formula 11]

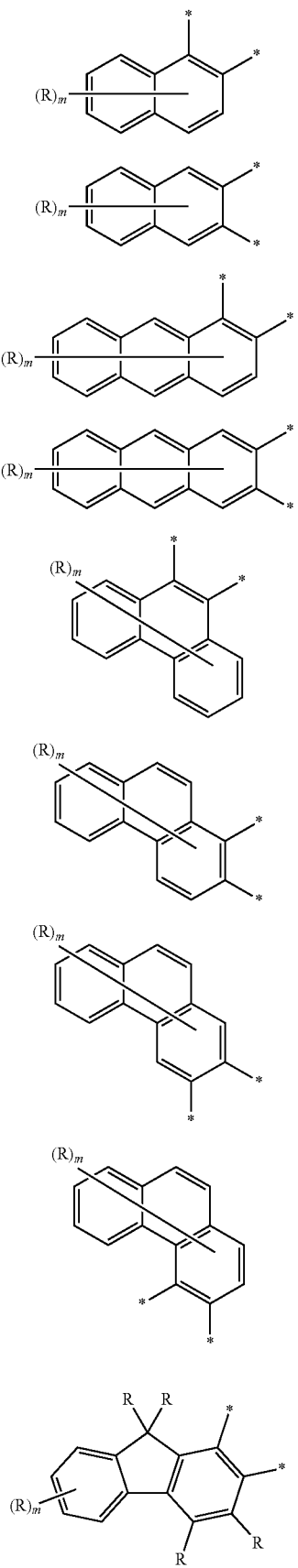

[Structural Formula 12]

[Structural Formula 13]

[Structural Formula 14]

[Structural Formula 15]

[Structural Formula 16]

[Structural Formula 17]

[Structural Formula 18]

[Structural Formula 19]

[Structural Formula 20]

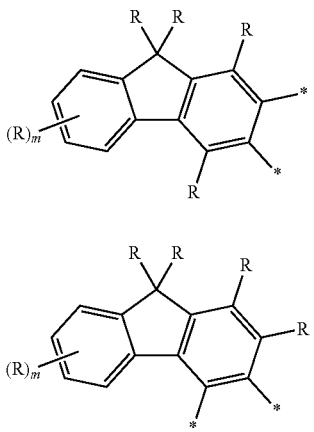

[Structural Formula 21]

wherein

"-*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R's are the same as defined above for $R_1$ and $R_2$, m is an integer of 1 to 8, with the proviso that when m is 2 or greater or when two or more R's exist, the corresponding R's may be the same or different.

According to a particular embodiment of the present disclosure, x in Chemical Formulas A and B may be 1.

In this regard, linkers $L_1$ to $L_6$ of Chemical Formulas A and B may each be a single bond, or any one selected from the following [Structural Formula 22] to [Structural Formula 30], p1, p2, r1, r2, s1, and s2 may each be 1 or 2

[Structural Formula 22]

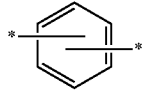

[Structural Formula 23]

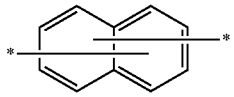

[Structural Formula 24]

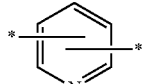

[Structural Formula 25]

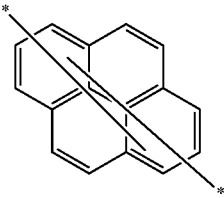

[Structural Formula 26]
[Structural Formula 27]
[Structural Formula 28]
[Structural Formula 29]
[Structural Formula 30]

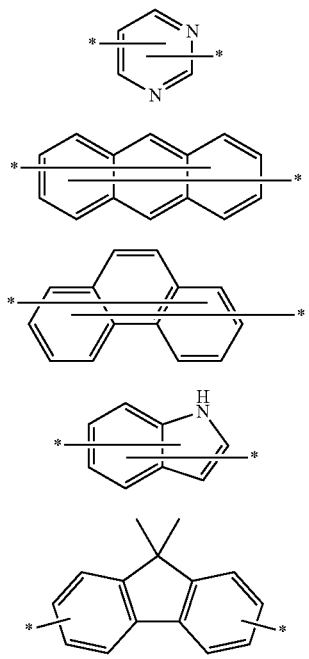

In the linker, each of the unsubstituted carbon atoms of the aromatic ring moiety is bound with a hydrogen atom or a deuterium atom.

The amine compound represented by Chemical Formula A or B, useful in the organic light-emitting diode of the present disclosure, may be selected from compounds represented by the following [Chemical Formula 1] to [Chemical Formula 165], but is not limited thereto.

<Chemical Formula 1>

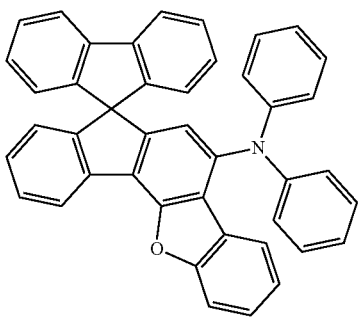

<Chemical Formula 2>

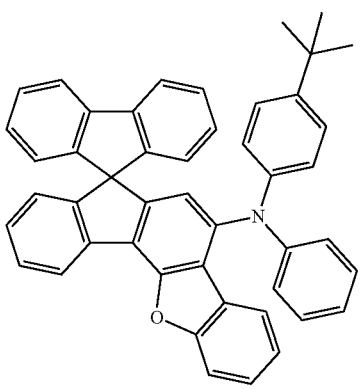

<Chemical Formula 3>

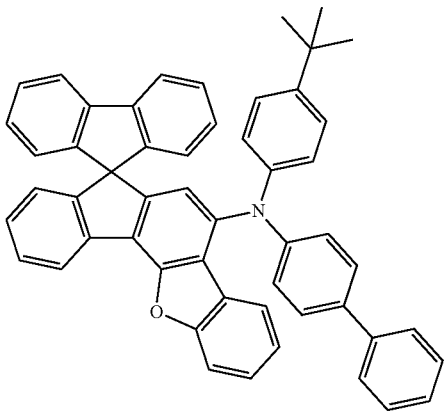

<Chemical Formula 4>

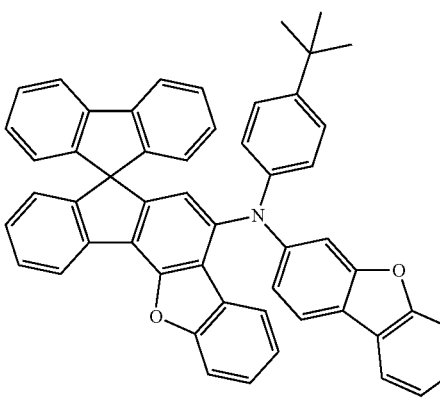

<Chemical Formula 5>

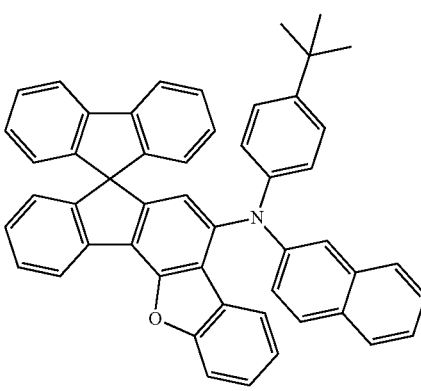

<Chemical Formula 6>

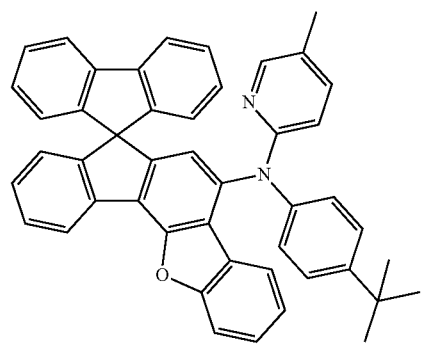

<Chemical Formula 7>
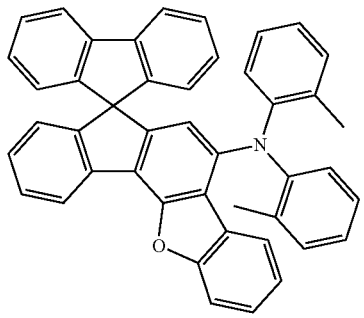
<Chemical Formula 8>
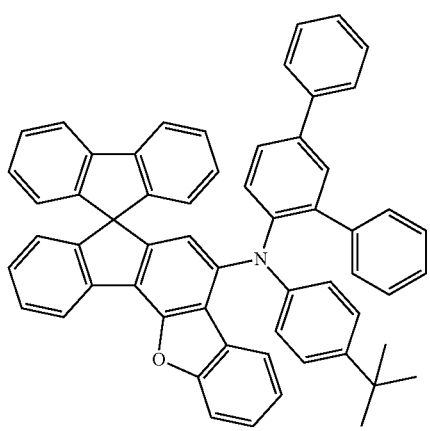
<Chemical Formula 9>
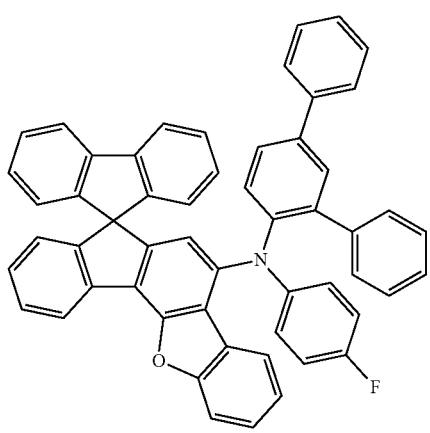
<Chemical Formula 10>
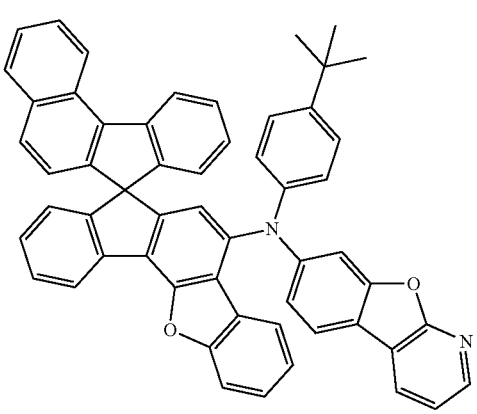
<Chemical Formula 11>
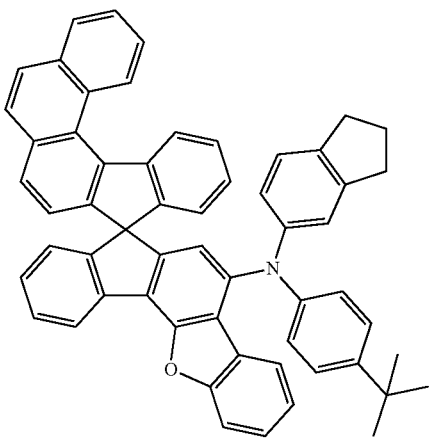
<Chemical Formula 12>
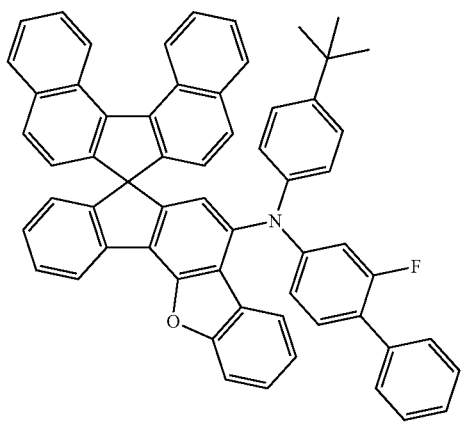
<Chemical Formula 13>
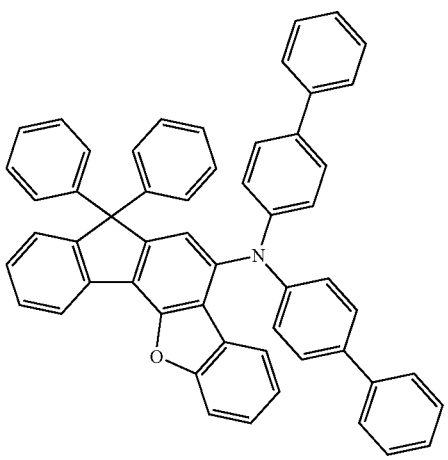

<Chemical Formula 14>
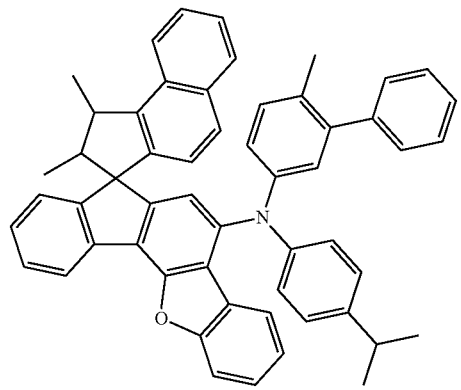
<Chemical Formula 15>
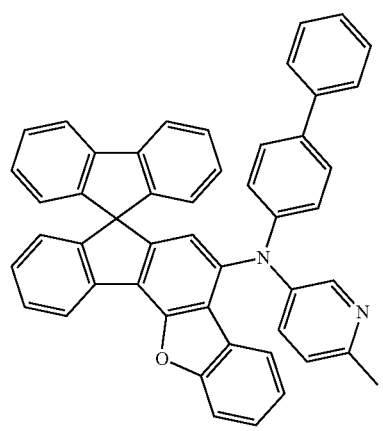
<Chemical Formula 16>
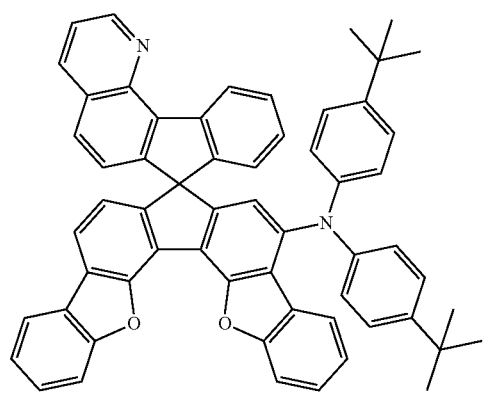
<Chemical Formula 17>
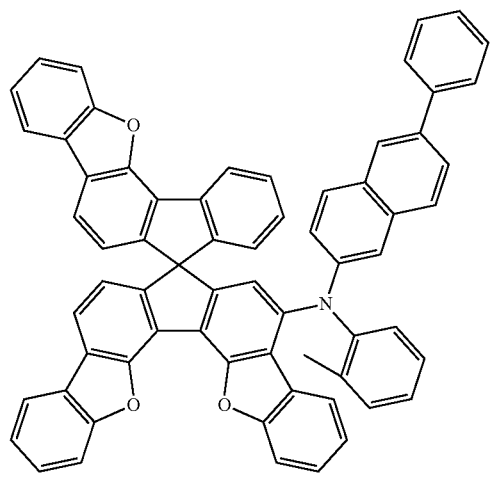
<Chemical Formula 18>
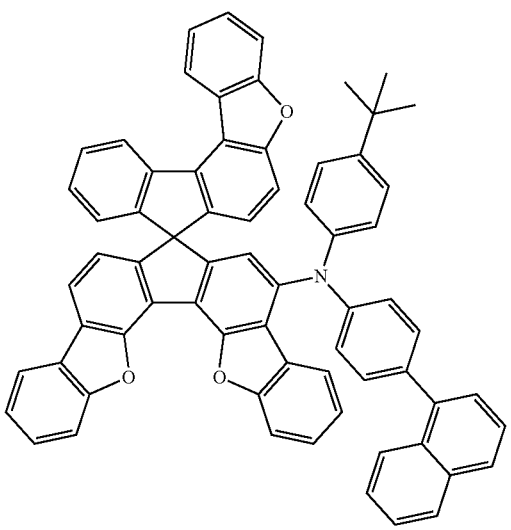
<Chemical Formula 19>
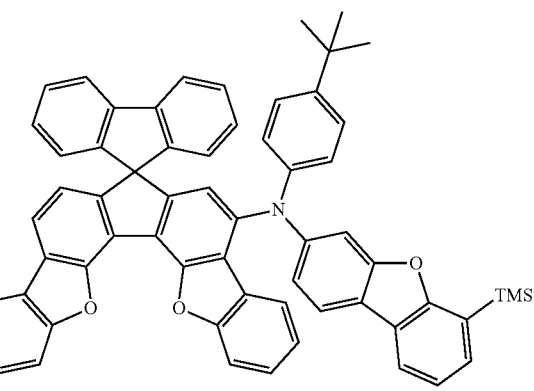

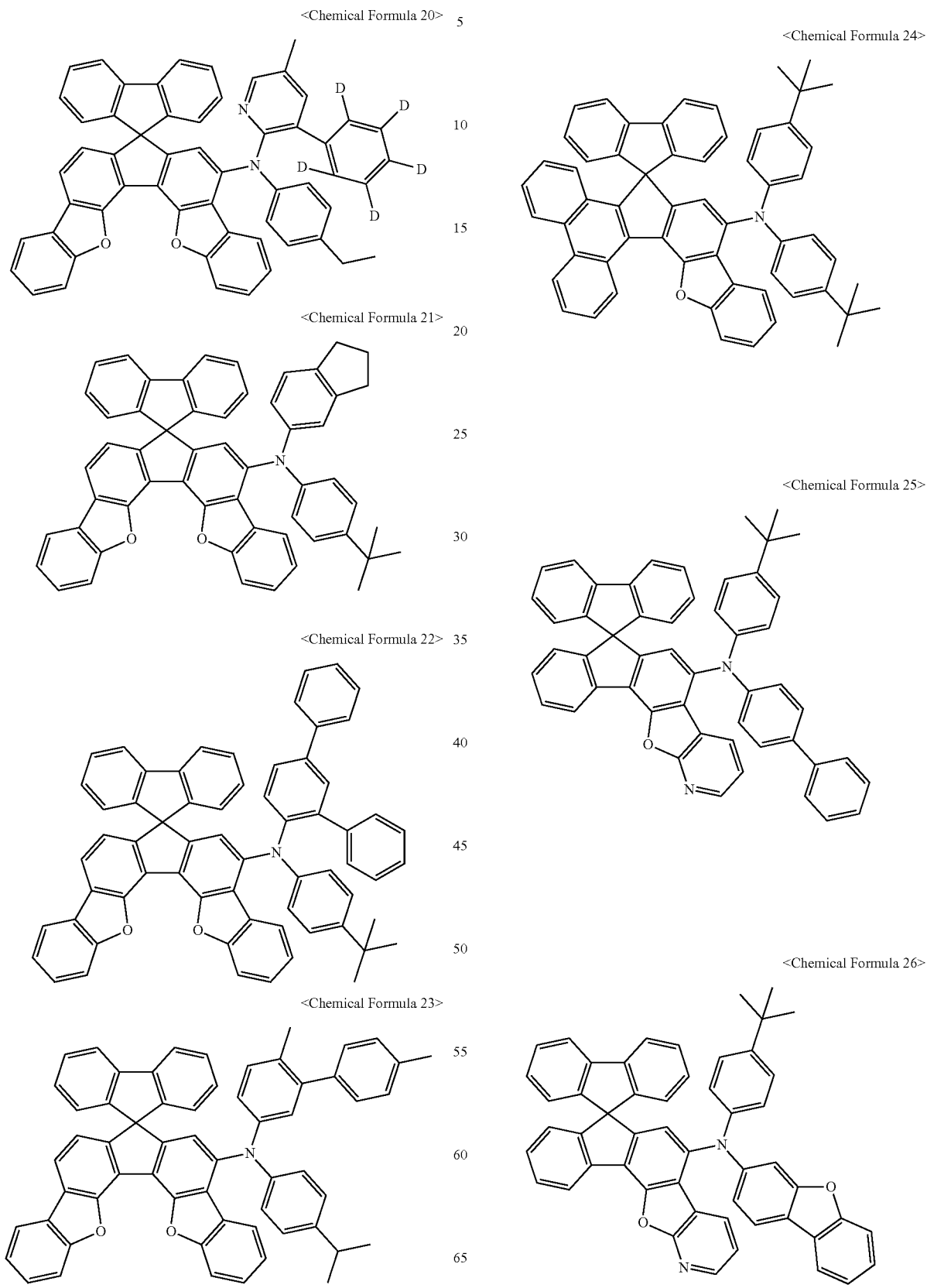

<Chemical Formula 27>
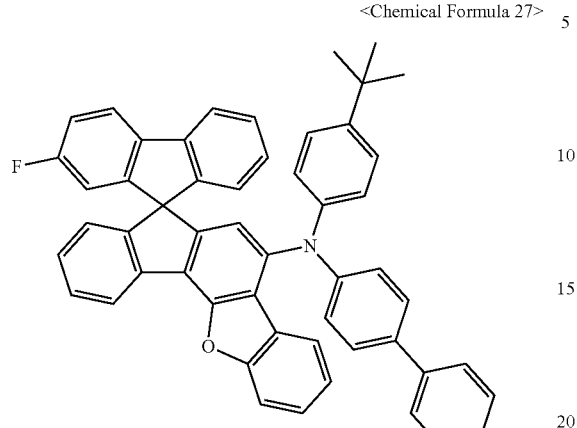
<Chemical Formula 28>
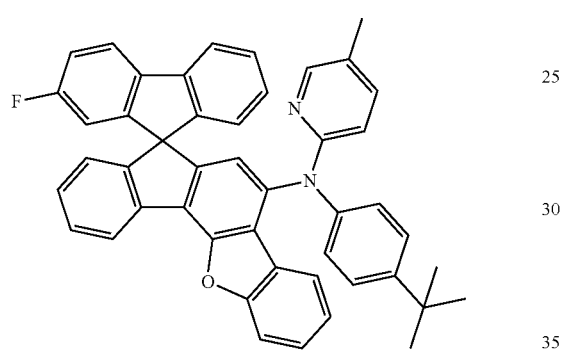
<Chemical Formula 29>
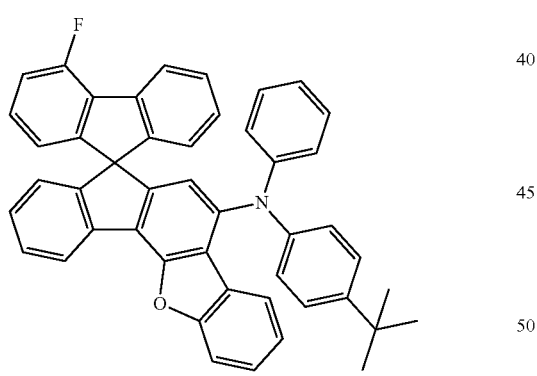
<Chemical Formula 30>
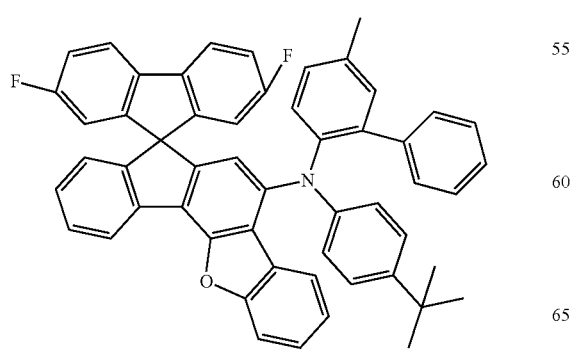
<Chemical Formula 31>
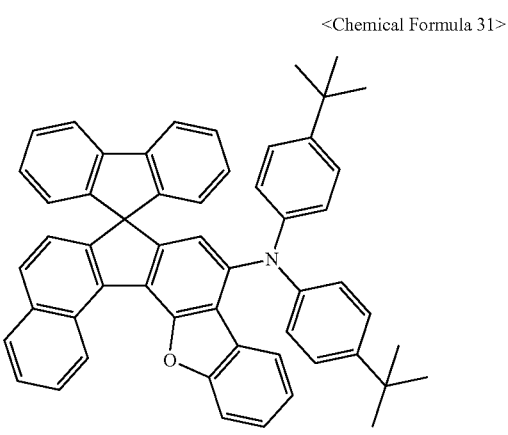
<Chemical Formula 32>
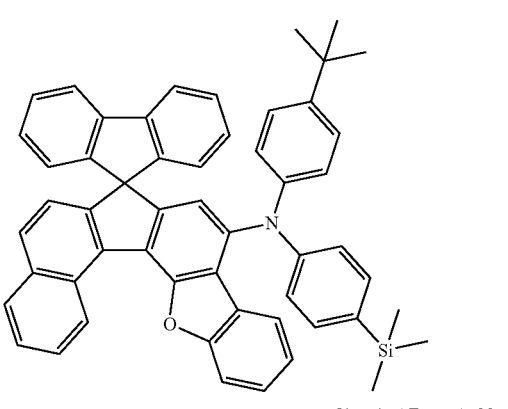
<Chemical Formula 33>
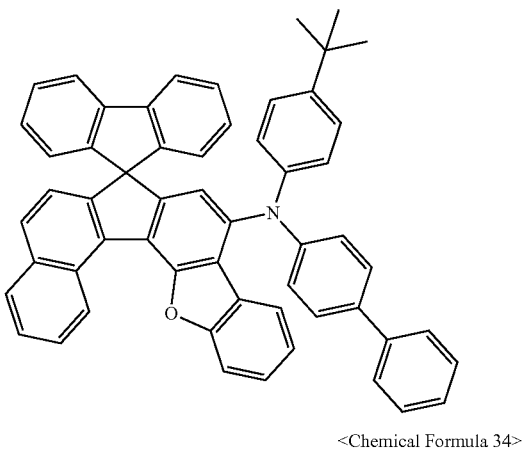
<Chemical Formula 34>
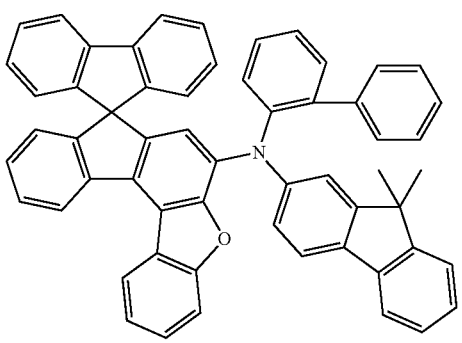

<Chemical Formula 35>
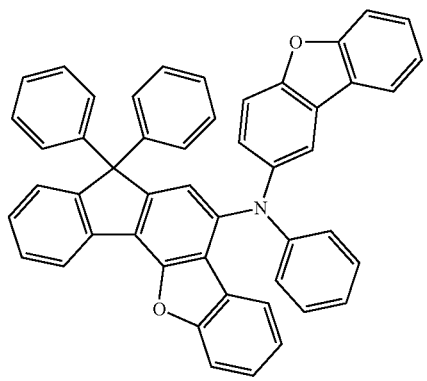
<Chemical Formula 36>
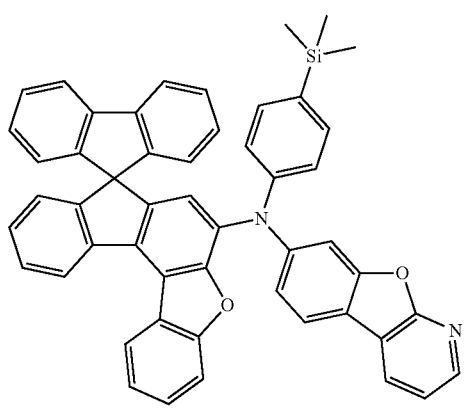
<Chemical Formula 37>
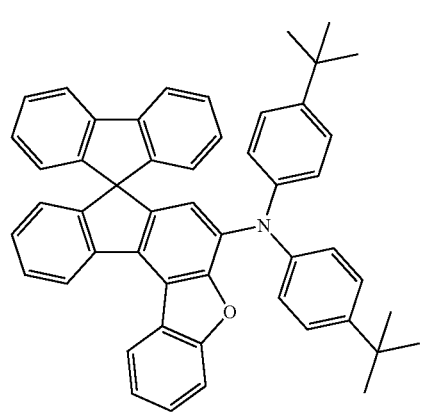
<Chemical Formula 38>
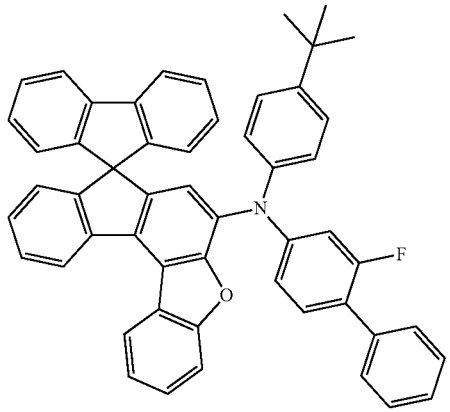
<Chemical Formula 39>
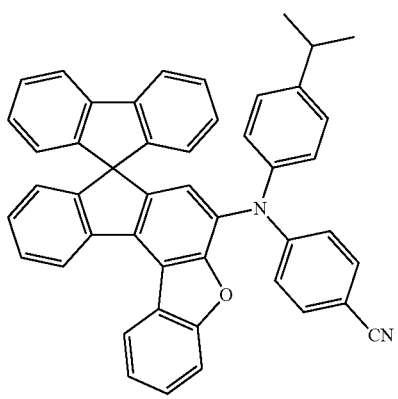
<Chemical Formula 40>
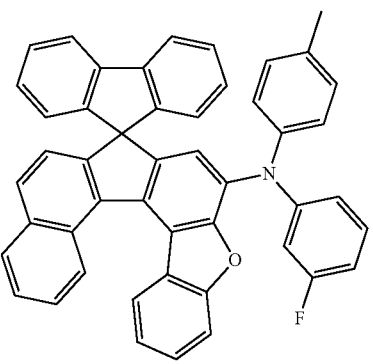
<Chemical Formula 41>
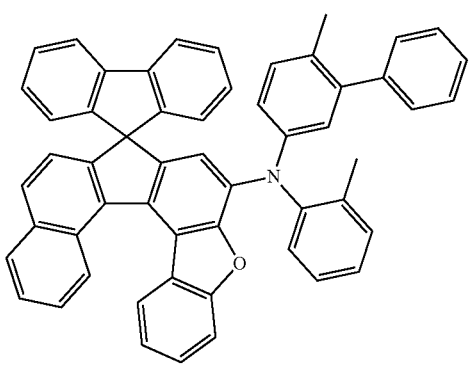

<Chemical Formula 42>
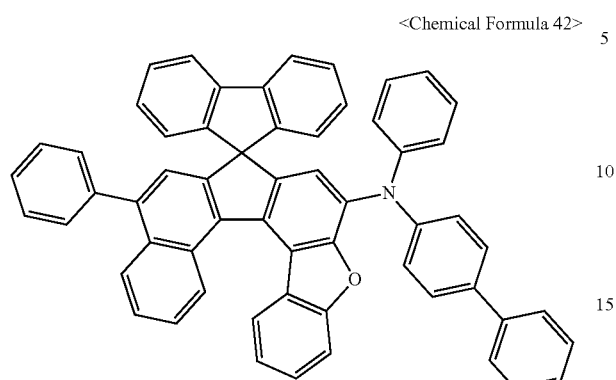
<Chemical Formula 43>
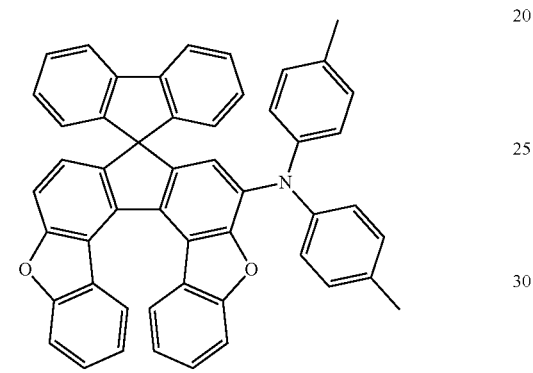
<Chemical Formula 44>
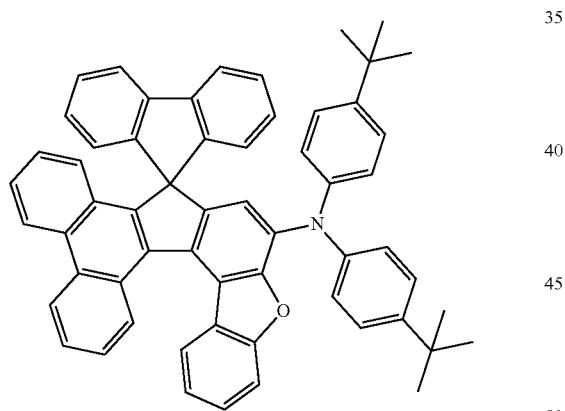
<Chemical Formula 45>
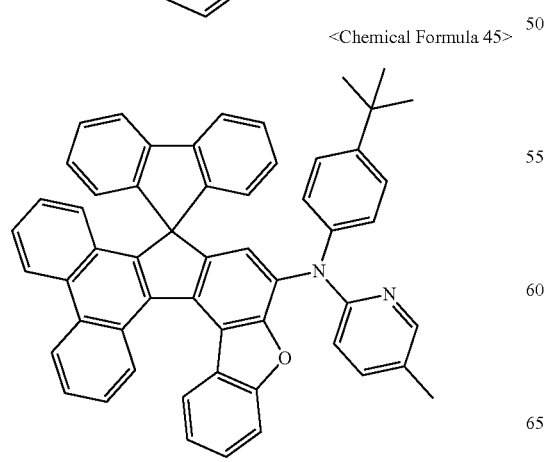
<Chemical Formula 46>
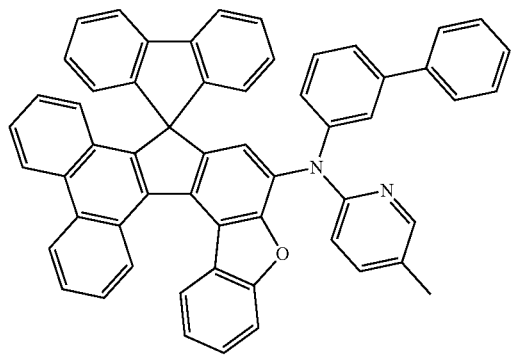
<Chemical Formula 47>
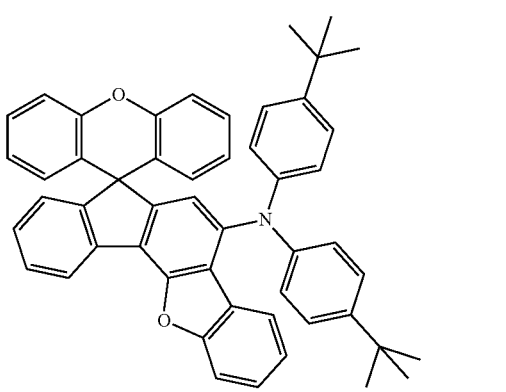
<Chemical Formula 48>
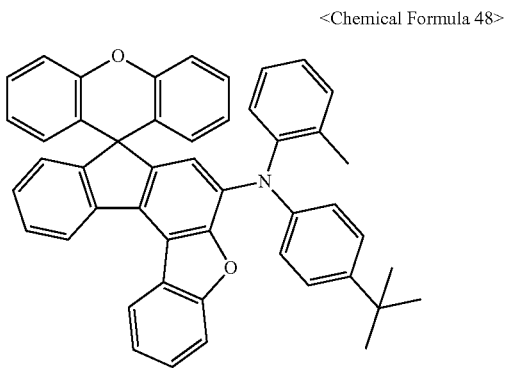
<Chemical Formula 49>
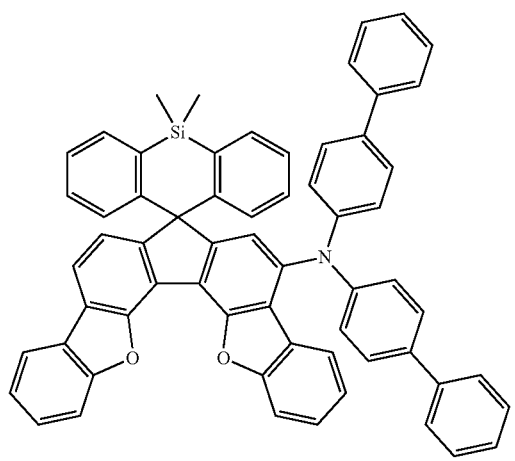

<Chemical Formula 50>
<Chemical Formula 51>
<Chemical Formula 52>
<Chemical Formula 53>
<Chemical Formula 54>
<Chemical Formula 55>
<Chemical Formula 56>
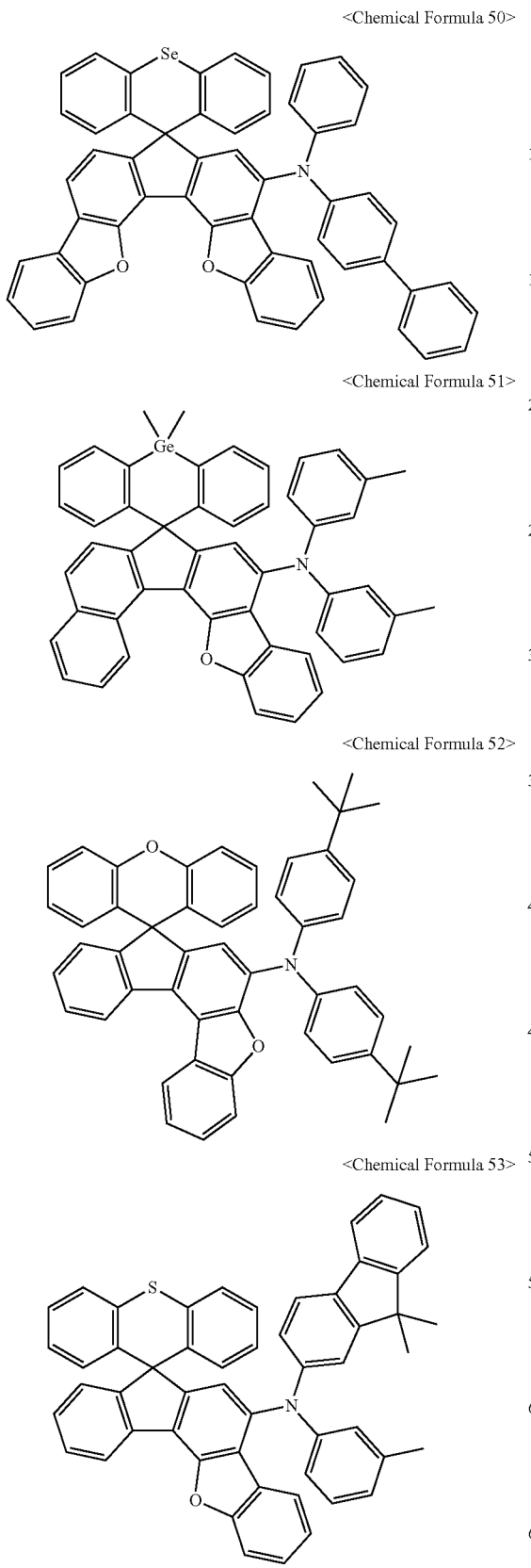
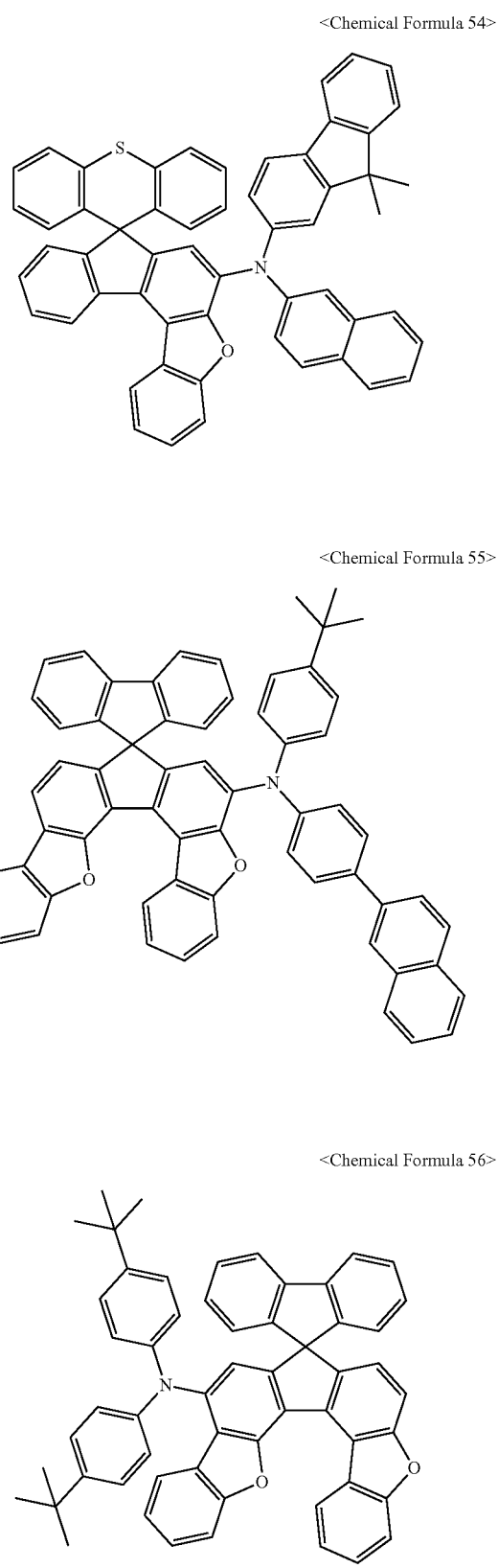

<Chemical Formula 57>
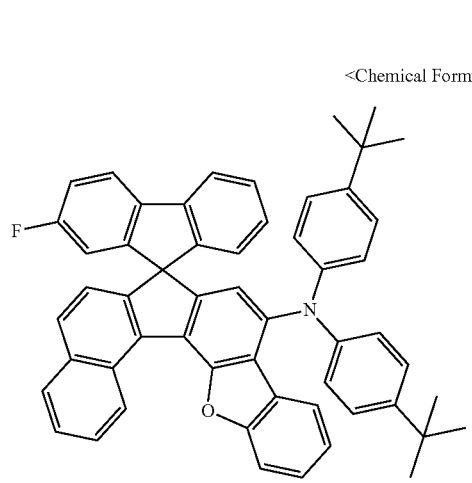
<Chemical Formula 58>
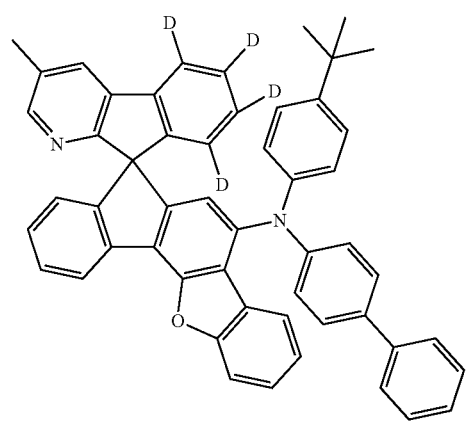
<Chemical Formula 59>
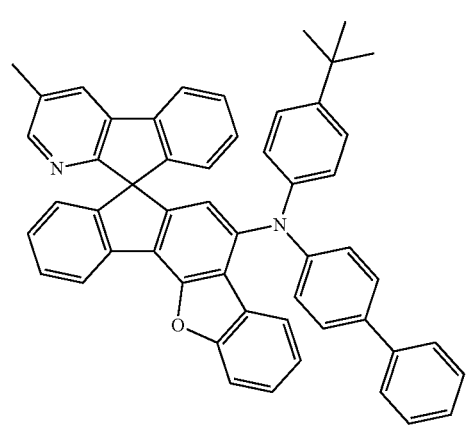
<Chemical Formula 60>
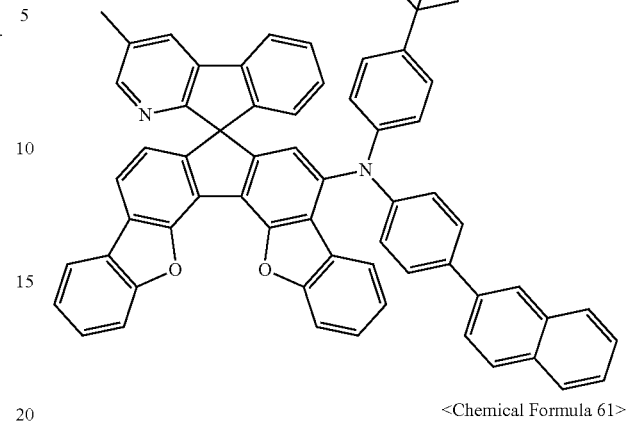
<Chemical Formula 61>
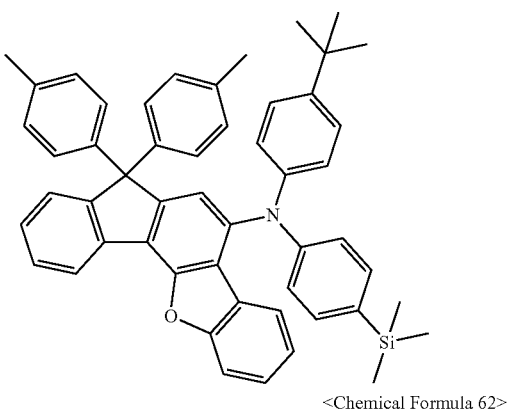
<Chemical Formula 62>
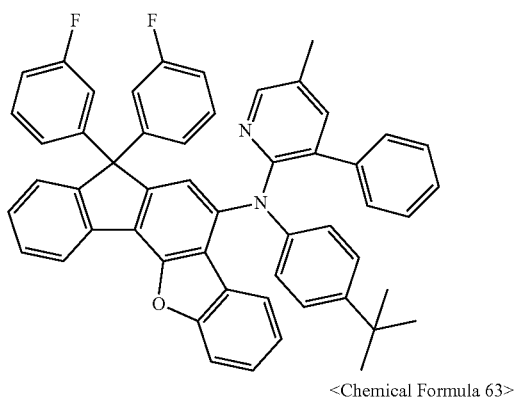
<Chemical Formula 63>
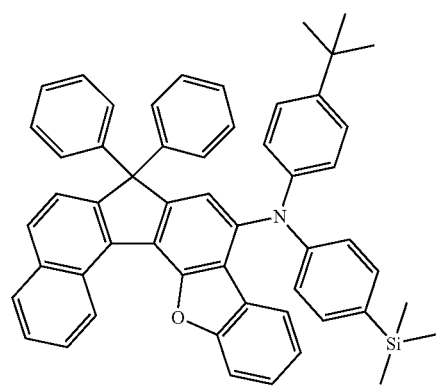

<Chemical Formula 64>
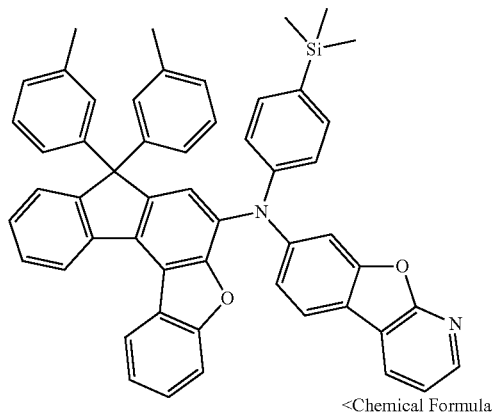
<Chemical Formula 65>
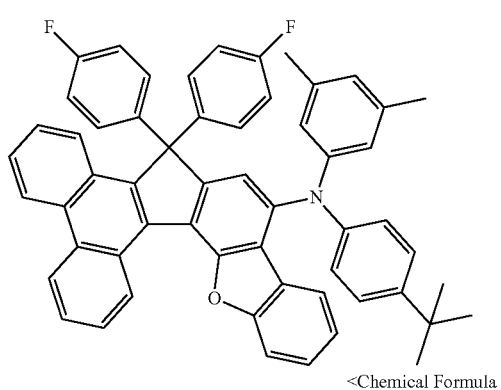
<Chemical Formula 66>
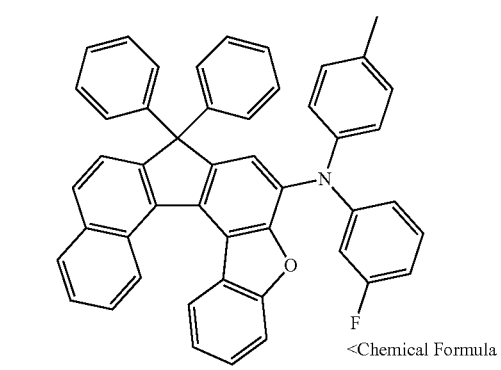
<Chemical Formula 67>
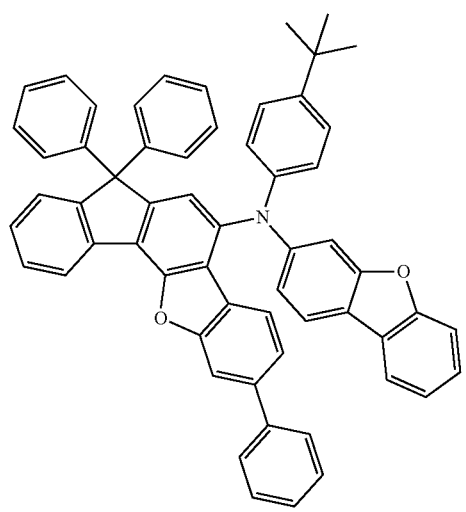
<Chemical Formula 68>
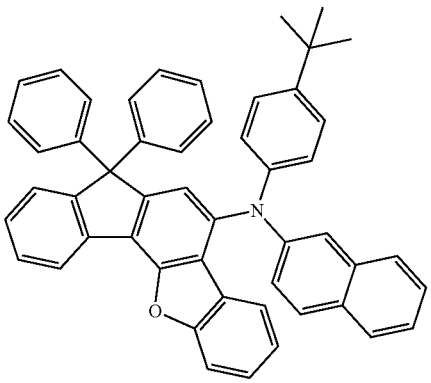
<Chemical Formula 69>
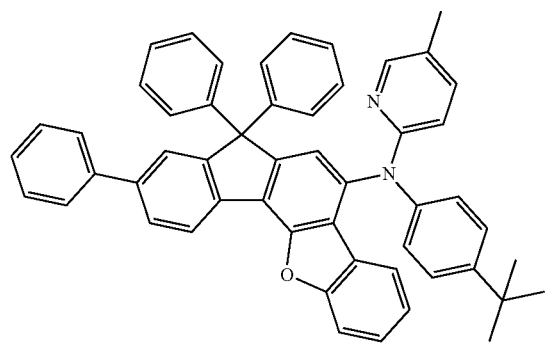
<Chemical Formula 70>
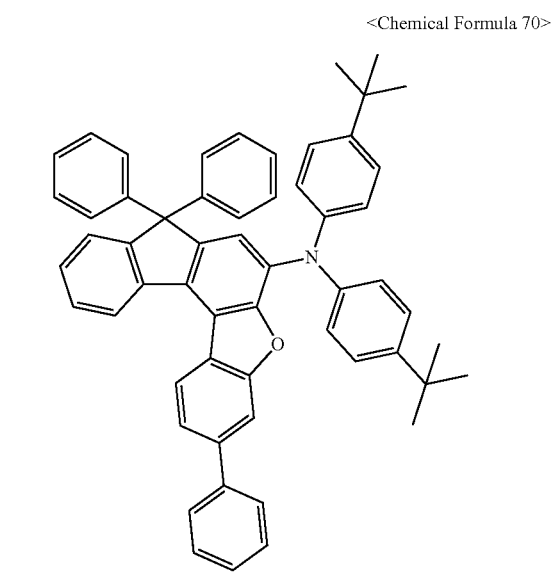

<Chemical Formula 71>
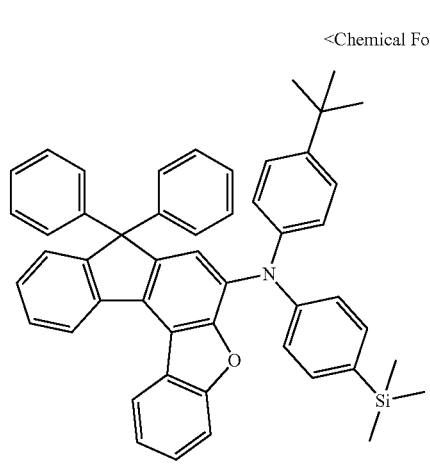
<Chemical Formula 72>
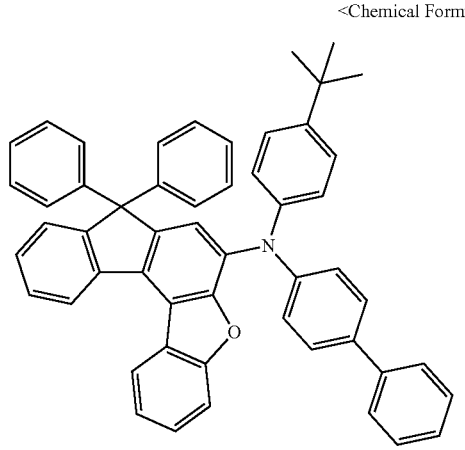
<Chemical Formula 73>
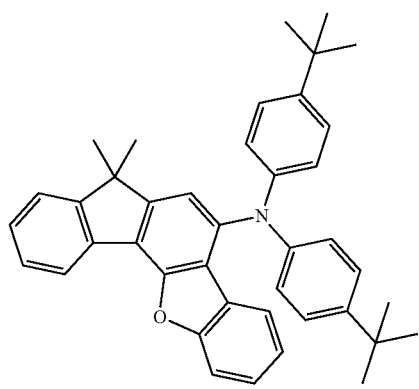
<Chemical Formula 74>
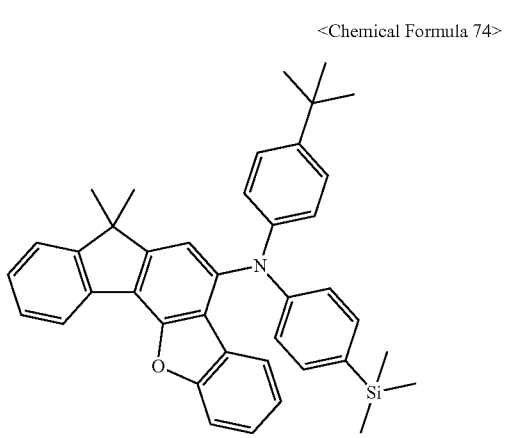
<Chemical Formula 75>
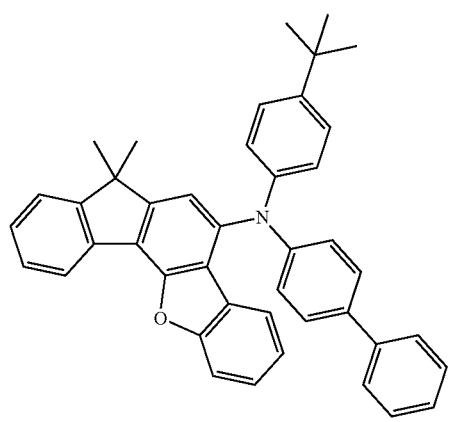
<Chemical Formula 76>
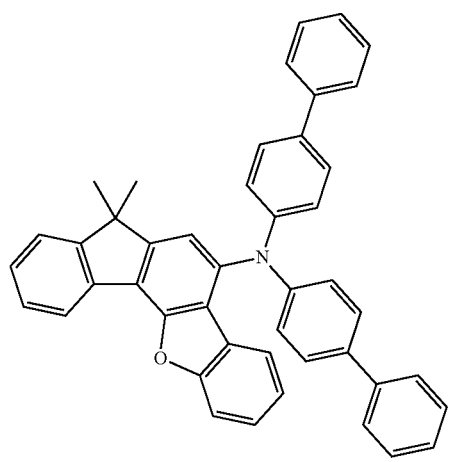

<Chemical Formula 77>
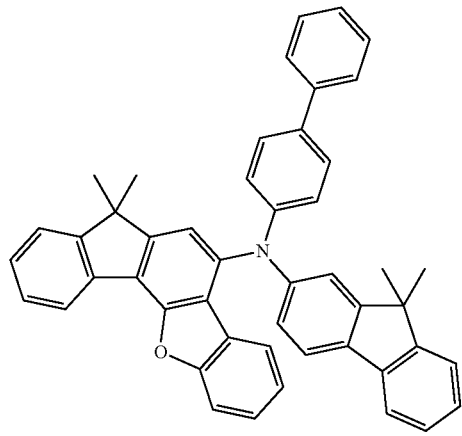
<Chemical Formula 78>
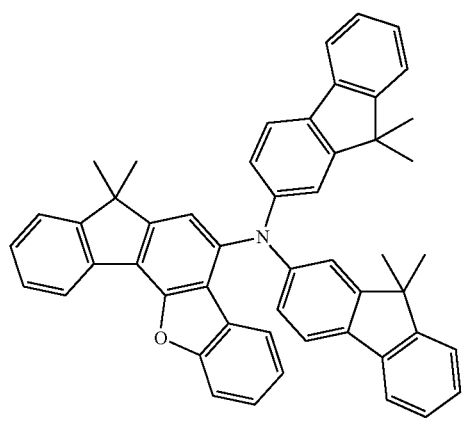
<Chemical Formula 79>
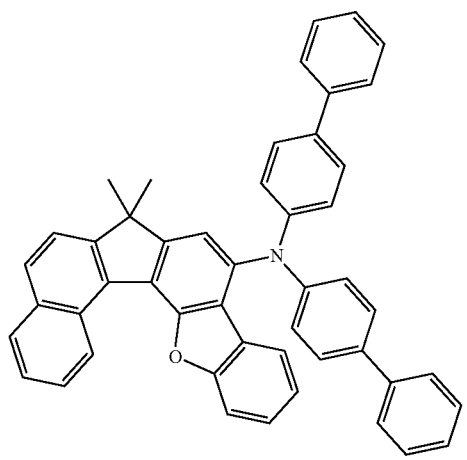
<Chemical Formula 80>
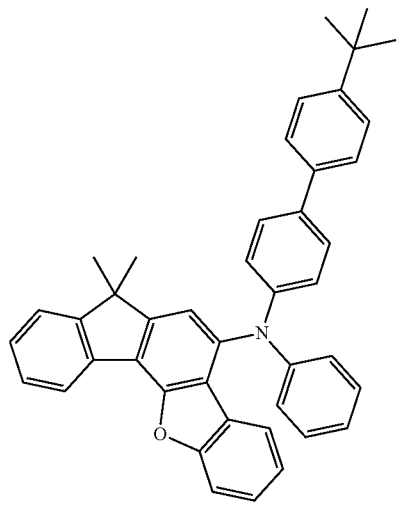
<Chemical Formula 81>
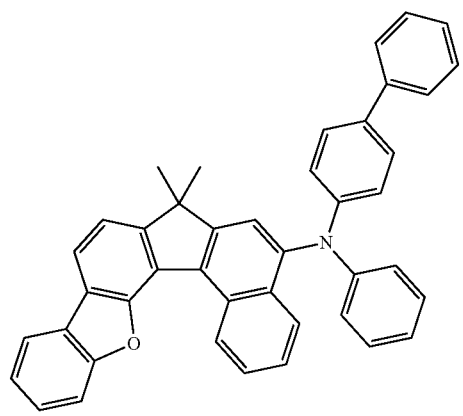
<Chemical Formula 82>
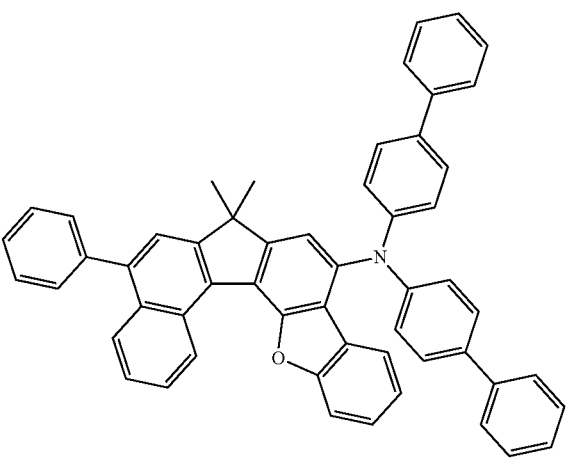

<Chemical Formula 83>
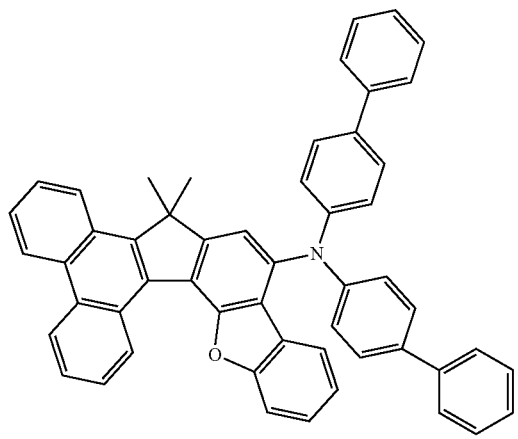
<Chemical Formula 84>
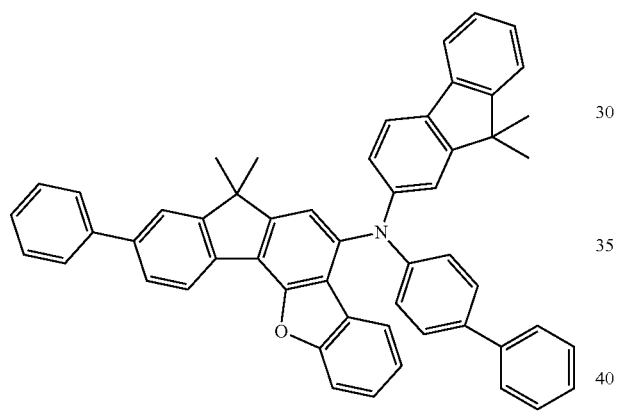
<Chemical Formula 85>
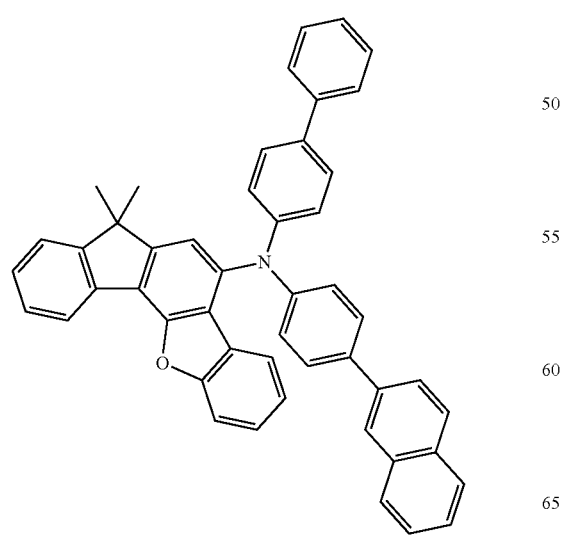
<Chemical Formula 86>
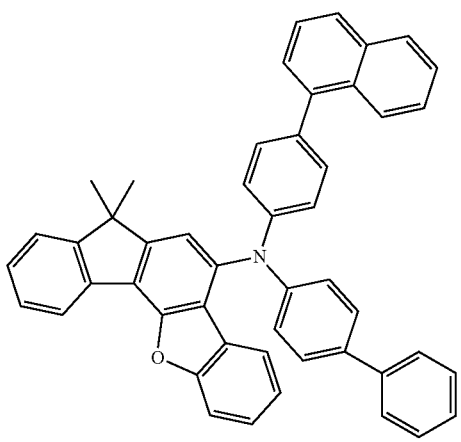
<Chemical Formula 87>
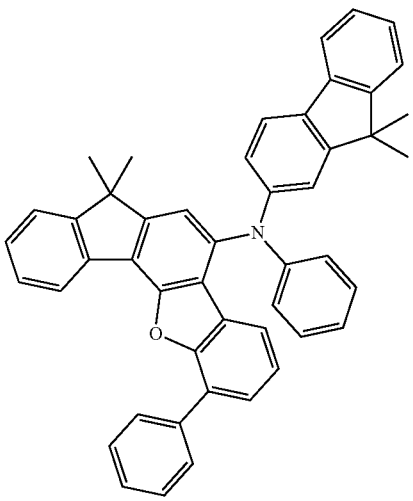
<Chemical Formula 88>
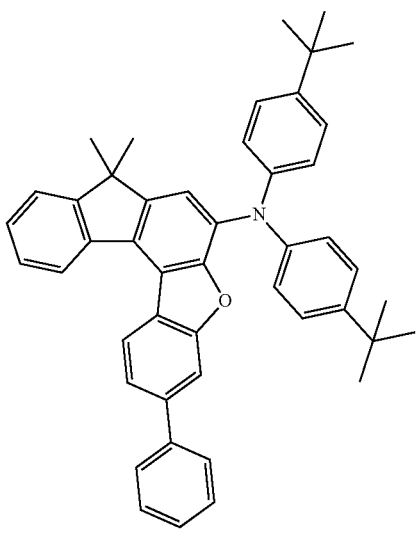

<Chemical Formula 89>
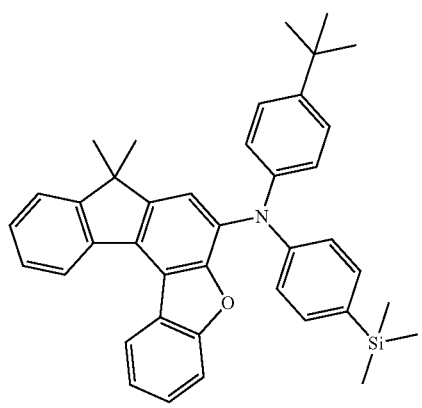
<Chemical Formula 90>
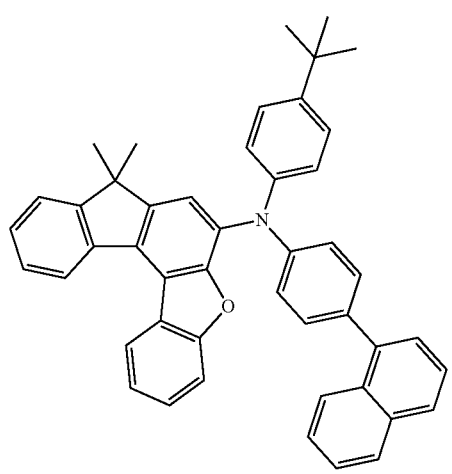
<Chemical Formula 91>
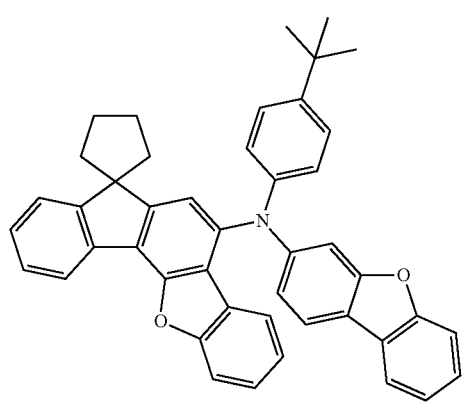
<Chemical Formula 92>
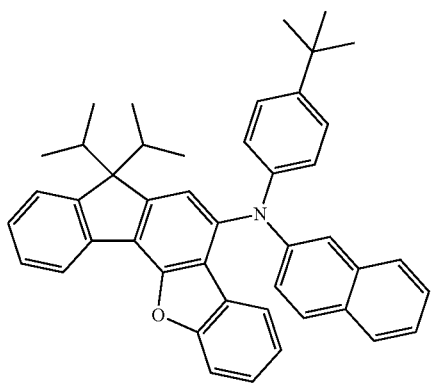
<Chemical Formula 93>
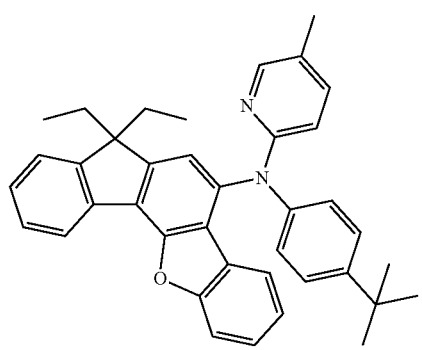
<Chemical Formula 94>
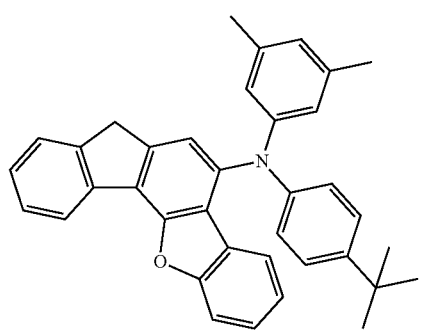
<Chemical Formula 95>
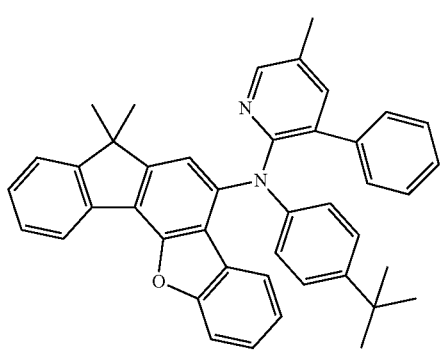

<Chemical Formula 96>
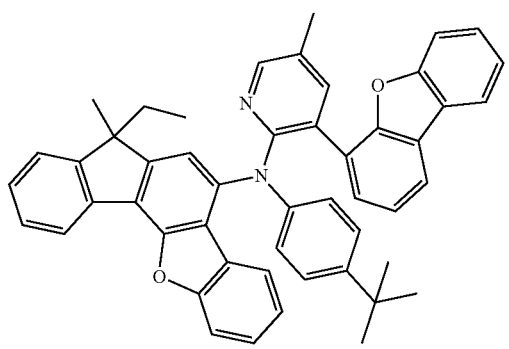
<Chemical Formula 97>
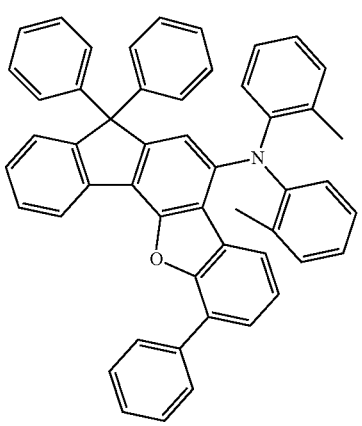
<Chemical Formula 98>
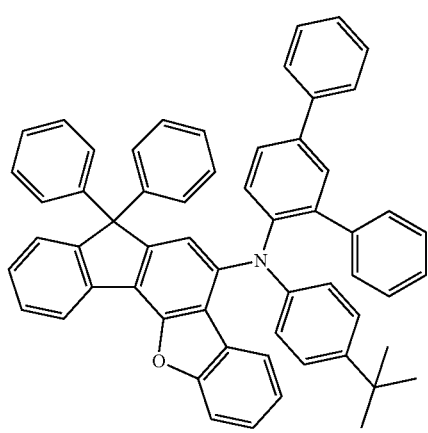
<Chemical Formula 99>
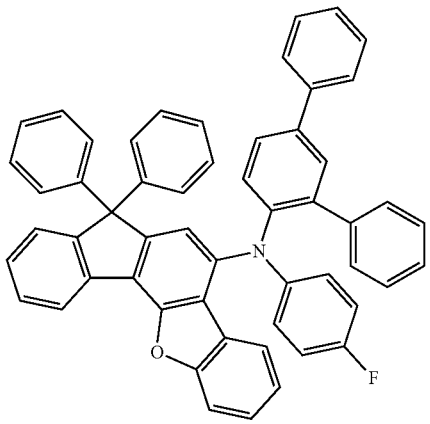
<Chemical Formula 100>
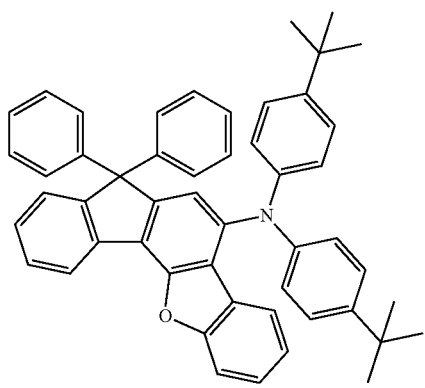
<Chemical Formula 101>
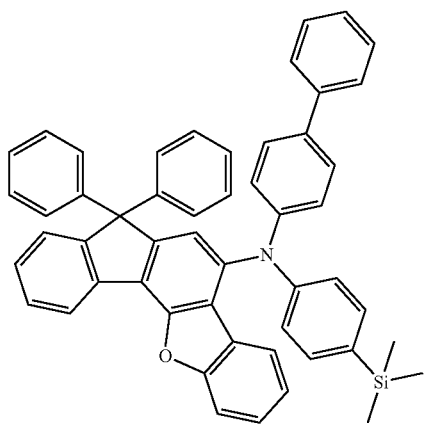

<Chemical Formula 102>
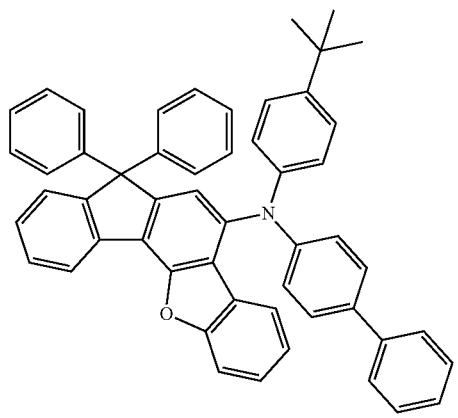
<Chemical Formula 103>
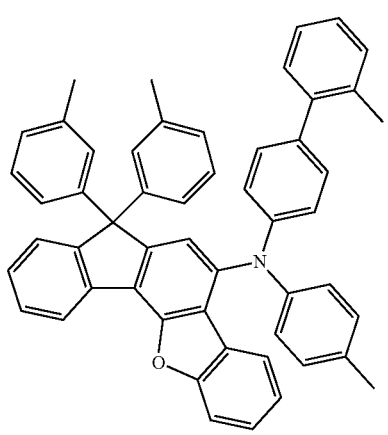
<Chemical Formula 104>
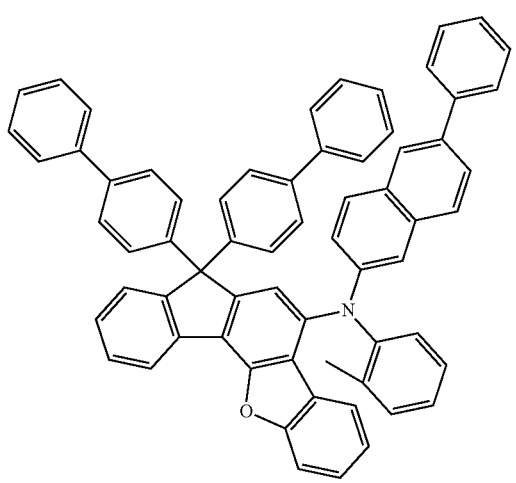
<Chemical Formula 105>
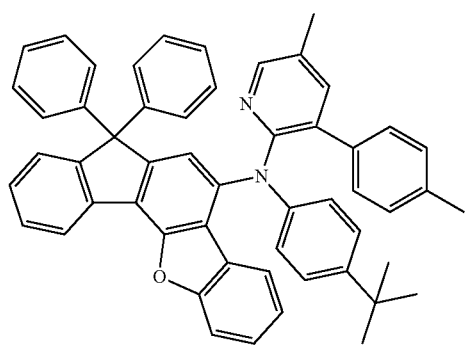
<Chemical Formula 106>
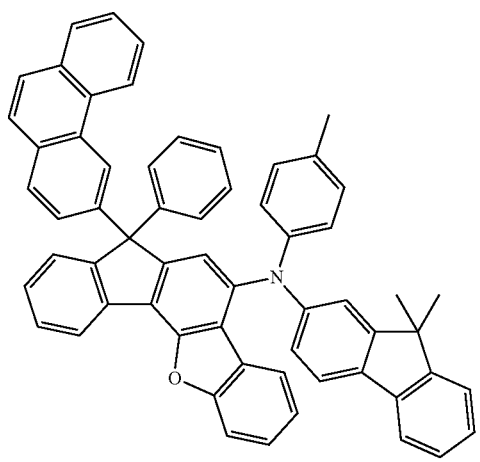
<Chemical Formula 107>
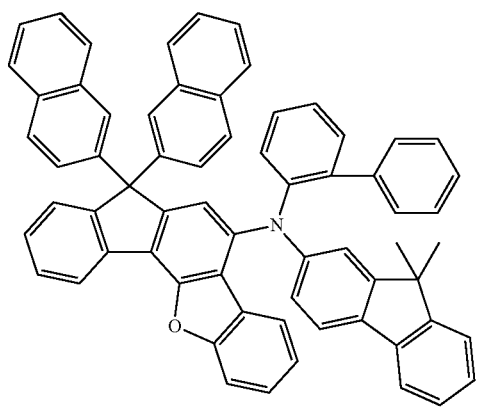

<Chemical Formula 108>
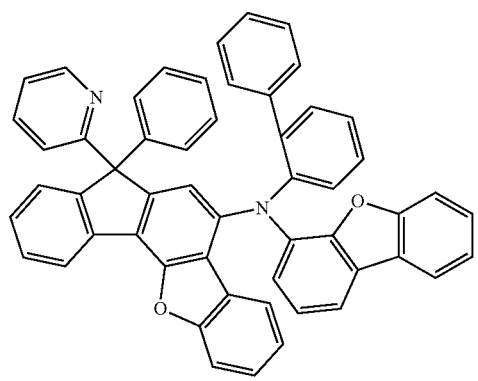
<Chemical Formula 109>
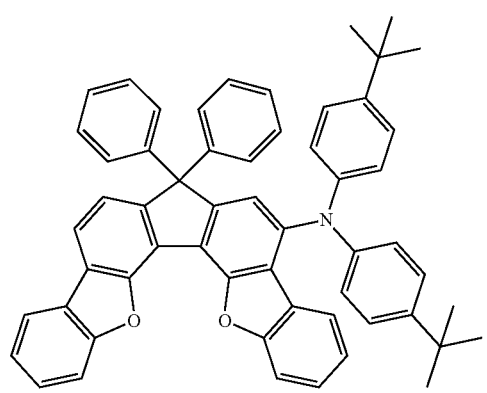
<Chemical Formula 110>
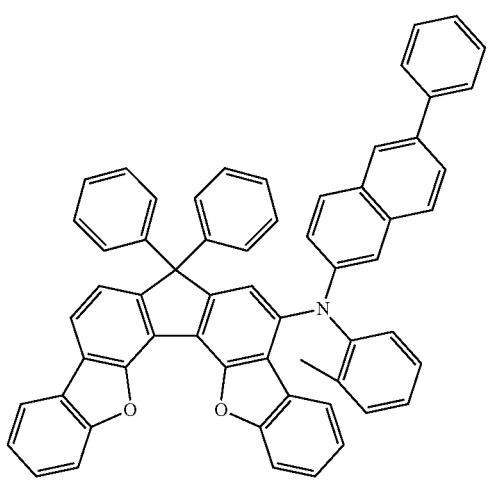
<Chemical Formula 111>
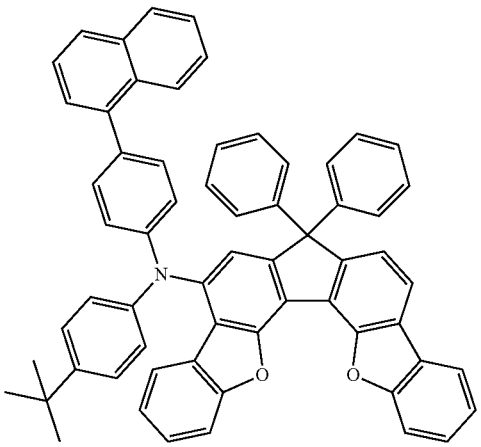
<Chemical Formula 112>
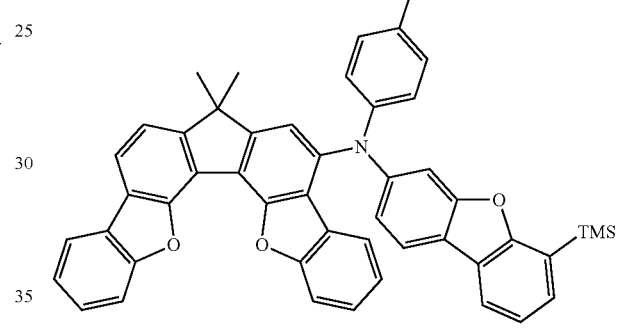
<Chemical Formula 113>
<Chemical Formula 114>
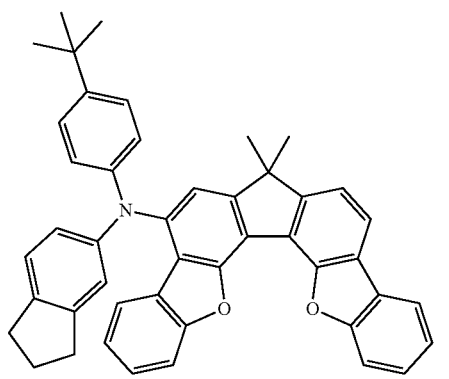

<Chemical Formula 115>
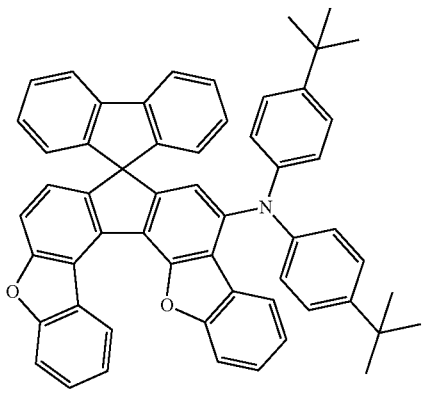
<Chemical Formula 116>
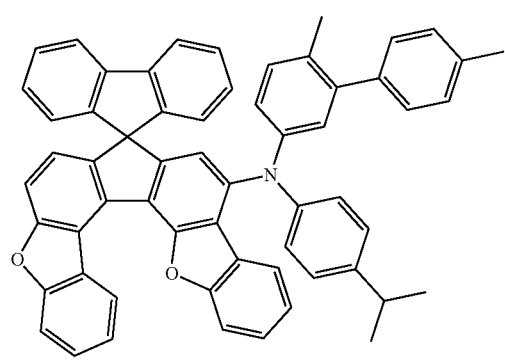
<Chemical Formula 117>
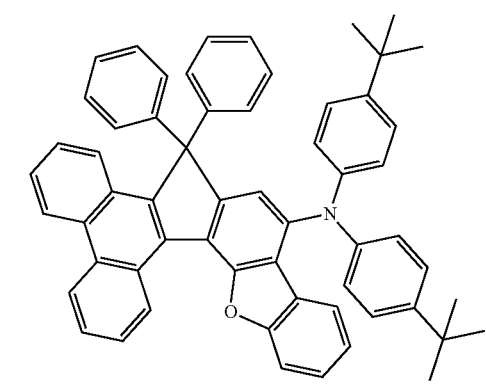
<Chemical Formula 118>
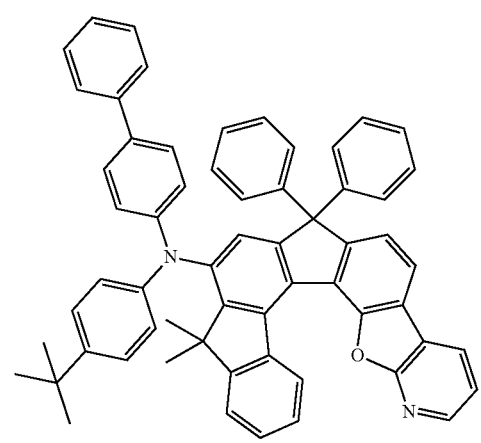
<Chemical Formula 119>
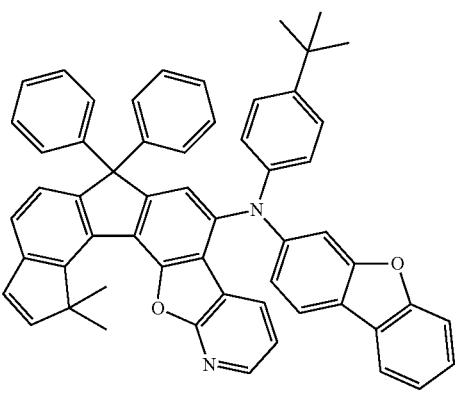
<Chemical Formula 120>
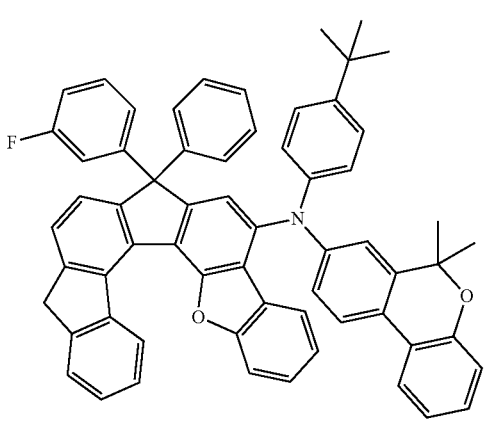
<Chemical Formula 121>
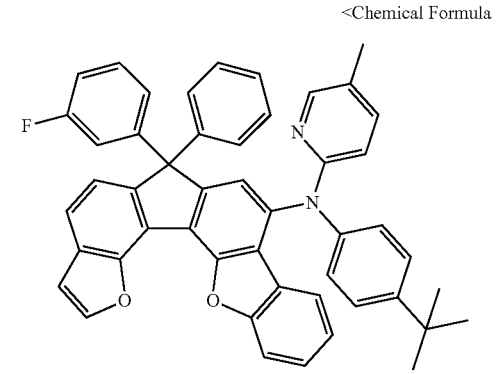
<Chemical Formula 122>
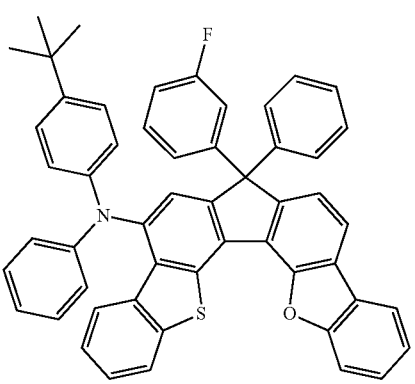

<Chemical Formula 123>
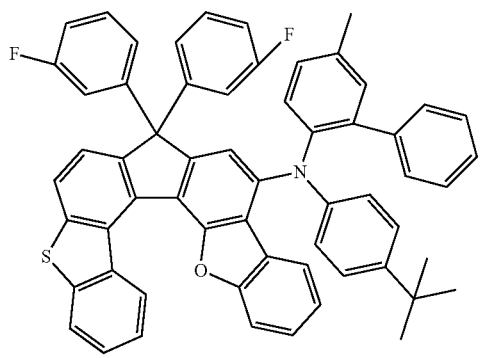
<Chemical Formula 124>
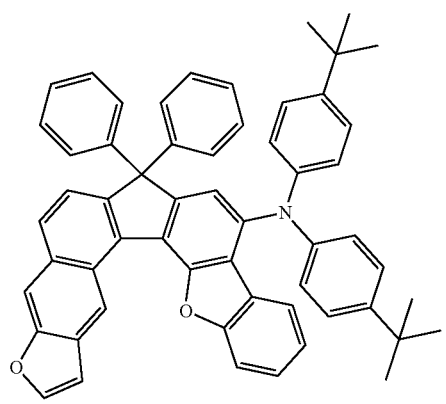
<Chemical Formula 125>
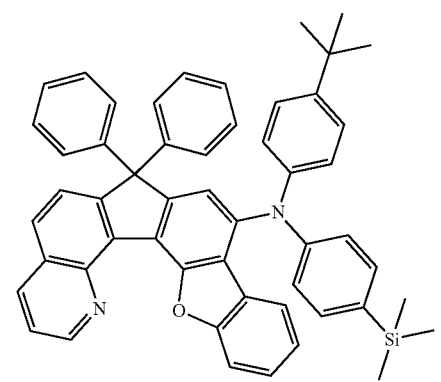
<Chemical Formula 126>
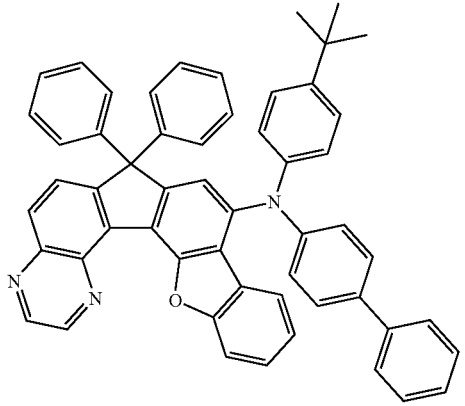
<Chemical Formula 127>
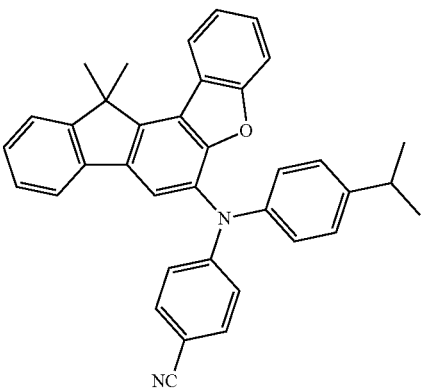
<Chemical Formula 128>
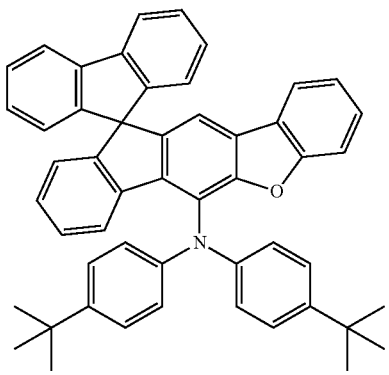
<Chemical Formula 129>
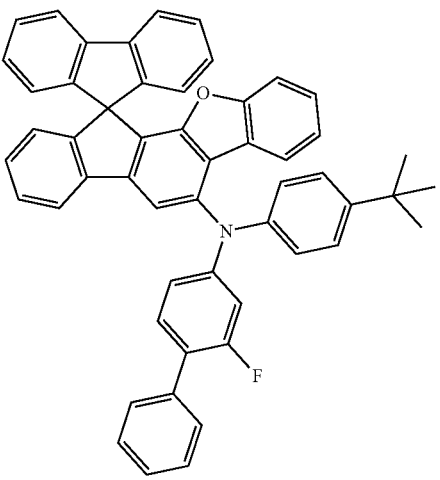

<Chemical Formula 130>
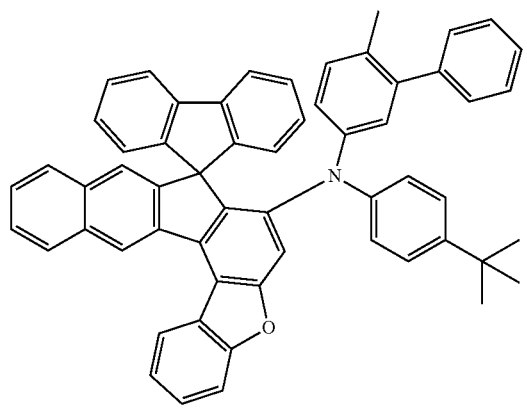
<Chemical Formula 131>
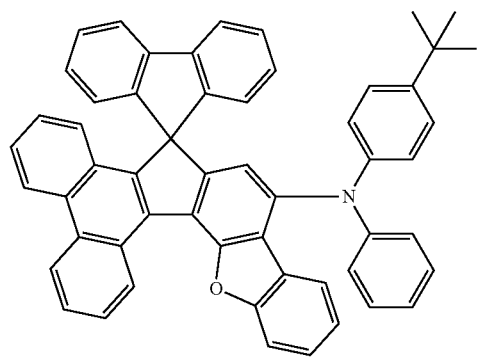
<Chemical Formula 132>
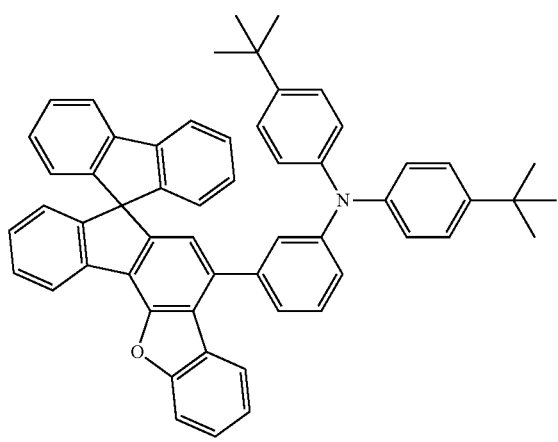
<Chemical Formula 133>
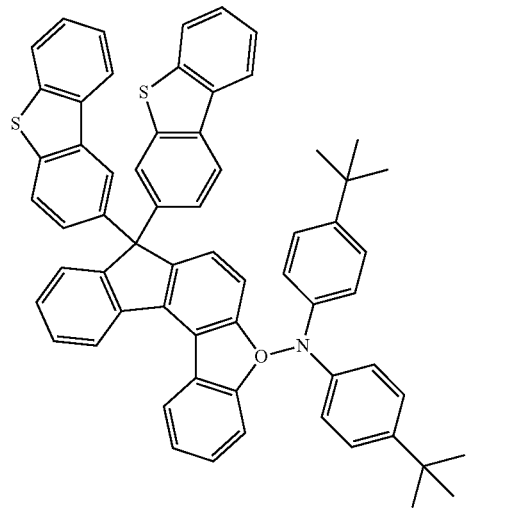
<Chemical Formula 134>
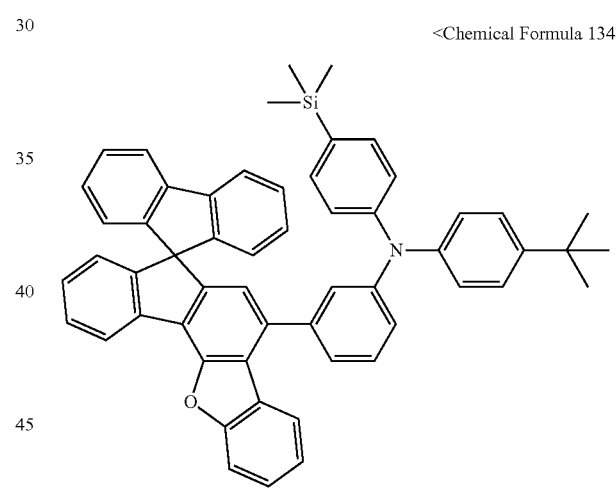
<Chemical Formula 135>
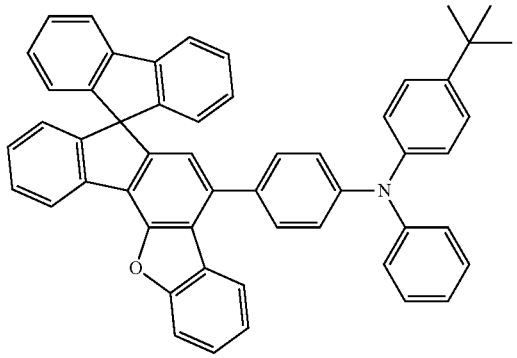

<Chemical Formula 136>
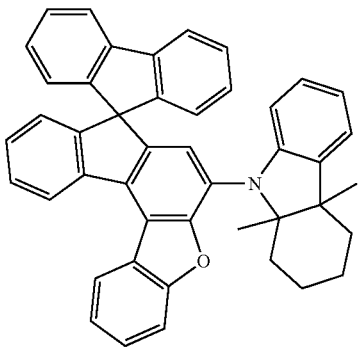
<Chemical Formula 137>
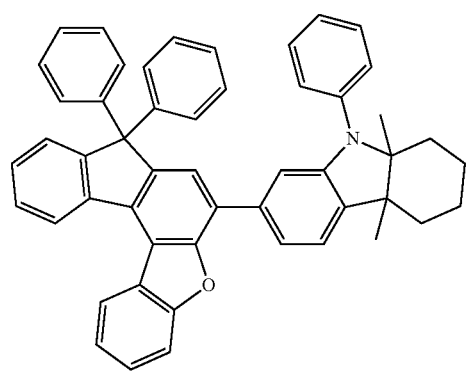
<Chemical Formula 138>
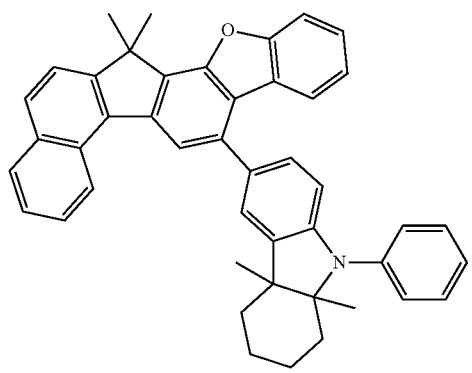
<Chemical Formula 139>
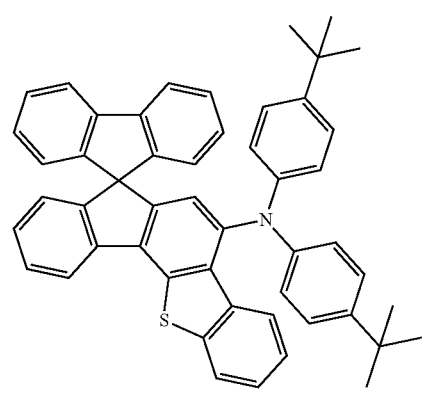
<Chemical Formula 140>
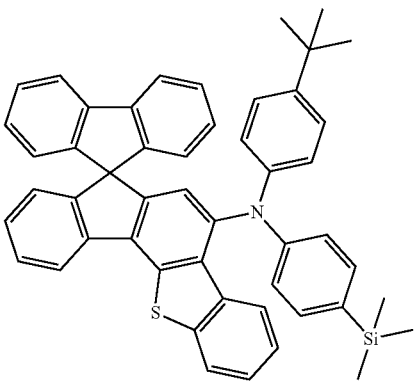
<Chemical Formula 141>
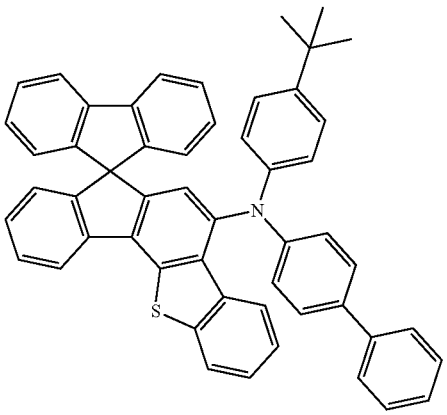
<Chemical Formula 142>
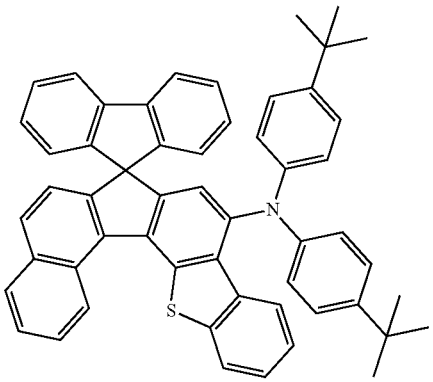
<Chemical Formula 143>
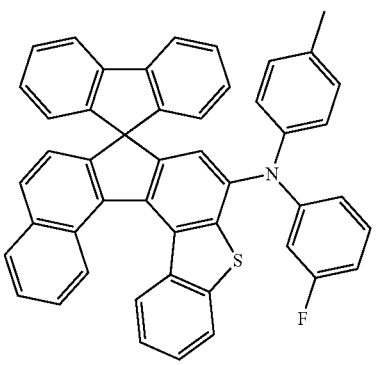

<Chemical Formula 144>
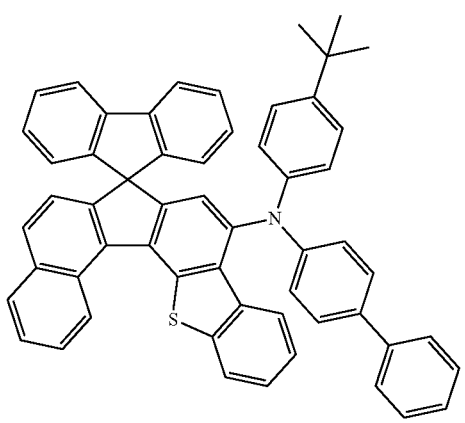
<Chemical Formula 145>
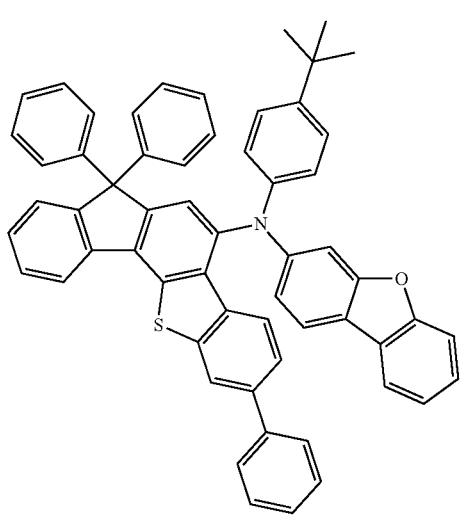
<Chemical Formula 146>
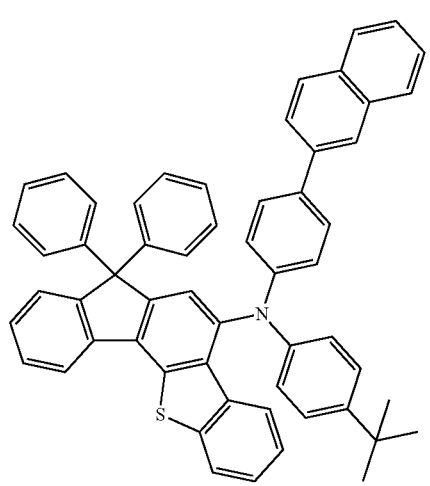
<Chemical Formula 147>
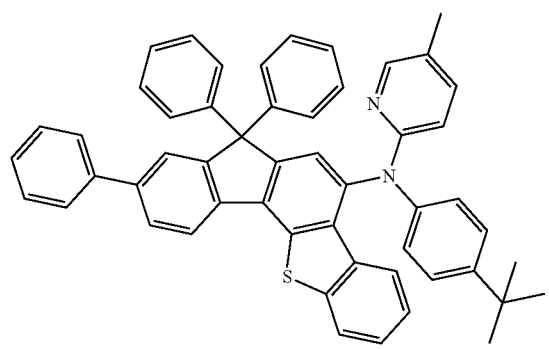
<Chemical Formula 148>
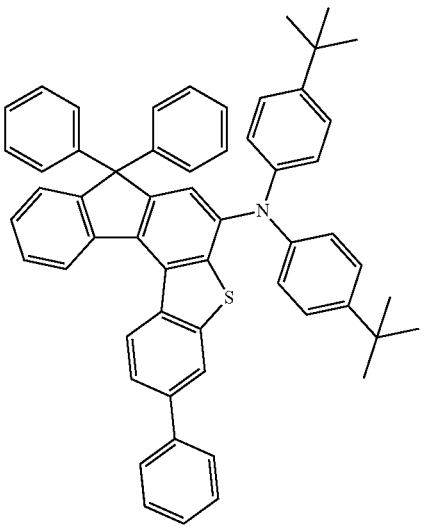
<Chemical Formula 149>
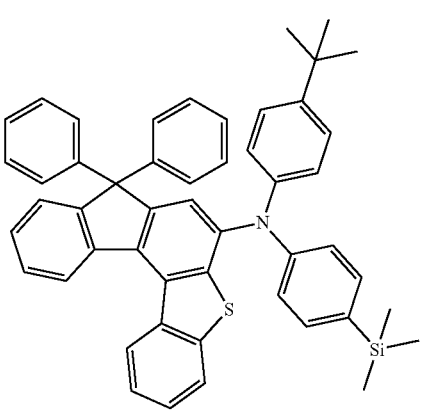

<Chemical Formula 150>
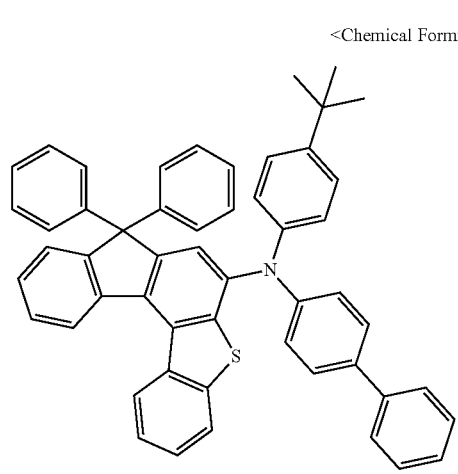
<Chemical Formula 151>
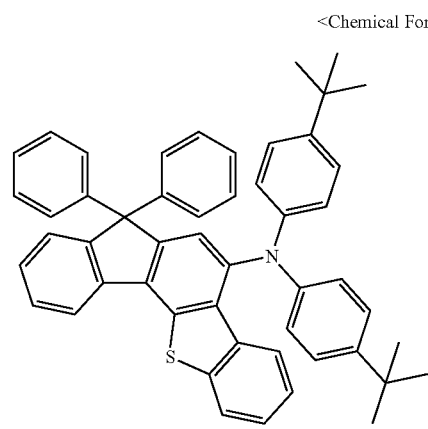
<Chemical Formula 152>
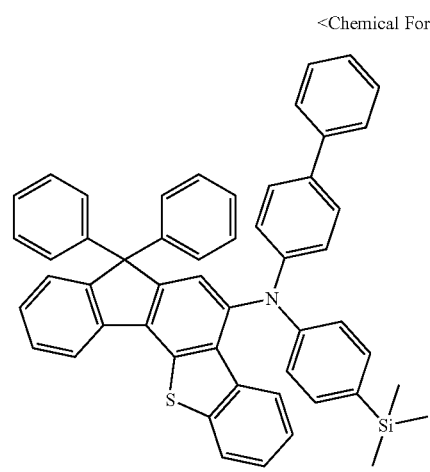
<Chemical Formula 153>
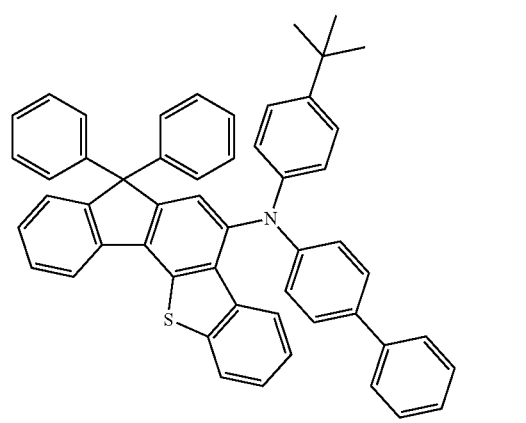
<Chemical Formula 154>
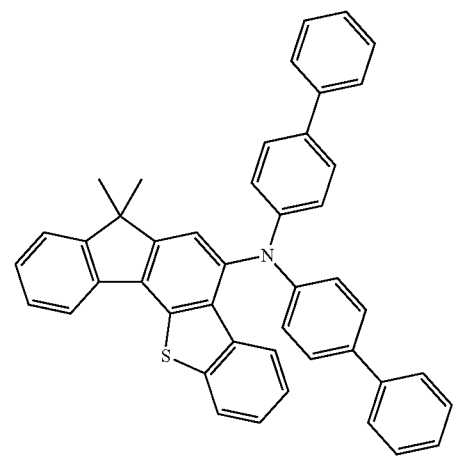
<Chemical Formula 155>
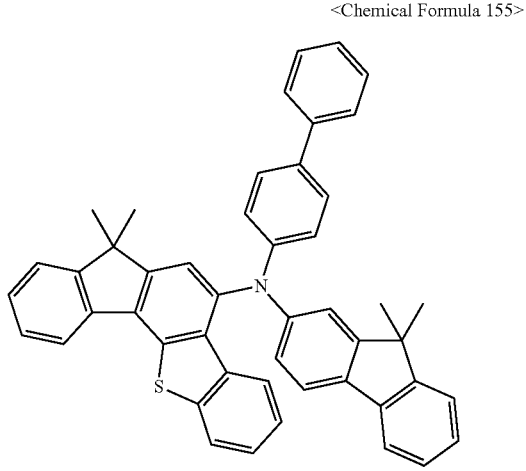

<Chemical Formula 156>
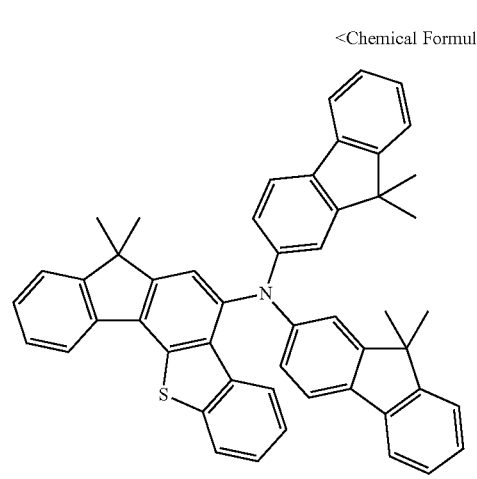
<Chemical Formula 157>
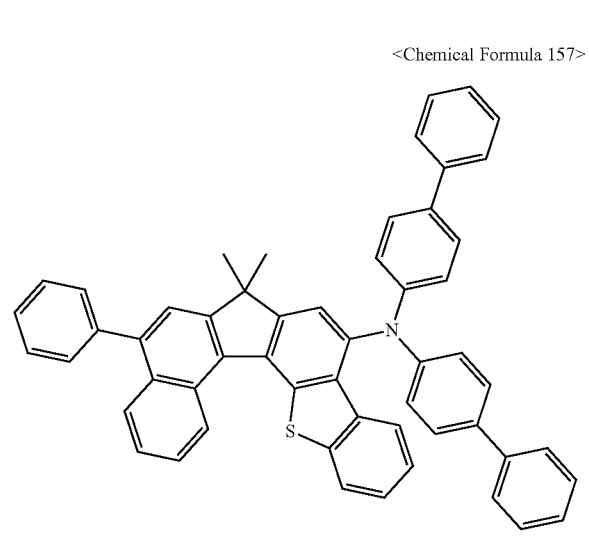
<Chemical Formula 158>
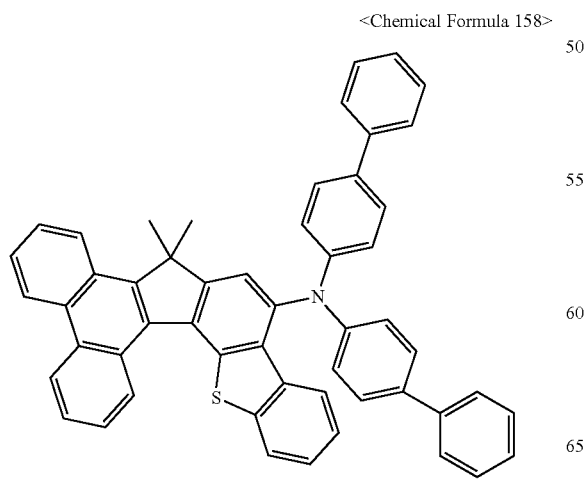
<Chemical Formula 159>
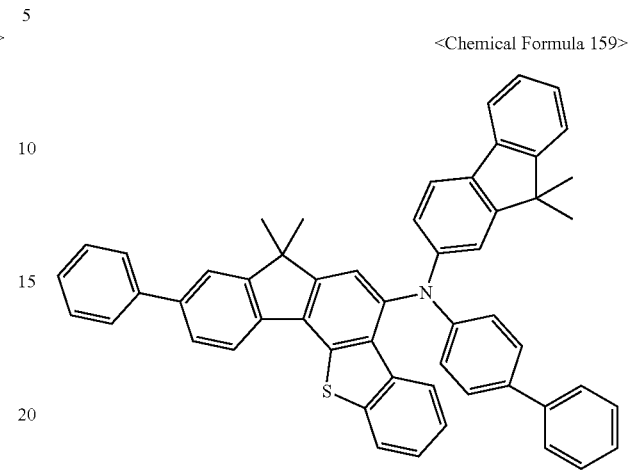
<Chemical Formula 160>
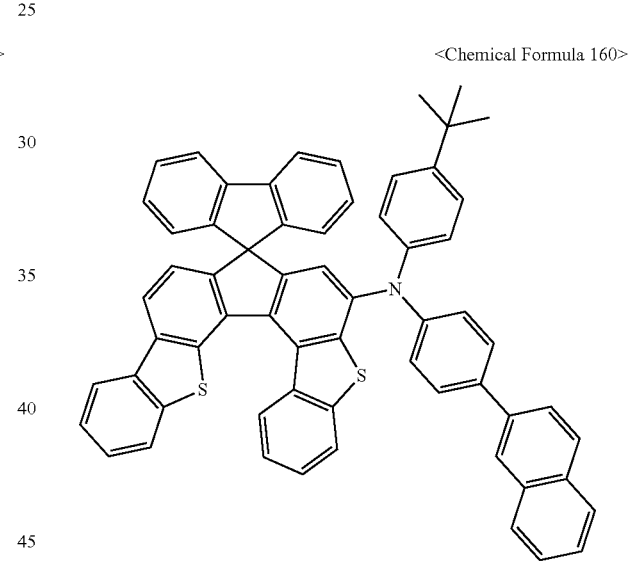
<Chemical Formula 161>
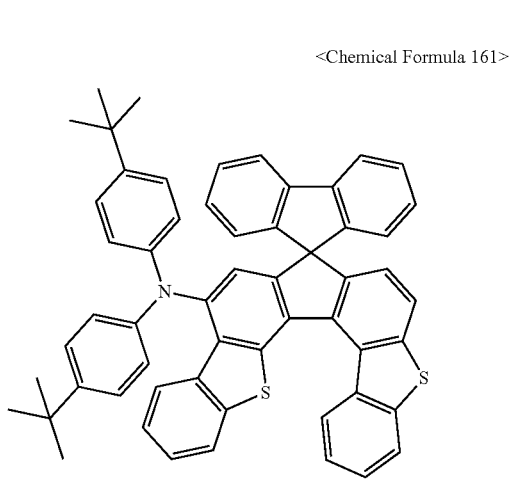

<Chemical Formula 162>

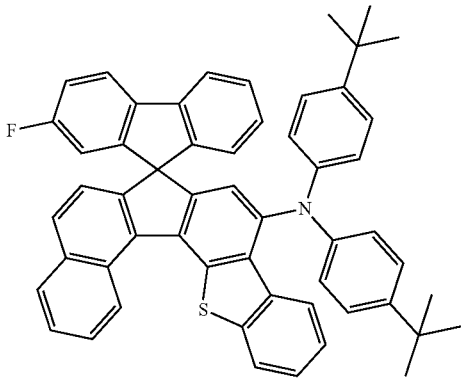

<Chemical Formula 163>

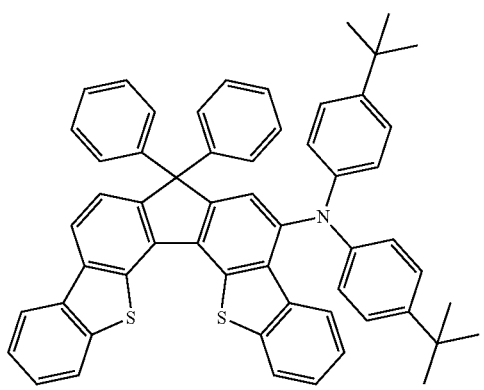

<Chemical Formula 164>

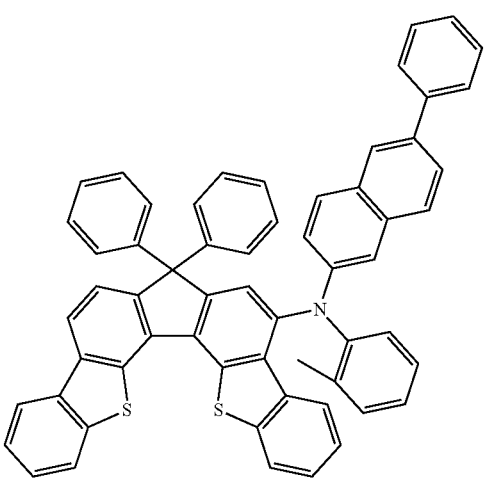

<Chemical Formula 165>

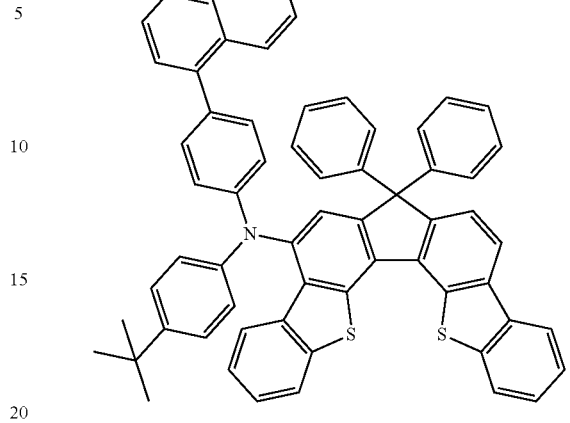

In accordance with a preferred aspect thereof, the present disclosure addresses an organic light-emitting diode, comprising a first electrode; a second electrode facing the first electrode; and an organic layer interposed between the first electrode and the second electrode, wherein the organic layer comprises at least one of the amine compounds of the present disclosure.

As used herein, the expression "(the organic layer) . . . comprising at least one compound" is construed to mean that the organic layer may include one or two or more different compounds that fall within the scope of the present disclosure.

The organic layer comprising the compound of the present disclosure may include at least one selected from among a holt injection layer, a hole transport layer, an electron-blocking layer, a light-emitting layer, an electron transport layer, and an electron injection layer. In this regard, the organic layer interposed between the first electrode and the second electrode may be a hole injection layer or a hole transport layer wherein the amine compound may be used in the hole injection layer or the hole transport layer. Alternatively, the organic layer interposed between the first electrode and the second electrode may be an electron-blocking layer wherein the amine compound may be used in the electron-blocking layer.

In addition to the amine compound of Chemical A or B, other compounds, for example, electron-donating molecules that have low ionization potentials can be used. They may be tri- or tetraamine derivatives based on a triphenyl amine skeleton, as exemplified by N,N'-bis(3-methylphenyl)-N,N'-diphenyl-[1,1-biphenyl]-4,4'-diamine(TPD) or N,N'-di (naphthalen-1-yl)-N,N'-diphenylbenzidine (a-NPD).

Under the hole transport layer, a hole injection layer (HIL) may be further depositved. In addition to the amine compound of Chemical Formula A or B, any material may be available for the HIL without particular limitations, as long as it is typically used in the art. Examples include HATCN (Hexaazatriphenylenehexacarbonitrile), CuPc(copperphthalocyanine), and a stabust amine, such as TCTA (4,4',4"-tri (N-carbazolyl)triphenyl-amine) or m-MTDATA (4,4',4"-tris-(3-methylphenylphenyl amino)triphenylamine).

In addition, the light-emitting layer may consist of a host and a dopant. So long as it is applicable for an organic light-emitting layer, any host or dopant may be used without limitations.

In some embodiments of the present disclosure, the content of the dopant in the light-emitting layer may range from about 0.01 to 20 parts by weight based on 100 parts by weight of the host, but is not limited thereto.

So long as it functions to stably transport the electrons from the cathode, any known material may be used for the electron transport layer. Examples of the known electron transport material include quinoline derivatives, particularly tris(8-quinolinolate)aluminum (Alq3), Liq, TAZ, BAlq, beryllium bis(benzoquinolin-10-olate)(Bebq2), compound 201, compound 202, BCP, and the oxadiazole derivatives PBD, BMD, and BND, but are not limited thereto.

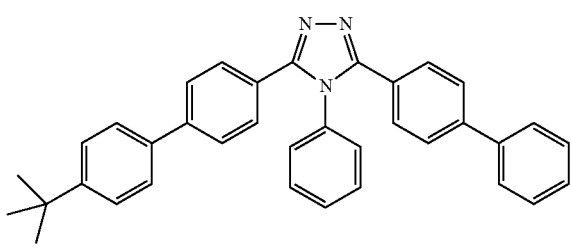

TAZ

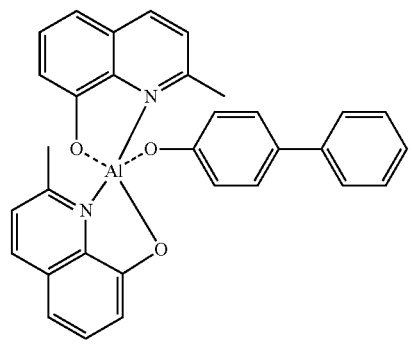

BAlq

<Compound 201>

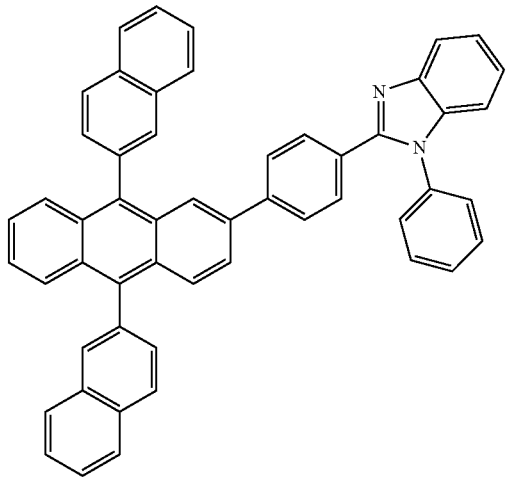

<Compound 202>

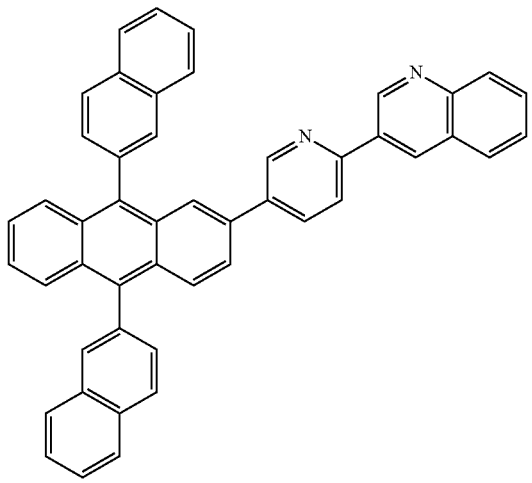

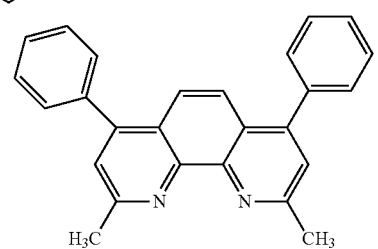

BCP

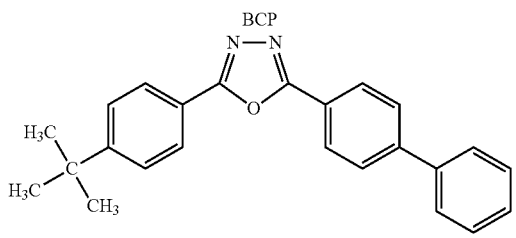

PBD

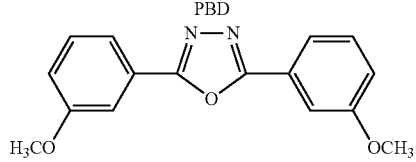

BMD

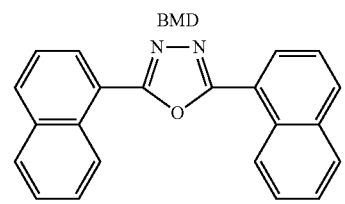

BND

An electron injection layer (EIL) that is adapted to facilitate the injection of electrons from the cathode so as to improve power efficiency may be positioned on the electron transport layer in the organic light-emitting diode of the present disclosure. Any known material may be available for forming the electron injection layer, without particular limitations, as long as it is usually used in the art.

By way of example, the material for the electron injection layer may be CsF, NaF, LiF, NaCl, Li$_2$O, or BaO. The conditions for depositing the electron injection layer are dependent on the compound that is employed, but may fall within the range of conditions for the formation of the hole injection layer.

The electron injection layer may range in thickness from about 1 Å to about 100 Å, and particularly from about 3 Å to about 90 Å. Given this thickness range, the electron injection layer can exhibit satisfactory electron injection properties without an actual increase in driving voltage.

Further, one or more layers selected from among a hole injection layer, a hole transport layer, an electron-blocking layer, a light-emitting layer, an electron transport layer, and an electron injection layer may be deposited using a deposition process or a solution process.

Here, the deposition process refers to a process by which a material is vaporized in a vacuum or at a low pressure and deposited to form a layer, and the solution process means a method in which a material is dissolved in a solvent and applied for the formation of a thin film by means of inkjet printing, roll-to-roll coating, screen printing, spray coating, dip coating, spin coating, etc.

The cathode may be made of a metal or metal alloy such as lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be employed to form a transparent cathode for a top-emitting organic light-emitting diode.

In another embodiment, the light-emitting diode of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting diode of the present disclosure may have a multilayer structure in which the additional blue, green, and/or red light-emitting layer may be made of a fluorescent or phosphorescent material.

Also, the organic light-emitting diode of the present disclosure may be applied to a device selected from among flat display devices, flexible display devices, monochrome or white flat illumination devices, and monochrome or white flexible illumination devices.

FIG. 1 is a schematic cross-sectional view of the structure of an organic light-emitting diode according to some embodiments of the present disclosure. As shown in FIG. 1, the organic light-emitting diode comprises an anode 20, a hole transport layer 40, a light-emitting layer 50 composed of a host and a dopant, an electron transport layer 60, and a cathode 80, sequentially, that is, the organic light-emitting diode comprises an anode as the first electrode and a cathode as the second electrode, with a hole transport layer 40 and an electron transport layer 60 interposed between the anode 20 and a light-emitting layer 50 and between the light-emitting layer 50 and the cathode 80, respectively.

In addition, the organic light-emitting diode according to an embodiment of the present disclosure comprises a hole injection layer 30 between the anode 20 and the hole transport layer 40, and an electron injection layer 70 between the electron transport layer 60 and the cathode 80. Optionally, one or two intermediate layers may be further formed.

Reference is made to FIG. 1 with regard to the fabrication of the organic light-emitting diode of the present disclosure. First, a substrate 10 is coated with an anode electrode material to form an anode 20. So long as it is used in a typical organic EL device, any substrate may be used as the substrate 10. Preferable is an organic substrate or a transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO) may be used owing to their high transparency and electroconductivity.

A hole injection layer material is applied on the anode electrode 20 by thermal deposition in a vacuum or by spin coating to form a hole injection layer 30. Subsequently, thermal deposition in a vacuum or spin coating of a hole transport layer material may also be conducted to form a hole transport layer 40 on the hole injection layer 30.

Then, an organic light-emitting layer 50 may be deposited on the hole transport layer 40, optionally followed by depositing a hole barrier layer (not shown) on the organic light-emitting layer 50 by a vacuum deposition process or a spin coating process.

When holes traverse the organic light-emitting layer and are introduced into the cathode, the diode becomes poor in efficiency and lifetime. Formed of a material with a low HOMO (Highest Occupied Molecular Orbital) level, the hole barrier layer serves to prevent the introduction of holes into the cathode. Any material that has a higher ionization potential than the light-emitting compound and is also able to carry electrons may be used for the hole barrier layer without limitations. Representative among hole barrier materials are BAlq, BCP, and TPBI.

Using a vacuum deposition process or a spin-coating process, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL diode. Here, the cathode may be made of lithium (Li), magnesium (Mg), aluminum (Al), aluminu-lithium (Al—Li), calcium (Ca), magnesium-indium (Mg—In), or magnesium-silver (Mg—Ag). For a top-emitting OLED, a transparent cathode made of ITO or IZO may be employed.

In some embodiments of the present disclosure, the light-emitting layer particularly ranges in thickness from 50 to 2,000 Å.

Figure 2:
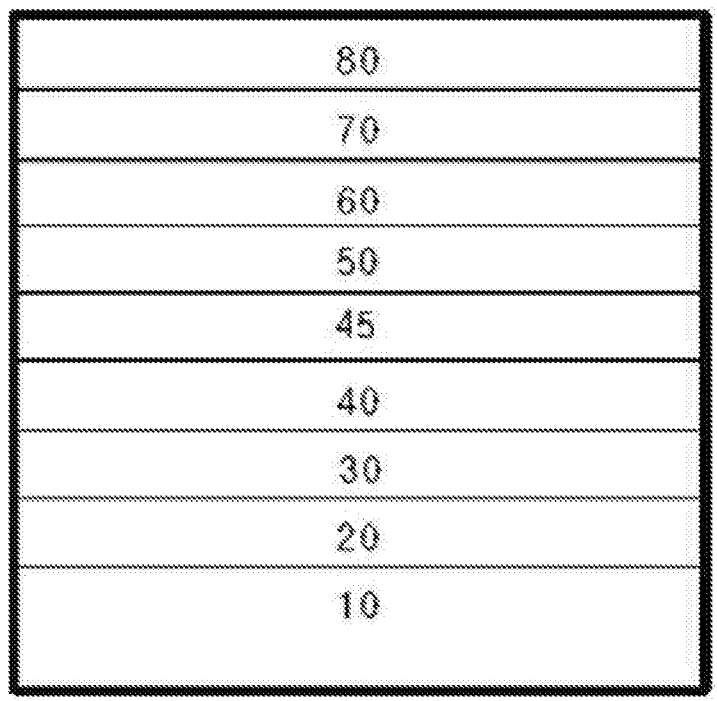
FIG. 2 is a schematic cross-sectional view of the structure of an organic light-emitting diode according to another embodiment of the present disclosure.

FIG. 2 is a schematic cross-sectional view of the structure of an organic light-emitting diode according to some embodiments of the present disclosure. As shown in FIG. 2, the organic light-emitting diode comprises an anode 20, a hole transport layer 40, an electron-blocking layer 45, a light-emitting layer 50 composed of a host and a dopant, an electron transport layer 60, and a cathode 80, sequentially, that is, the organic light-emitting diode comprises an anode as the first electrode and a cathode as the second electrode, with a hole transport layer 40 interposed between the anode 20 and a light-emitting layer 50, an electron transport layer 60 between the light-emitting layer 50 and the cathode 80, and an electron-blocking layer 45 between the electron transport layer 40 and the light-emitting layer 50. In addition, the organic light-emitting diode comprises a hole injection layer 30 between the anode 20 and the hole transport layer 40, and an electron injection layer 70 between the electron transport layer 60 and the cathode 80.

The organic light-emitting diode and fabrication according to FIG. 2 is the same in that according to FIG. 1, with the exception that an electron-blocking layer (EBL) material represented by Chemical Formula A or B is deposited on the hole transport layer 40 by thermal deposition in a vacuum or by spin coating to form an electron-blocking layer 45, followed by sequentially depositing a light-emitting layer 50, an electron transport layer 60, an electron injection layer 70, and a cathode on the electron-blocking layer 45.

Together with the organic compound of the present disclosure, a compound known in the art may be used for the electron-blocking layer 45.

A better understanding of the light-emitting diode according to the present disclosure may be obtained through the following examples which are set forth to illustrate, but are not to be construed as the limit of the present disclosure.

EXAMPLES

Synthesis Example 1: Synthesis of Compound of Chemical Formula 2

Synthesis Example 1-(1): Synthesis of Intermediate 1-a

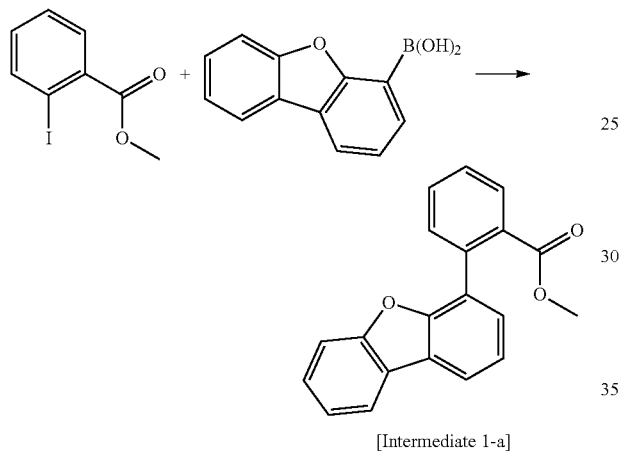

[Intermediate 1-a]

In a 500-mL round-bottom flask reactor, methyl 5-iodo-2-iodobenzoate (19.1 g, 73 mmol), 4-dibenzofuran boronic acid (18.7 g, 88 mmol), tetrakis(triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford [Intermediate 1-a]. (9.5 g, 43%).

Synthesis Example 1-(2): Synthesis of [Intermediate 1-b]

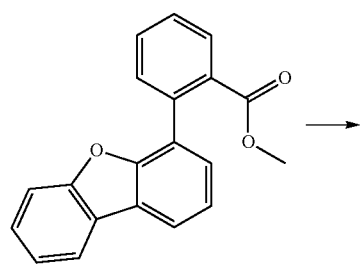

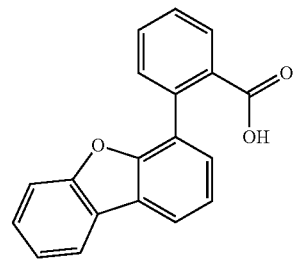

[Intermediate 1-b]

In a 500-mL round-bottom flask reactor, [Intermediate 1-a](13.6 g, 45 mmol), sodium hydroxide (2.14 g, 54 mmol) and ethanol (170 ml) were stirred together for 48 hrs under reflux. After the completion of the reaction was confirmed by thin layer chromatography, the reaction mixture was cooled to room temperature. The chilled solution was acidified with drops of 2-N HCl, followed by stirring for 30 min. The solid thus formed was filtered, and recrystallized in dichloromethane and n-hexane to afford [Intermediate 1-b]. (11.4 g, 88%)

Synthesis Example 1-(3): Synthesis of [Intermediate 1-c]

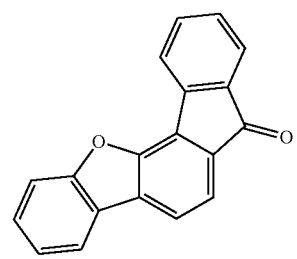

[Intermediate 1-c]

In a 250-mL round-bottom flask reactor, [Intermediate 1-b](11.2 g, 39 mmol) and methanesulfonic acid (145 ml) were stirred together for 3 hrs at 80° C. After the completion of the reaction was confirmed by thin layer chromatography, the reaction mixture was cooled to room temperature and dropwise added to ice water (150 ml). After stirring for 30 min, the solid thus formed was filtered and washed with water and methanol to afford [Intermediate 1-c]. (8.7 g, 83%)

Synthesis Example 1-(4): Synthesis of
[Intermediate 1-d]

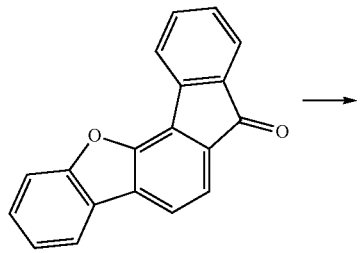

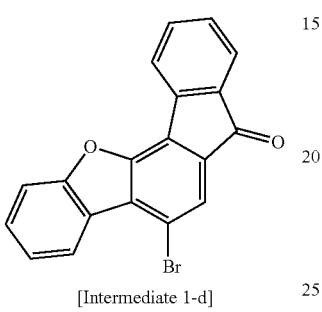

[Intermediate 1-d]

In a 1-L round-bottom flask reactor, [Intermediate 1-c] (8.6 g, 32 mmol> and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered, and washed with acetone. Recrystallization in monochlorobenzene afforded [Intermediate 1-d]. (8.7 g, 78%)

Synthesis Example 1-(5): Synthesis of
[Intermediate 1-e]

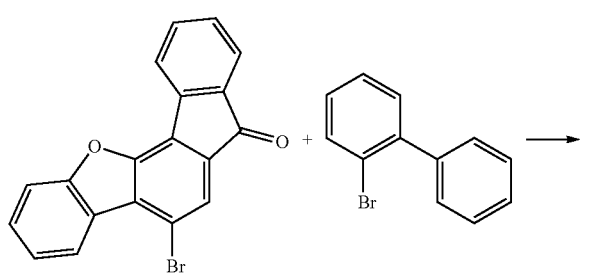

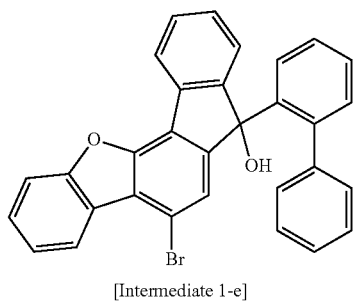

[Intermediate 1-e]

In a 250-ml round-bottom flask reactor, 2-bromobiphenyl (8.4 g, 0.036 mol) and tetrahydrofuran (110 ml) were chilled at −78° C. under a nitrogen atmosphere. At the same temperature, n-butyl lithium (19.3 ml, 0.031 mol) was dropwise added to the reaction solution which was then stirred for 2 hrs. Thereafter, [Intermediate 1-d](8.4 g, 0.024 mol) was added little by little to the reaction solution, and stirred at room temperature. When the reaction mixture started to change color, the reaction was monitored via thin layer chromatography. After the reaction was stopped with water (50 ml), extraction was conducted with ethyl acetate and water. The organic layer was separated, concentrated in a vacuum, and recrystallized in acetonirile to afford [Intermediate 1-e] as a solid. (9.9 g, 82%)

Synthesis Example 1-(6): Synthesis of
[Intermediate 1-f]

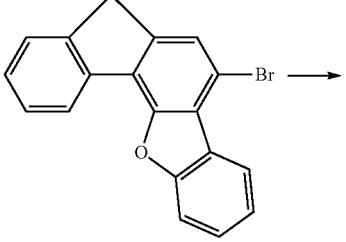

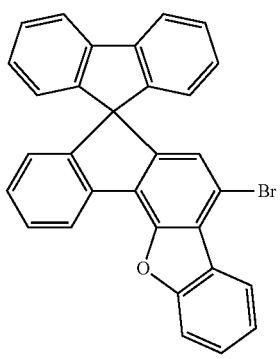

[Intermediate 1-f]

In a 250-ml round-bottom flask reactor, a mixture of <Intermediate 1-e>(9.6 g, 0.019 mol), acetic acid (120 ml), and sulfuric acid (2 ml) was stirred for 5 hrs under reflux. When a precipitate was formed, the completion of the reaction was monitored using thin layer chromatography. The reaction mixture was then cooled to room temperature and filtered. The filtrate was washed with H$_2$O and methanol and dissolved in monochlorobenzene. Following silica gel chromatography, the fraction was concentrated and cooled to room temperature to give [Intermediate 1-f]. (8.3 g, 90%>

Synthesis Example 1-(7): Synthesis of Compound of Chemical Formula 2

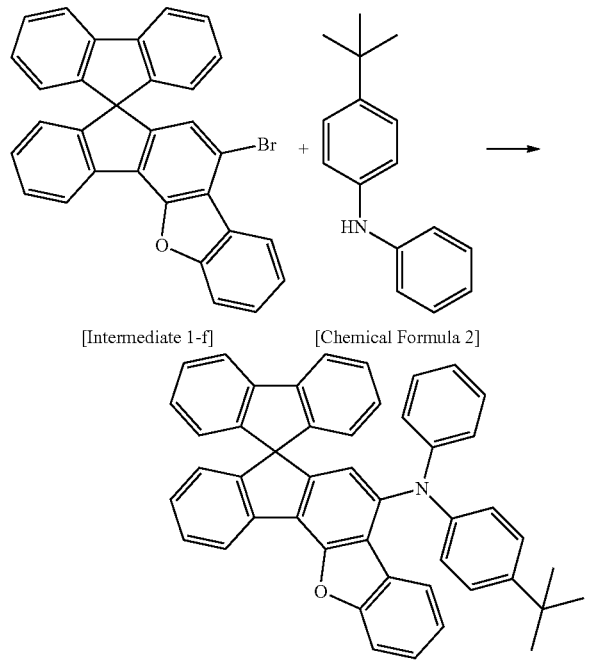

[Intermediate 1-f]    [Chemical Formula 2]

In a 250-ml round-bottom flask reactor, a mixture of [Intermediate 1-f] (4.4 g, 0.009 mol), (4-tert-butylphenyl)-phenylamine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) were stirred together for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 2 as a solid (3.3 g, 58%)

MS (MALDI-TOF): m/z 629.27 [M$^+$]

Synthesis Example 2: Synthesis of Compound of Chemical Formula 13

Synthesis Example 2-(1): Synthesis of [Intermediate 2-a]

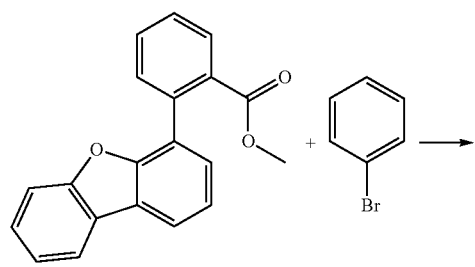

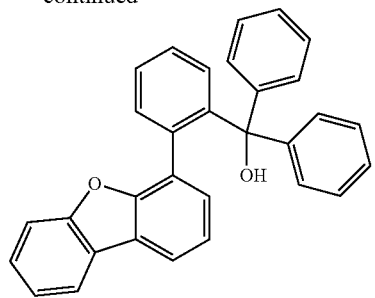

[Intermediate 2-a]

In a 2-L round-bottom flask reactor, bromobenzene (13.2 g, 83.97 mmol), tetrahydrofuran (250 ml) was stirred at a low temperature in a nitrogen atmosphere. At −78° C., n-butyl lithium (ca. 58 ml) was dropwise added over 2 hrs, followed by [Intermediate 1-a] (9.4 g 31.1 mmol). After completion of the reaction, the reaction mixture was stirred, together with water (100 ml), for 30 min, and extraction gave [Intermediate 2-a]. (3.2 g, 24%)

Synthesis Example 2-(2): Synthesis of [Intermediate 2-b]

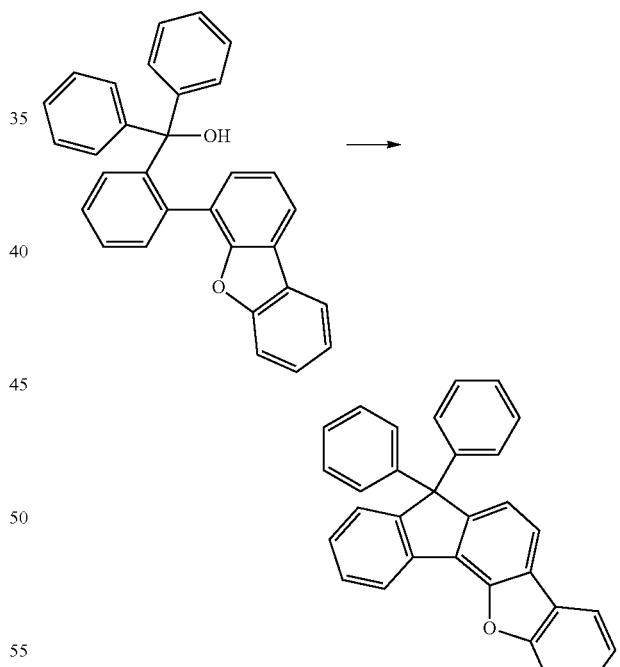

[Intermediate 2-b]

In a 2-L round-bottom flask reactor, [Intermediate 2-a] (55.0 g, 129 mmol), acetic acid (500 ml), and sulfuric acid (10 ml) were stirred together for 5 hrs under reflux. After completion of the reaction, the reaction mixture was cooled to room temperature, and the precipitates were filtered and washed with methanol to afford [Intermediate 2-b]. (50 g, 95%)

Synthesis Example 2-(3): Synthesis of [Intermediate 2-c]

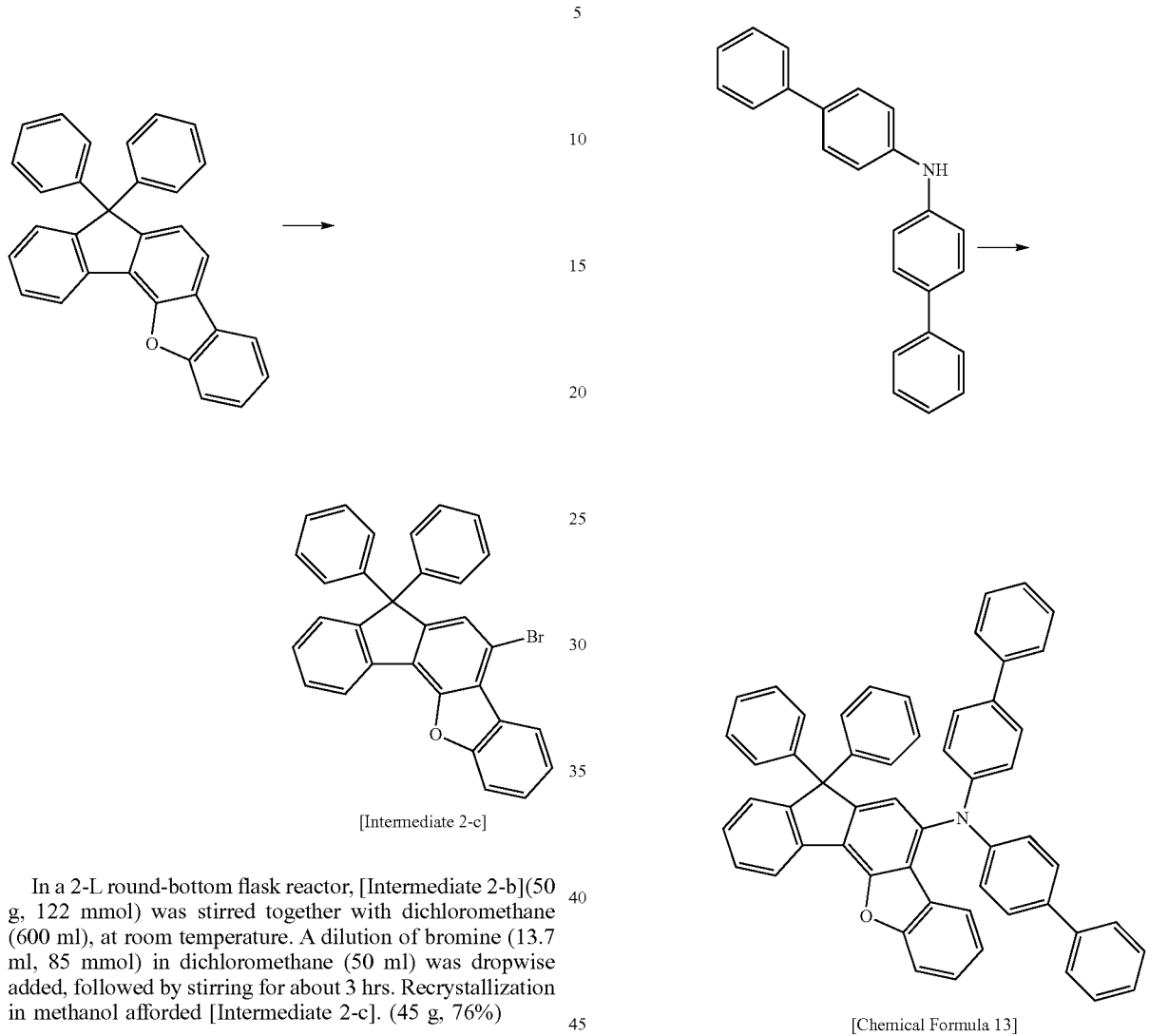

[Intermediate 2-c]

In a 2-L round-bottom flask reactor, [Intermediate 2-b](50 g, 122 mmol) was stirred together with dichloromethane (600 ml), at room temperature. A dilution of bromine (13.7 ml, 85 mmol) in dichloromethane (50 ml) was dropwise added, followed by stirring for about 3 hrs. Recrystallization in methanol afforded [Intermediate 2-c]. (45 g, 76%)

Synthesis Example 2-(4): Synthesis of Compound of [Chemical Formula 13]

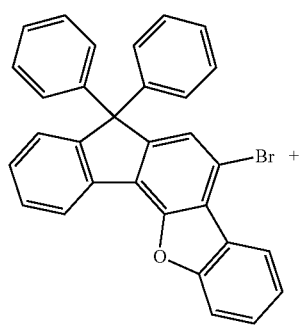

[Chemical Formula 13]

In a 250-ml round-bottom flask reactor, [Intermediate 2-c](4.3 g, 0.009 mol), bis-biphen-4-yl-amine (4.3 g, 0.013 mol), palladium(II) acetate (0.08 g, 0.4 mmol), sodium tert-butoxide (3.4 g, 0.035 mol), tert-butyl phosphine (0.07 g, 0.4 mmol), and toluene (60 ml) were stirred together for 2 hrs under reflux. After completion of the reaction, the reaction mixture was cooled to room temperature. The reaction mixture was extracted with dichloromethane and water. The organic layer thus formed was dried over magnesium sulfate and then concentrated in a vacuum. Following separation and purification via column chromatography, Recrystallization in dichloromethane and acetone afforded [Chemical Formula 13]. (2.6 g, 40%)

MS (MALDI-TOF): m/z 727.29[M$^+$]

Example 3: Synthesis of Compound of Chemical Formula 35

Synthesis Example 3-(1): Synthesis of [Intermediate 3-a]

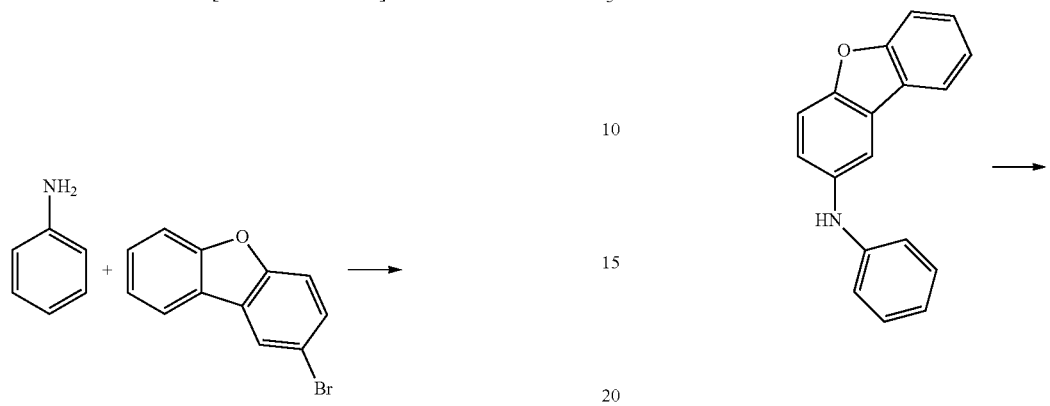

[Intermediate 3-a]

In a 500-ml round-bottom flask reactor, aniline (20 g, 215 mmol) 2-bromodibenzofuran (53.1 g, 215 mmol), bis-dibenzylidene acetone di palladium (3.9 g, 4 mmol), 2,2'-bis(diphenylphosphine)-1,1'-binaphthyl (1.2 g, 4 mmol), sodium tert-butoxide (41.3 g, 43 mmol), and toluene (200 ml) were stirred together under reflux. The reaction mixture was cooled to room temperature and washed with methanol. Recrystallization in dichloromethane and methane gave [Intermediate 3-a]. (40 g, 72%)

Synthesis Example 3-(2): Synthesis of Compound of [Chemical Formula 35]

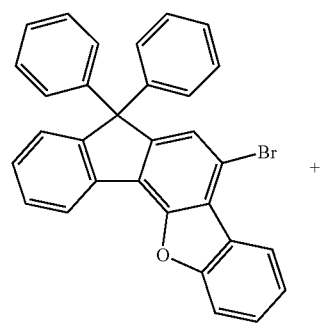

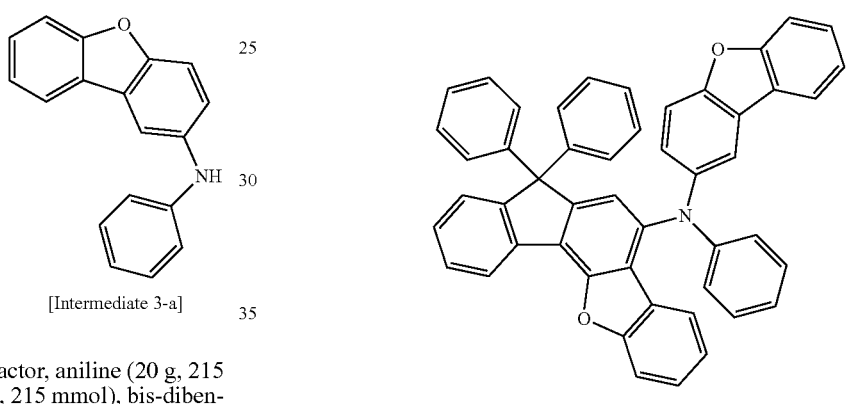

[Chemical Formula 35]

The compound of [Chemical Formula 35] was synthesized in the same manner as in Synthesis Example 2-(4), with the exception that [Intermediate 3-a] was used instead of bis-biphen-4-yl-amine. (yield 66%)

MS (MALDI-TOF): m/z 665.24 [M$^+$]

Example 4: Synthesis of Compound of Chemical Formula 37

Synthesis Example 4-(1): Synthesis of Compound of [Chemical Formula 37]

The compound of [Chemical Formula 37] was synthesized in the same manner as in Synthesis Examples 1-(1) and 1-(7), with the exception that 1-dibenzofuran boronic acid and bis(4-tert-butylphenyl)amine were used instead of 4-dibenzofuran boronic acid of Synthesis Example 1-(1) and (4-tert-butylphenyl)-phenyl amine of Synthesis Example 1-(7), respectively. (yield 55%) MS (MALDI-TOF): m/z 685.33 [M$^+$]

Example 5: Synthesis of Compound of Chemical Formula 75

Synthesis Example 5-(1): Synthesis of [Intermediate 5-a]

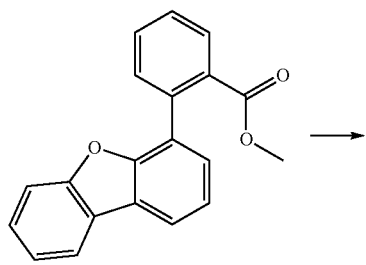

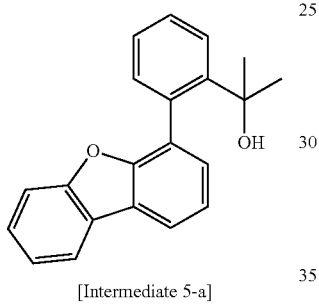

[Intermediate 5-a]

In a round-bottom flask reactor, tetrahydrofuran (250 ml) was mixed with [Intermediate 1-a](25 g, 80 mmol) and chilled to −78° C. in a nitrogen atmosphere. Thirty minutes later, drops of 1.0 M methyl magnesium bromide (210 ml, 240 mmol) were slowly added. After 1 hr, the mixture was heated to room temperature, stirred for about 2 hrs, and added with drops of an aqueous ammonium chloride solution. Extraction was followed by vacuum distillation. Recrystallization in hexane afforded [Intermediate 5-a]. (19.4 g, yield 80%).

Synthesis Example 5-(2): Synthesis of [Intermediate 5-b]

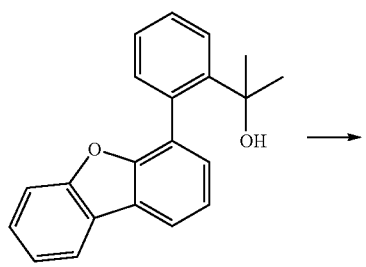

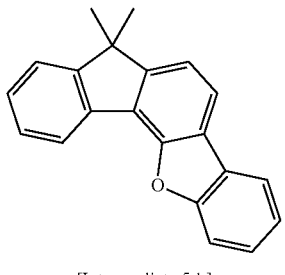

[Intermediate 5-b]

In a round-bottom flask reactor, acetic acid (300 ml) was stirred together with [Intermediate 5-a](20 g, 66 mmol), at 0° C. for 10 min, and then together with phosphoric acid (350 mL) at room temperature for about 1 hr. Following neutralization with an aqueous sodium hydroxide solution, extraction and vacuum concentration were conducted sequentially. Purification vial column chromatography afforded [Intermediate 5-b](13.7 g, yield 73%).

Synthesis Example 5-(3): Synthesis of [Intermediate 5-c]

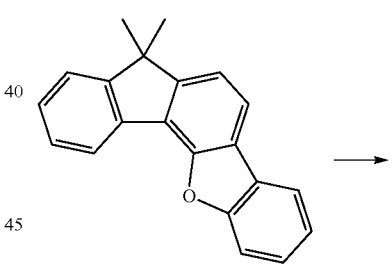

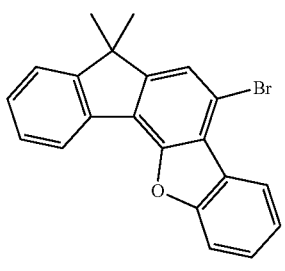

[Intermediate 5-c]

[Intermediate 5-c] was synthesized in the same manner as in Synthesis Example 2-(3), with the exception that [Intermediate 5-b] was used instead of [Intermediate 2-b]. (yield 45%)

Synthesis Example 5-(4): Synthesis of [Intermediate 5-d]

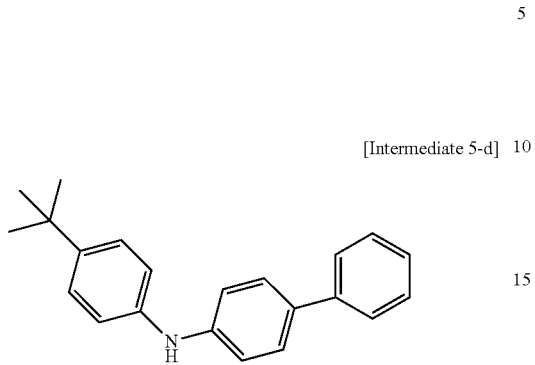

[Intermediate 5-d]

[Intermediate 5-d] was synthesized in the same manner as in Synthesis Example 3-(1), with the exception that 4-tert-butyl aniline and 4-bromobiphenyl were used instead of the aniline and 2-bromodibenzofuran, respectively. (yield 78%)

Synthesis Example 5-(5): Synthesis of Compound of [Chemical Formula 75]

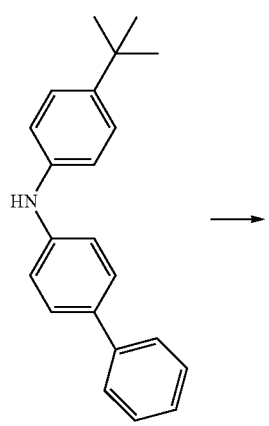

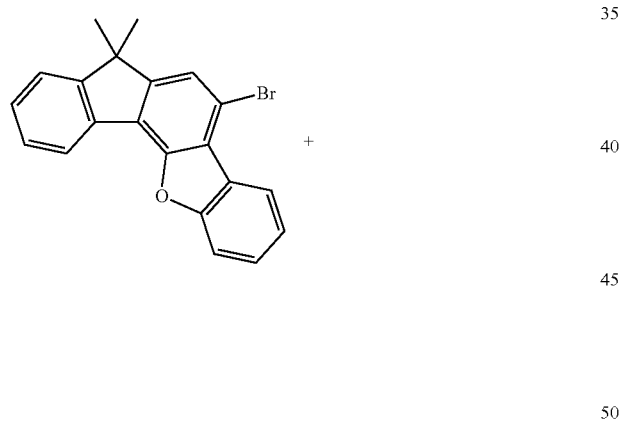

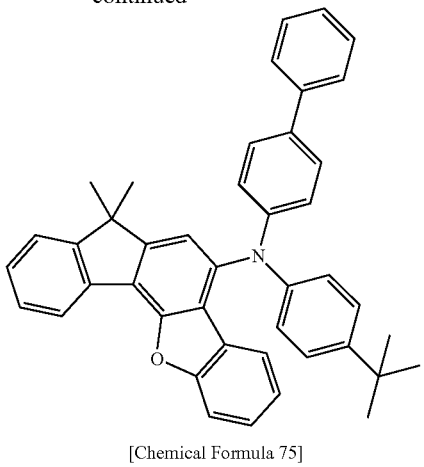

[Chemical Formula 75]

The compound of [Chemical Formula 75] was synthesized in the same manner as in Synthesis Example 2-(4), with the exception that [Intermediate 5-c] and [Intermediate 5-d] were used instead of [Intermediate 2-c] and bis-biphen-4-yl-amine, respectively. (yield 67%)

MS (MALDI-TOF): m/z 583.29 [M$^+$]

Example 6: Synthesis of Compound of Chemical Formula 87

Synthesis Example 6-(1): Synthesis of [Intermediate 6-a]

[Intermediate 6-a]

[Intermediate 6-a] was synthesized in the same manner as in Synthesis Example 1-(1) and Synthesis Examples 5-(1) to 5-(3), with the exception that (6-phenyldibenzo[b,d]furan-4-yl)boronic acid was used instead of 4-dibenzofuranboronic acid of Synthesis Example 1-(1). (yield 48%)

Synthesis Example 6-(2). [Intermediate 6-b]

[Intermediate 6-b] was synthesized in the same manner as in Synthesis Example 3-(1), with the exception that 2-bromo-9,9-dimethylfluoorene was used instead of 2-bromodibenzofuran. (yield 75%)

Synthesis Example 6-(3). [Chemical Formula 87]

The compound of [Chemical Formula 87] was synthesized in the same manner as in Synthesis Example 2-(4), with the exception that [Intermediate 6-a] and [Intermediate 6-b] were used instead of [Intermediate 2-c] and bis-biphen-4-yl amine, respectively. (yield 69%)

MS (MALDI-TOF): m/z 643.29 [M+]

Example 7: Synthesis of Compound of Chemical Formula 115

Synthesis Example 7-(1): Synthesis of [Intermediate 7-a]

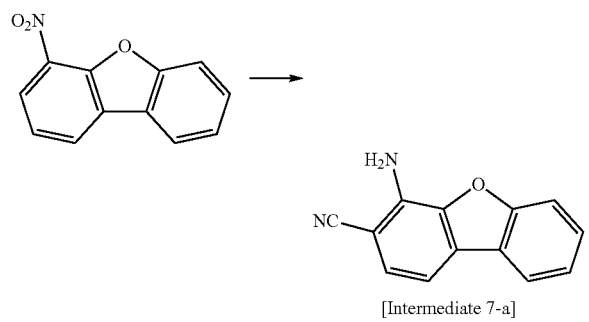

[Intermediate 7-a]

In a 2-L round-bottom flask reactor, ethyl cyanoacetate (202.9 g, 1.794 mol) and dimethyl formamide (500 ml) were placed. Potassium hydroxide (67.10 g, 1.196 mol) and potassium cyanide (38.95 g, 0.598 mol) were added, followed by dimethyl formamide (200 ml). The resulting mixture was stirred at room temperature, added with 4-nitrodibenzofuran (127. g, 0.737 mol) little by little, and then stirred at 50° C. for 72 hrs. After completion of the reaction, an aqueous sodium hydroxide solution (25%, 200 ml) was added and stirred for 3 hrs under reflux. After cooling to room temperature, extraction with ethyl acetate and water were conducted. The organic layer thus formed was separated, and concentrated in a vacuum. Purification via column chromatography afforded [Intermediate 7-a]. (20.0 g, 16%)

Synthesis Example 7-(2): Synthesis of [Intermediate 7-b]

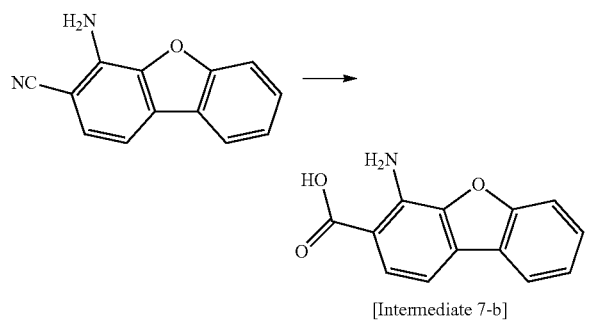

[Intermediate 7-b]

In a 2-L round-bottom flask reactor, a mixture of [Intermediate 7-a](20.0 g, 96 mmol), ethanol (600 ml), and potassium hydroxide (170 ml, 142.26 g, 2.53 mol) was stirred for 12 hrs under reflux. After completion of the reaction mixture was cooled to room temperature, and then acidified with 6 N HCl (400 ml). Stirring for 20 min was followed by filtration. The solid thus obtained was washed with ethanol to afford [Intermediate 7-b]. (17.0 g, 88.5%)

Synthesis Example 7-(3): Synthesis of [Intermediate 7-c]

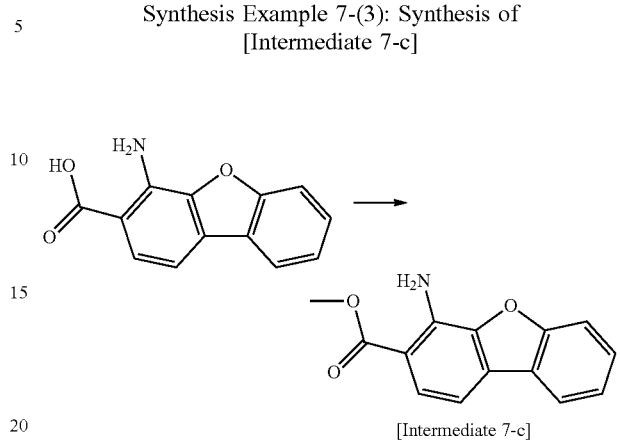

[Intermediate 7-c]

In a 2-L round-bottom flask reactor, a mixture of [Intermediate 7-b](17.0 g, 75 mmol) and sulfuric acid (15 ml) was stirred for 72 hrs under reflux. After completion of the reaction, the reaction mixture was extracted with ethyl acetate and water. The organic layer was separated and washed with an aqueous sodium hydrogen carbonate solution. An excess of methanol was added during the vacuum concentration of the organic layer, followed by filtration to afford [Intermediate 7-c]. (14.0 g, 77.6%)

Synthesis Example 7-(4): Synthesis of [Intermediate 7-d]

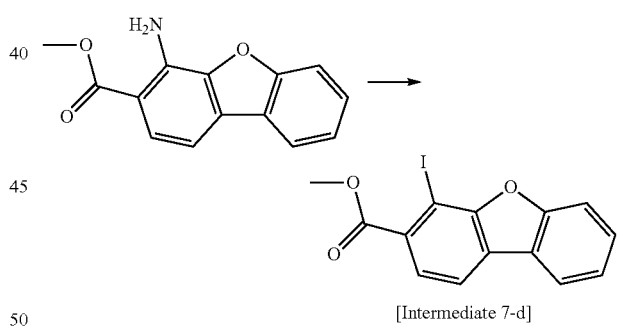

[Intermediate 7-d]

In a 500-mL round-bottom flask reaction, [Intermediate 7-c>(12 g, 58 mmol), HCl (15 ml), and water (75 ml) were stirred together for 1 hr at 0° C. At the same temperature, an aqueous solution (38 ml) of sodium nitrite (75.6 g, 81 mmo) was dropwise added to the reaction mixture and then stirred for 1 hr. An aqueous solution (38 ml) of potassium iodide (22.4 g, 135 mmol) was dropwise added with care not to increase the temperature of the reaction solution above 5° C. Stirring was continued for 5 hrs at room temperature, and after completion of the reaction, the reaction mixture was washed with an aqueous sodium thiosulfate solution, and extracted with ethylacetate and water. The organic layer was separated and concentrated in a vacuum. Purification through column chromatography gave [Intermediate 7-d]. (11 g, 91%)

Synthesis Example 7-(5): Synthesis of [Intermediate 7-e]

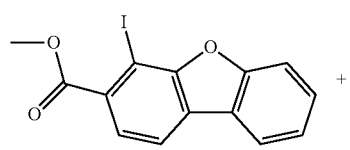
+
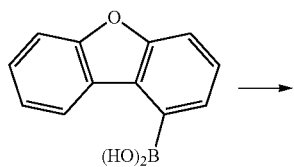

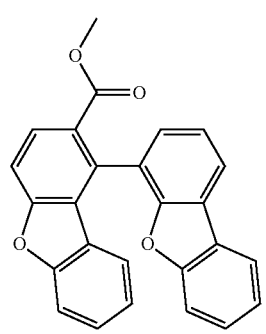

[Intermediate 7-e]

[Intermediate 7-e] was synthesized in the same manner as in Synthesis Example 1-(1), with the exception that [Intermediate 7-d] and 1-dibenzofuranboronic acid were used instead of methyl 2-iodobenzoate and 4-dibenzofuranboronic acid, respectively. (10.1 g, 75%)

Synthesis Example 7-(6): Synthesis of [Intermediate 7-f]

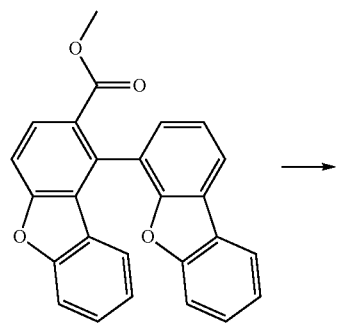

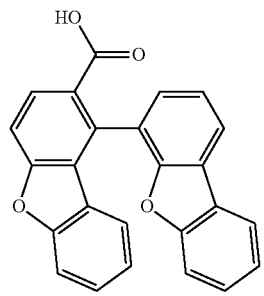

[Intermediate 7-f]

In a 500-mL round-bottom flask reactor, [Intermediate 7-e](10.0 g, 25 mmol), sodium hydroxide (1.1 g, 28 mmol), and ethanol (80 ml) were stirred together for 48 hrs under reflux. After the completion of the reaction was confirmed by thin layer chromatography, the reaction mixture was cooled to room temperature. The chilled solution was acidified with drops of 2-N HCl, followed by stirring for 30 min. The solid thus formed was filtered, and recrystallized in dichloromethane and hexane to afford [Intermediate 7-f]. (7.3 g, 77%)

Synthesis Example 7-(7): Synthesis of [Intermediate 7-g]

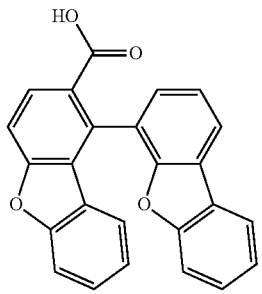

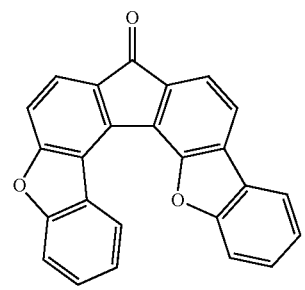

[Intermediate 7-g]

In a 250-mL round-bottom flask reactor, [ntermediate 7-f](7 g, 18 mmol) and methanesulfonic acid (72 ml) were stirred together for 3 hrs at 80° C. After the completion of the reaction was confirmed by thin layer chromatography, the reaction mixture was cooled to room temperature and dropwise added to ice water (75 ml). After stirring for 30 min, the solid thus formed was filtered and washed with water and methanol to afford [Intermediate 7-g]. (6.1 g, 94%)

Synthesis Example 7-(8): Synthesis of [Intermediate 7-h]

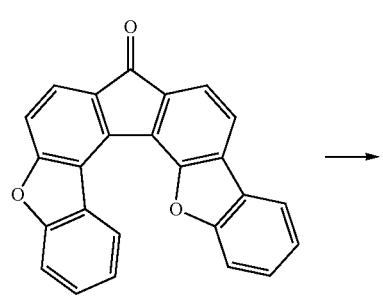

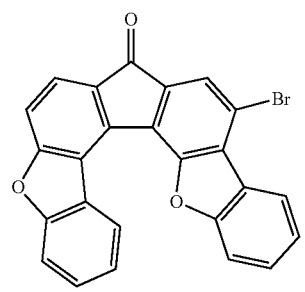

[Intermediate 7-h]

[Intermediate 7-h] was synthesized in the same manner as in Synthesis Example 1-(4), with the exception that [Intermediate 7-g] was used instead of [Intermediate 1-c]. (4.3 g, 85%)

Synthesis Example 7-(8): Synthesis of [Intermediate 7-i]

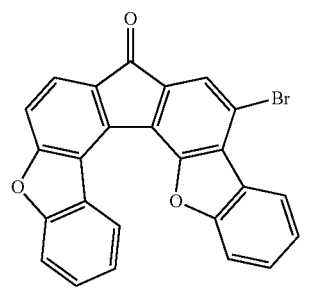

+

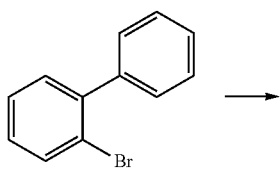

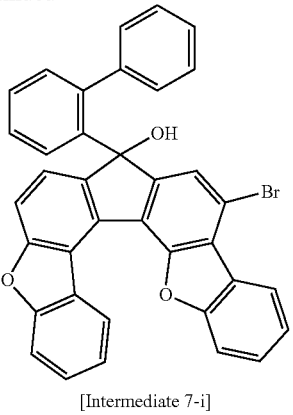

[Intermediate 7-i]

In a 250-ml round-bottom flask reactor, 2-bromobiphenyl (3.2 g, 13.7 mmol) and tetrahydrofuran (40 ml) were chilled at −78° C. in a nitrogen atmosphere. At the same temperature, n-butyl lithium (8 ml, 12 mmol) was dropwise added to the reaction solution which was then stirred for 2 hrs. Thereafter, [Intermediate 7-h](4 g, 9.1 mmol) was added little by little to the reaction solution, and stirred at room temperature. When the reaction mixture started to change color, the reaction was monitored via thin layer chromatography. After the reaction was stopped with $H_2O$ (20 ml), extraction was conducted with ethyl acetate and water. The organic layer was separated, concentrated in a vacuum, and recrystallized in acetonirile to afford [Intermediate 7-i]. (4 g, 74%)

Synthesis Example 7-(9): Synthesis of [Intermediate 7-j]

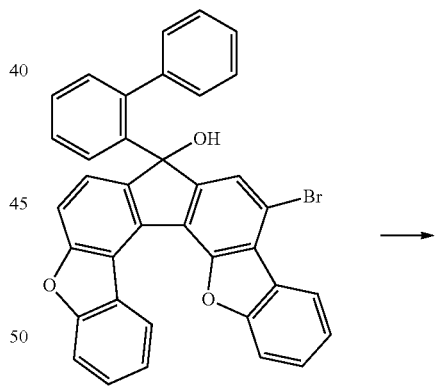

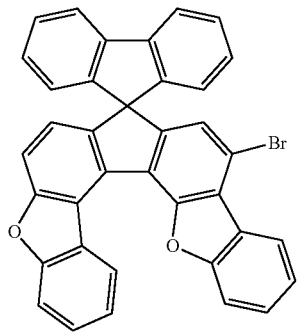

[Intermediate 7-j]

In a 250-ml round-bottom flask reactor, a mixture of [Intermediate 7-i](4.0 g, 7 mmol), acetic acid (30 ml), and sulfuric acid (1 ml) was stirred for 5 hrs under reflux. When a precipitate was formed, the completion of the reaction was monitored using thin layer chromatography. The reaction mixture was then cooled to room temperature and filtered. The filtrate was washed with H$_2$O and methanol and dissolved in monochlorobenzene. Following silica gel chromatography, the fraction was concentrated and cooled to room temperature to give [Intermediate 7-j]. (3.5 g, 86%)

Synthesis Example 7-(10): Synthesis of Compound of [Chemical Formula 115]

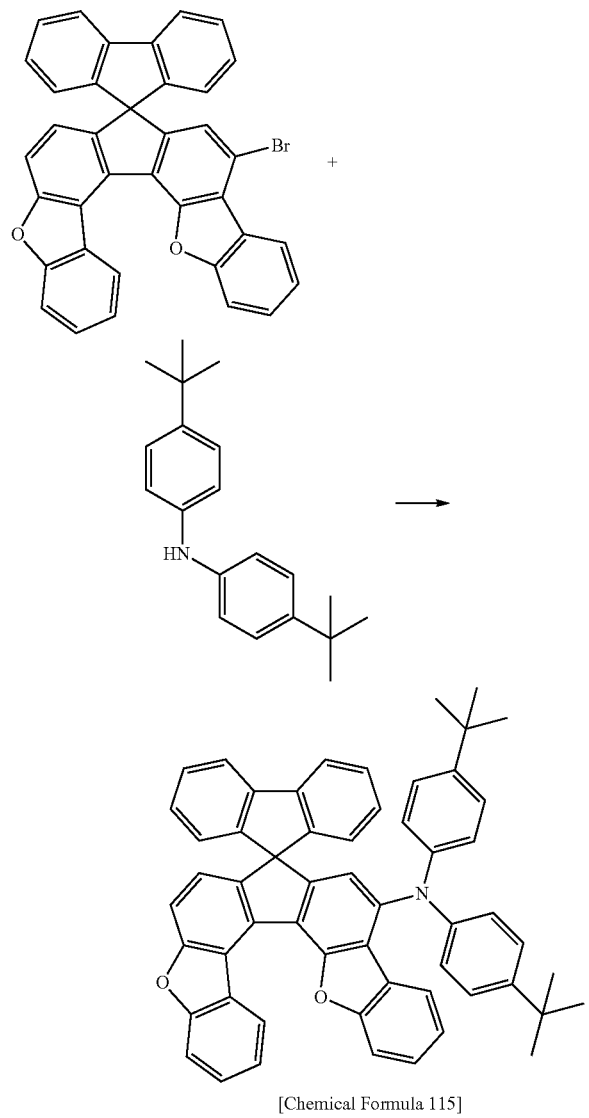

[Chemical Formula 115]

The compound of [Chemical Formula 115] was synthesized in the same manner as in Synthesis Example 2-(4), with the exception that [Intermediate 7-j] and bis(4-tert-butyl phenyl)amine were used instead of [Intermediate 2-c] and bis-biphen-4-yl amine, respectively. (yield 45%)

MS (MALDI-TOF): m/z 775.35 [M$^+$]

Example 8: Synthesis of Compound of Chemical Formula 131

Synthesis Example 8-(1): Synthesis of [Intermediate 8-a]

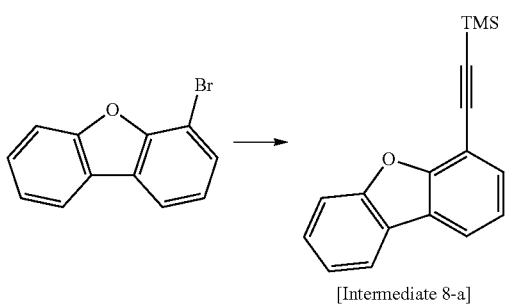 [SMILES: Brc1cccc2c1oc1ccccc12 ; C[Si](C)(C)C#Cc1cccc2c1oc1ccccc12]

[Intermediate 8-a]

In a 2-L round bottom flask, 4-bromodibenzofuran (100.0 g, 0.405 mol), ethynyl trimethylsilane (47.7 g, 0.486 mol), [1,1'-bis(diphenylphosphino)ferrocene]dichloropalladium (9.92 g, 0.012 mol), copper iodide (2.31 g, 0.012 mol), triphenylphosphine(10.6 g, 0.040 mol), and triethylamine (700 ml) were stirred for 5 hrs under reflux in a nitrogen atmosphere. After completion of the reaction, the reaction mixture was cooled to room temperature and added with heptane (500 ml) to terminate the reaction. Filtration was conducted through a silica gel pad topped with celite. The filtrate was concentrated in a vacuum to afford [Intermediate 8-a]. (130 g, 84%)

Synthesis Example 8-(2): Synthesis of [Intermediate 8-b]

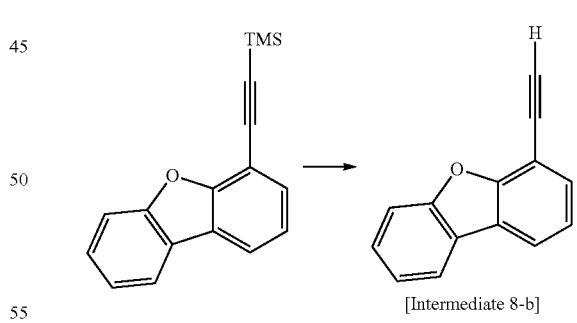

[Intermediate 8-b]

In a 2-L round-bottom flask reactor, [Intermediate 8-a] (130 g, 0.492 mol), potassium carbonate (101.9 g, 0.738 mol), methanol (650 ml), and tetrahydrofuran (650 ml) were stirred together for 2 hrs at room temperature. After completion of the reaction, heptane (500 ml) was added to terminate the reaction. The reaction mixture was filtered and the filtrate was extracted with ethyl acetate and water. The organic layer thus formed was isolated and dried over magnesium sulfate. Filtration and vacuum concentration afforded [Intermediate 8-b] as an oil. (82 g, 84%)

Synthesis Example 8-(3): Synthesis of [Intermediate 8-c]

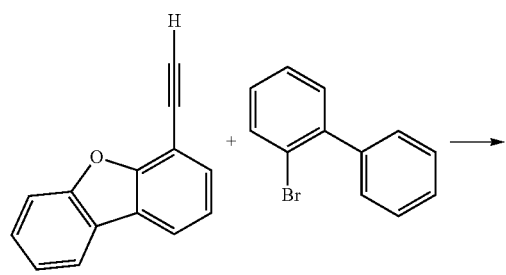

[Intermediate 8-c]

In a 2-L round-bottom flask reactor, 2-bromobiphenyl (66.0 g, 0.283 mol), [Intermediate 8-b](65.3 g, 0.340 mol), [1,1'-bis(diphenylphosphino)ferrocene]dichloropalladium (6.94 g, 0.008 mol), copper iodide (1.62 g, 0.008 mol), triphenylphosphine (7.4 g, 0.028 mol), and triethylamine (500 ml) were stirred for hrs under reflux in a nitrogen atmosphere. After completion of the reaction, the reaction mixture was cooled to room temperature and added with heptane (400 ml) to terminate the reaction. Filtration was conducted through a silica gel pad topped with celite. The filtrate was concentrated in a vacuum to afford [Intermediate 8-c]. (80 g, 82%)

Synthesis Example 8-(4): Synthesis of [Intermediate 8-d]

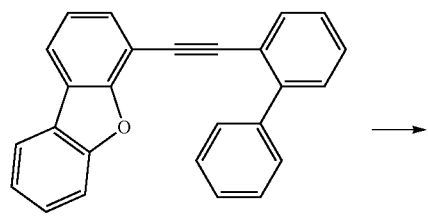

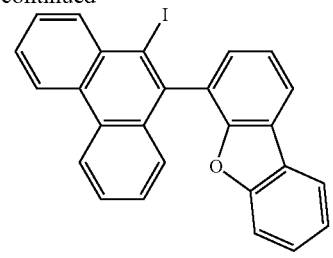

[Intermediate 8-d]

In a 2-L round-bottom flask reactor, a solution of [Intermediate 8-c](80.0 g, 0.232 mol) in dichloromethane (960 ml) was cooled to −78° C. under a nitrogen atmosphere. Iodine monochloride (278.4 ml, 0.279 mol) was dropwise added to the chilled solution, which was then stirred at room temperature for 12 hrs. After completion of the reaction, the reaction mixture was stirred together with an aqueous saturated sodium thiosulfate solution. Following extraction with dichloromethane and water, the organic layer was isolated, concentrated in a vacuum, and recrystallized in methanol to afford [Intermediate 8-d]. (67 g, 61.3%)

Synthesis Example 8-(5): Synthesis of [Intermediate 8-e]

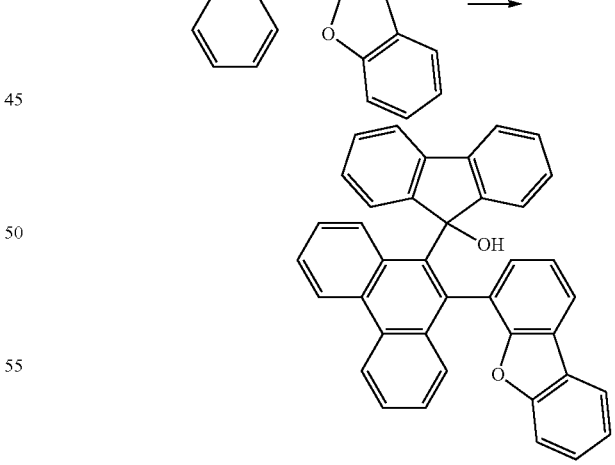

[Intermediate 8-e]

In a 500-mL round-bottom flask reactor, a solution of [Intermediate 4-d](54.8 g, 0.117 mol) in tetrahydrofuran (150 ml) was cooled to −78° C. under a nitrogen atmosphere. At the same temperature, 1.6 M n-butyl lithium (62.4 ml, 0.1 mol) was dropwise added to the chilled solution and stirred for 1 hr. Then, a solution of 9-fluorenone (15.0 g, 0.083 mol)

in tetrahydrofuran (50 ml) was dropwise added before stirring at room temperature for 8 hrs. After completion of the reaction, extraction was performed with ethyl acetate and water. The organic layer thus formed was isolated and dried over magnesium sulfate. Vacuum concentration subsequent to filtration afforded [Intermediate 8-e] as an oil. (33.2 g, 76%)

Synthesis Example 8-(6): Synthesis of [Intermediate 8-f]

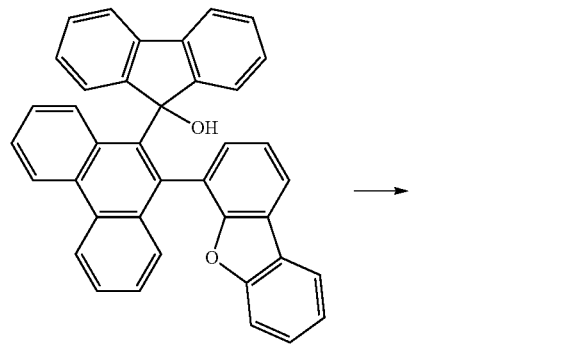

[Intermediate 8-f]

In a 1-L round-bottom flask reactor, [Intermediate 8-e] (33.3 g, 0.063 mol), acetic acid (330 ml), and sulfuric acid (3 ml) were stirred together for 3 hrs under reflux. After the completion of the reaction was confirmed using thin-layer chromatography, the reaction mixture was cooled to room temperature. The precipitates thus formed were filtered and washed with $H_2O$ and methanol to afford [Intermediate 8-f]. (28.6 g, 88%>

Synthesis Example 8-(7): Synthesis [Intermediate 8-g]

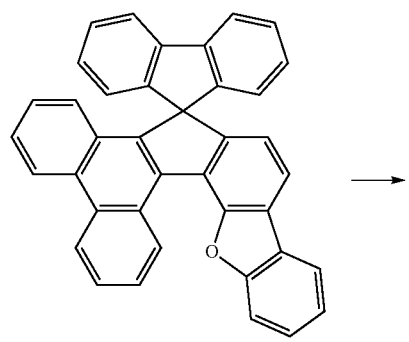

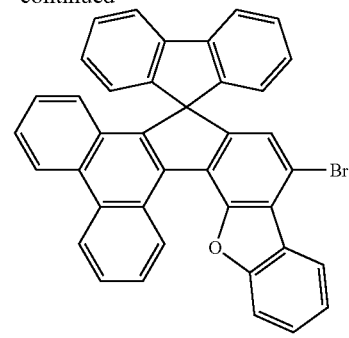

[Intermediate 8-g]

[Intermediate 8-g] was synthesized in the same manner as in Synthesis Example 1-(4), with the exception that [Intermediate 8-f] was used instead of [Intermediate 1-c]. (6.0 g, 82%)

Synthesis Example 8-(7): Synthesis of Compound of [Chemical Formula 131]

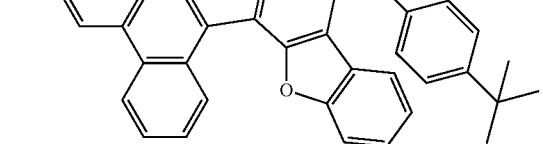

[Chemical Formula 131]

The compound of [Chemical Formula 131] was synthesized in the same manner as in Synthesis Example 2-(4), with the exception that [Intermediate 8-g] and 4-tert-butyl- N-phenylaniline were used instead of [Intermediate 2-c] and bis-biphen-4-yl amine, respectively. (yield 45%)

MS (MALDI-TOF): m/z 729.30 [M$^{+}$]

Example 9: Synthesis of Compound of Chemical Formula 42

Synthesis Example 9-(1): Synthesis of [Intermediate 9-a]

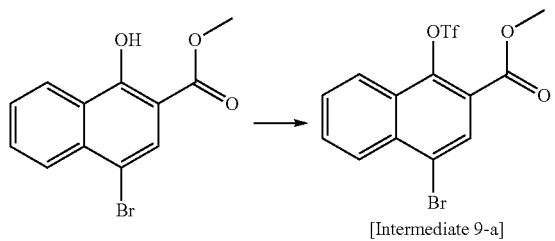 [SMILES: COC(=O)c1cc(Br)c2ccccc2c1O ; COC(=O)c1cc(Br)c2ccccc2c1OS(=O)(=O)C(F)(F)F]

[Intermediate 9-a]

In a 2-L round-bottom flask reactor, methyl-4-bromo-1-hydroxy-2-naphtoate (50 g, 178 mmol) was stirred together with dichloromethane. Under a nitrogen atmosphere, pyridine (28.1 g, 356 mmol) was added and stirred at room temperature for 20 min. The resulting solution was cooled to 0° C. and then added with drops of trifluoromethanesulfonic anhydride (65.24 g, 231 mmol) under a nitrogen atmosphere. After 3 hrs of stirring, the completion of the reaction was confirmed by TLC. Water (20 ml) was added, and the mixture was stirred for 10 min. The reaction mixture was concentrated in a vacuum, followed by purification through column chromatography to afford [Intermediate 9-a]. (45 g, 61%).

Synthesis Example 9-(2): Synthesis of [Intermediate 9-b]

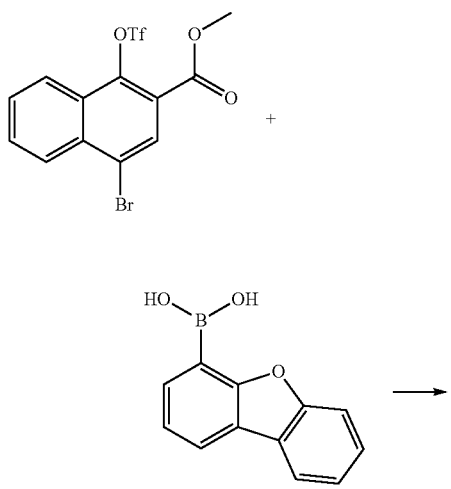

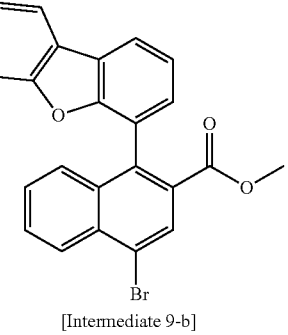

[Intermediate 9-b]

In a 1-L round-bottom flask reactor, a mixture of [Intermediate 9-a](45.0 g, 0.109 mol), 4-dibenzoboronic acid (25.4 g, 0.120 mol), tetrakis(triphenylphosphine)palladium (2.5 g, 0.22 mmol), and potassium carbonate (30.1 g, 0.218 mol) was stirred together with toluene (300 mL), ethanol (130 mL) and water (90 mL) at 80° C. for 5 hrs. After completion of the reaction, the reaction mixture was cooled to room temperature and extracted with ethyl acetate. The organic layer was isolated and concentrated in a vacuum. Purification through column chromatography afforded [Intermediate 9-b](22.0 g, 46.1%).

Synthesis Example 9-(3): Synthesis of [Intermediate 9-c]

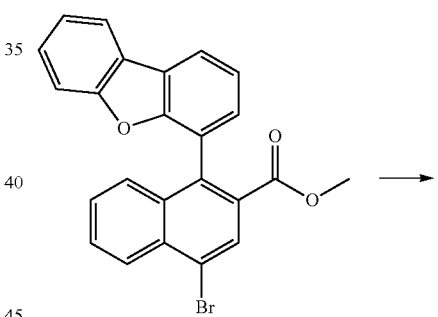

[Intermediate 9-c]

In a 1-L round-bottom flask reactor, [Intermediate 9-b] (22.0, 0.05 mol) was stirred together with sodium hydroxide (2.65 g, 0.066 mol) for 48 hrs under reflux. After completion of the reaction, the reaction mixture was cooled to room temperature. The chilled solution was acidified with drops of 2-N HCl, followed by stirring for 30 min. The solid thus formed was filtered and recrystallized in dichloromethane and n-hexane to afford [Intermediate 9-c]. (17.6 g, 83%).

Synthesis Example 9-(4): Synthesis of [Intermediate 9-d]

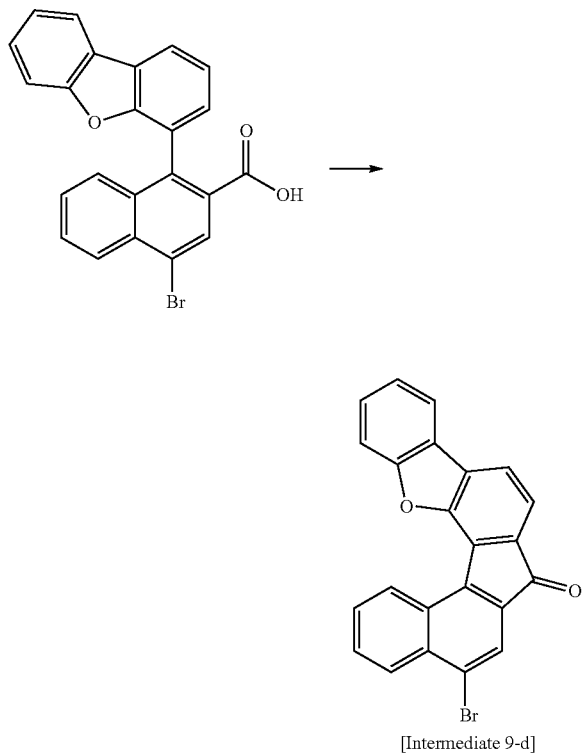

[Intermediate 9-d]

In a 500-mL round-bottom flask reactor, [Intermediate 9-c](17.6 g, 0.042 mol) and methanesulfonic acid (170 ml) were stirred together for 3 hrs at 80° C. After the completion of the reaction was confirmed using thin-layer chromatography, the reaction mixture was cooled to room temperature and dropwise added to ice water (150 ml). After stirring for 30 min, the precipitates thus formed were filtered and washed with water and methanol. They were dissolved in monochlorobenzene and filtered through a silica gel pad. The filtrate was concentrated by heating and recrystallized in acetone to afford [Intermediate 9-d]. (12 g, 71%).

Synthesis Example 9-(5): Synthesis of [Intermediate 9-e]

[Intermediate 9-e]

In a 1-L round-bottom flask reactor, [Intermediate 9-e] (12.0 g, 0.030 mol) and dichloromethane (360 ml) were stirred together at room temperature, during which a dilution of bromine (3.1 ml, 0.06 mol) in dichloromethane (40 ml) was dropwise added, followed by stirring at room temperature for 12 hrs. After completion of the reaction, methanol (100 ml) was added to induce the formation of precipitates. They were then filtered and washed with methanol. Recrystallization in 1,2-dichlorobenzene and acetone afforded [Intermediate 9-e]. (10.3 g, 72%).

Synthesis Example 9-(6): Synthesis of [Intermediate 9-f]

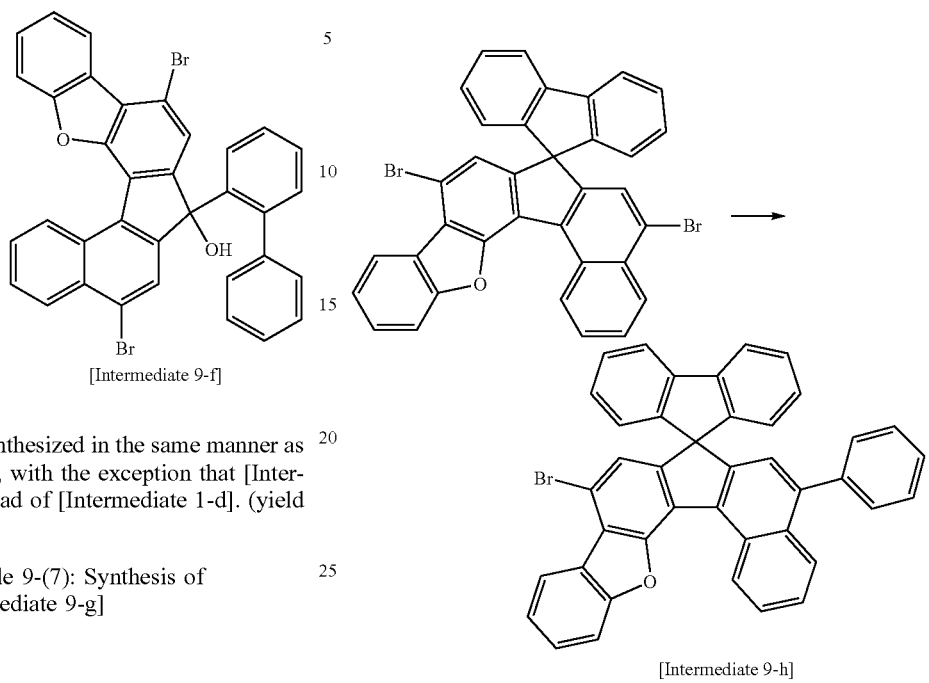

[Intermediate 9-f]

[Intermediate 9-f] was synthesized in the same manner as in Synthesis Example 1-(5), with the exception that [Intermediate 9-e] was used instead of [Intermediate 1-d]. (yield 73%)

Synthesis Example 9-(7): Synthesis of [Intermediate 9-g]

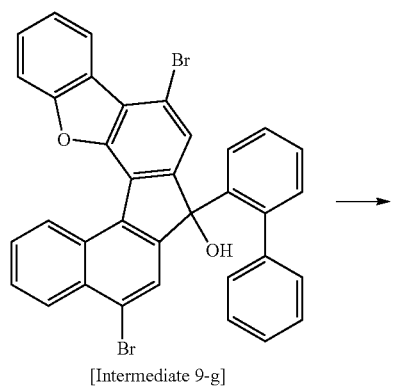

[Intermediate 9-g]

[Intermediate 9-g] was synthesized in the same manner as in Synthesis Example 1-(6), with the exception that [Intermediate 9-f] was used instead of [Intermediate 1-e]. (yield 65%)

Synthesis Example 9-(8): Synthesis of [Intermediate 9-h]

[Intermediate 9-h]

[Intermediate 9-h] was synthesized in the same manner as in Synthesis Example 1-(1), with the exception that [Intermediate 9-g] and phenylboronic acid were used instead of methyl 2-iodobenzoate and 4-dibenzofuranboronic acid. (yield 45%)

Synthesis Example 9-(9): Synthesis of Compound of [Chemical Formula 42]

The compound of [Chemical Formula 42] was synthesized in the same manner as in Synthesis Example 2-(4), with the exception that [Intermediate 9-h] and N-phenyl-4-biphenyl amine were used instead of [Intermediate 2-c] and bis-biphen-4-yl amine. (yield 44%)

MS (MALDI-TOF): m/z 775.29 [M$^+$]

Example 10: Synthesis of Compound of Chemical Formula 146

Synthesis Example 10-(1): Synthesis of [Intermediate 10-a]

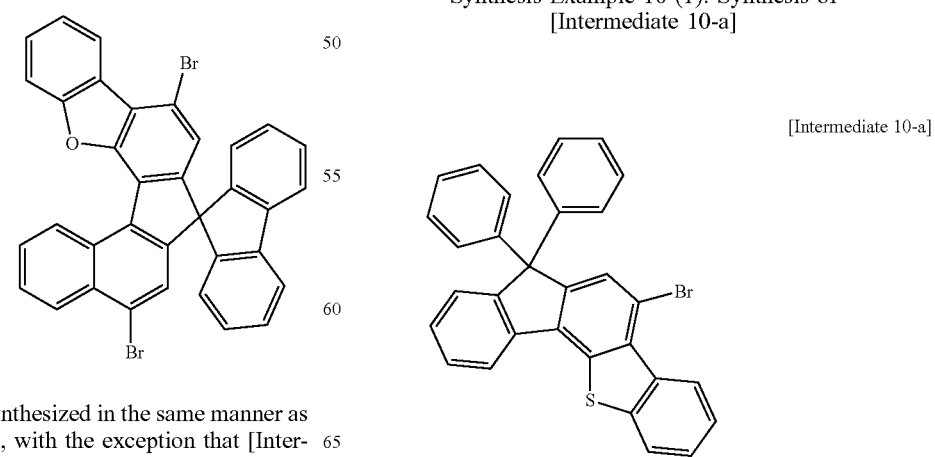

[Intermediate 10-a]

[Intermediate 10-a] was synthesized in the same manner as in Synthesis Example 1-(1), Synthesis Examples 2-(1) to 2-(3), with the exception that 4-dibenzothiophene boronic acid was used instead of 4-dibenzofuranboronic acid of Synthesis Example 1-(1). (yield 68%)

Synthesis Example 10-(2): Synthesis of [Intermediate 10-b]

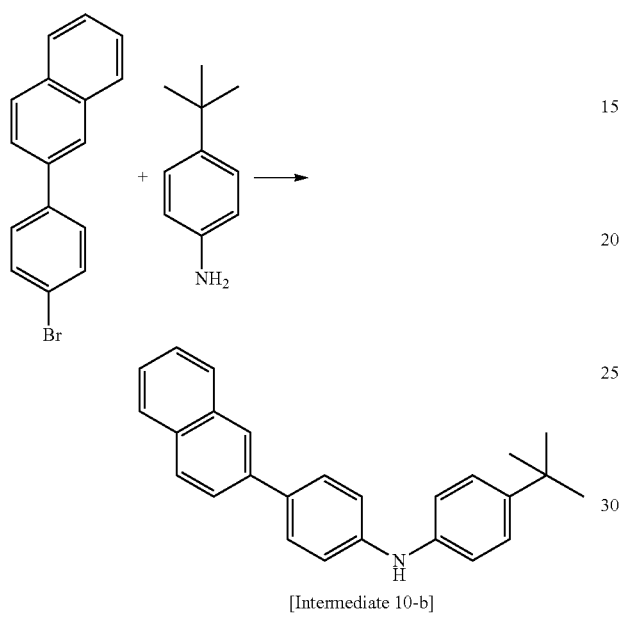

[Intermediate 10-b]

In a 250-ml round-bottom flask reactor, 1-bromo-4-(2-naphthyl)benzene (10.0 g, 0.035 mol), 4-tert-butyl aniline (5.8 g, 0.039 mol), tris(dibenzylidne acetone)dipalladium(0) (0.65 g, 0.0007 mol), sodium tert-butoxide (6.79 g, 0.0706 mol), 2,2'-bis(diphenylphosphino)-1,1'-binaphthalene (0.44 g, 0.0007 mol), and toluene (100 ml) were stirred together for 3 hrs under reflux. After completion of the reaction, the reaction mixture was cooled to room temperature and extracted with ethyl acetate and water. The organic layer was isolated, dried over magnesium sulfate, and concentrated in a vacuum. Purification through column chromatography gave [Intermediate 10-b](10 g, 80%).

Synthesis Example 10-(3): Synthesis of Compound of [Chemical Formula 146]

The compound of [Chemical Formula 146] was synthesized in the same manner as in Synthesis Example 2-(4), with the exception that [Intermediate 10-a] and [Intermediate 10-b] were used instead of [Intermediate 2-c] and bis-biphen-4-yl amine, respectively. (yield 48%)
MS (MALDI-TOF): m/z 773.31 [M+]

Examples 1 AND 2: Fabrication of Organic Light-Emitting Diode-Hole Transport Layer (HTL)

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were formed of DNTPD (700 Å) and the α-NPD of the present disclosure (300 Å) in that order. A light-emitting layer (250 Å) was formed of a mixture including [BH1] as a host and 3% of [BD1] as a dopant. On the light-emitting layer, then, [Chemical Formula E-2] for an electron transport layer (250 Å), [Chemical Formula E-1] for an electron injection layer (10 Å), and Al (1000 Å) were deposited in the order to fabricate an organic light-emitting diode. The organic light-emitting diodes thus obtained were measured at 0.4 mA for luminescence properties.

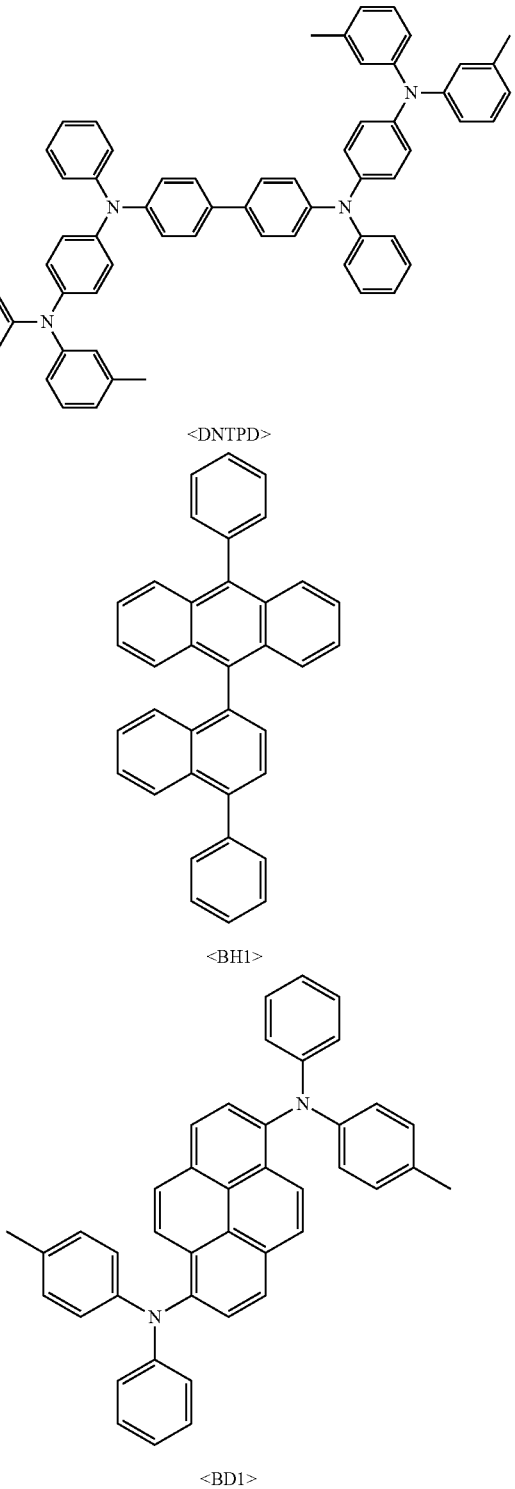

[Chemical Formula E-1]

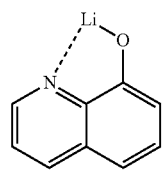

[Chemical Formula E-2]

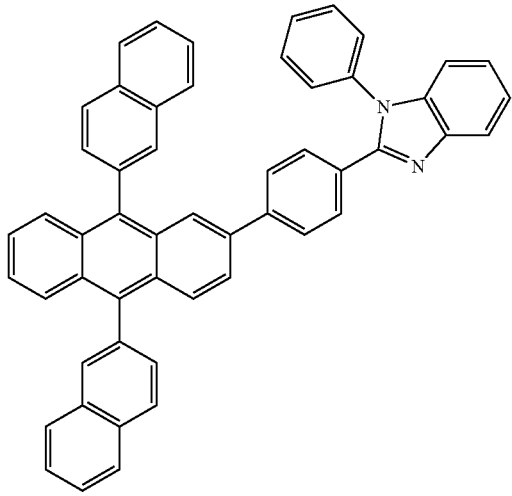

Comparative Example 1

An organic light-emitting diode was fabricated in the same manner as in Examples 1 and 2, with the exception that <α-NPD> was used for the hole transport layer. The organic light-emitting diode was measured at 0.4 mA for luminescence properties, and the results are given in Table 1, below. The structure of <α-NPD> is as follows.

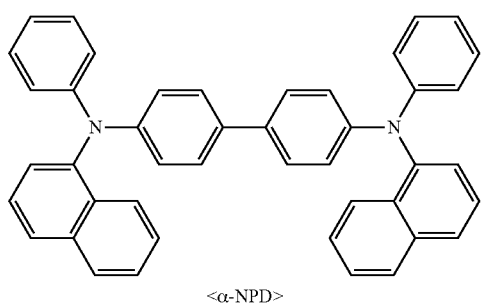 [SMILES: c1ccc(N(c2ccc(-c3ccc(N(c4ccccc4)c4cccc5ccccc45)cc3)cc2)c2cccc3ccccc23)cc1]

<α-NPD>

TABLE 1

| Ex. # | Hole Transport Cpd. | V | EQE | CIEx | CIEy |
|---|---|---|---|---|---|
| C. 1 | α-NPB | 3.8 | 6.6 | 0.135 | 0.109 |
| 1 | Chemical Formula 13 | 3.5 | 7.8 | 0.135 | 0.107 |
| 2 | Chemical Formula 107 | 3.7 | 7.9 | 0.135 | 0.108 |

Examples 3 and 4: Fabrication of Blue Organic Light-Emitting Diode-Electron Blocking Layer (B-EBL)

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were formed of DNTPD (700 Å) and α-NPD (300 Å) in that order. The amine compounds of Table 2, synthesized according to the present disclosure, were used to form a film (50 Å) as an electron-blocking layer. Subsequently, a light-emitting layer (250 Å) was formed of a mixture including [BH1] as a host and 3% of [BD1] as a dopant. On the light-emitting layer, then, a mixture of [Chemical Formula E-3]: Liq=1:1 for an electron transport layer and an electron injection layer, respectively, (250 Å), and Al (1000 Å) were deposited in that order to fabricate an organic light-emitting diode. The organic light-emitting diodes thus obtained were measured at 0.4 mA for luminescence properties.

[Chemical Formula E-3]

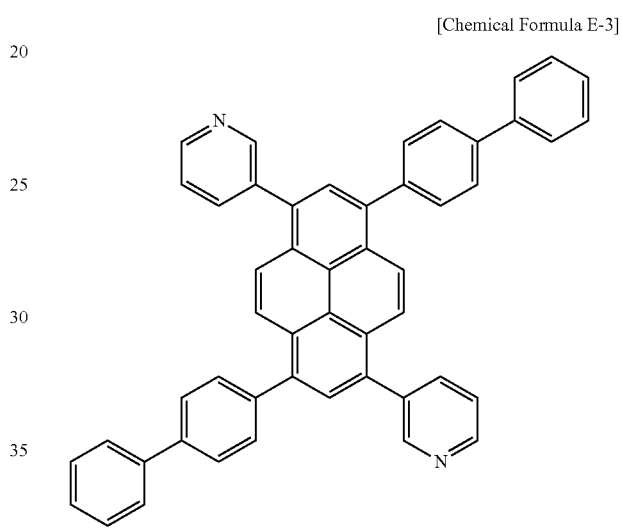

Comparative Example 2

An organic light-emitting diode was fabricated in the same manner as in Examples 3 and 4, with the exception that [EBL] was used for the electron-blocking layer. The structure of [EBL] is as follows.

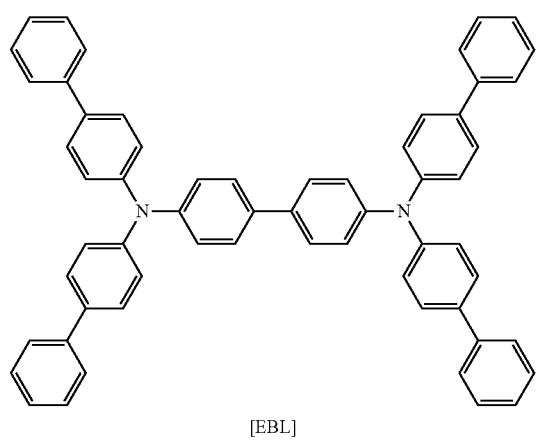 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

[EBL]

TABLE 2

| Ex. # | Electron-Blocking Layer | V | EQE | CIEx | CIEy |
|---|---|---|---|---|---|
| C. 2 | EBL | 3.8 | 8.3 | 0.136 | 0.108 |
| 3 | Chemical Formula 35 | 3.6 | 9.6 | 0.135 | 0.108 |
| 4 | Chemical Formula 91 | 3.6 | 9.9 | 0.137 | 0.109 |

Examples 5 to 7: Fabrication of Red Organic Light-Emitting Diode-Electron-Blocking Layer (R-EBL)

An ITO glass substrate was patterned to have a translucent area of 2 mm×2 mm and cleansed. The ITO glass was mounted in a vacuum chamber that was then set to have a base pressure of $1 \times 10^{-7}$ torr. On the ITO glass substrate, films were formed of DNTPD (700 Å) and α-NPD (300 Å) in that order. The amine compounds of Table 3, synthesized according to the present disclosure, were used to form a film (50 Å) as an electron-blocking layer, followed by sequentially depositing a red host (RH)+a red dopant (RD) (5%) (300 Å), Alq3 (350 Å), [Chemical Formula E-1](5 Å), and Al (1,000 Å). The organic light-emitting diodes thus obtained were measured at 0.4 mA for luminescence properties. T97 refers to the time taken for the initial luminance to decrease by 3%.

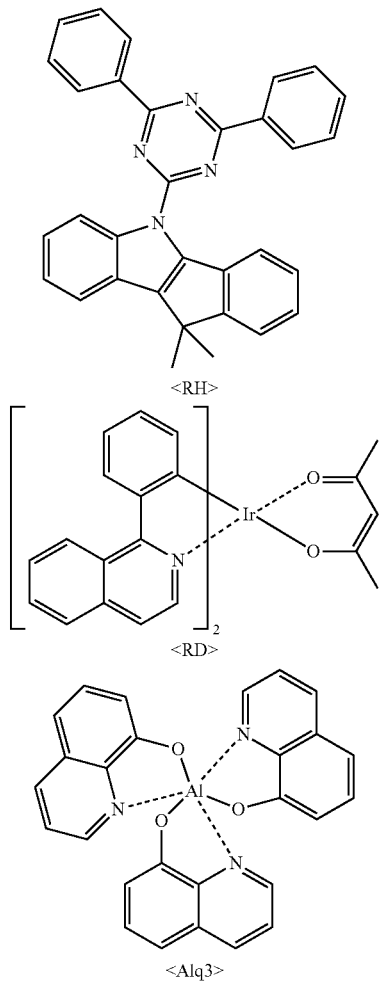

Comparative Example 3

An organic light-emitting diode was fabricated in the same manner as in Examples 5 to 7, with the exception that [R-EBL] was used for the electron-blocking layer. The structure of [R-EBL] is as follows.

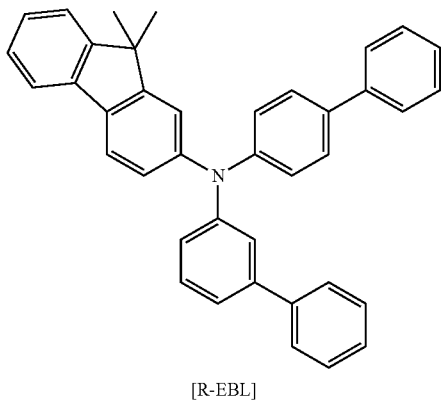 [SMILES: CC1(C)c2ccccc2-c2ccc(N(c3ccc(-c4ccccc4)cc3)c3cccc(-c4ccccc4)c3)cc21]

[R-EBL]

TABLE 3

| Ex. # | Electron-Blocking Layer | V | Cd/A | CIEx | CIEy | T97 |
|---|---|---|---|---|---|---|
| C. 3 | R-EBL | 3.9 | 19.5 | 0.663 | 0.336 | 50 |
| 5 | Chemical Formula 37 | 3.6 | 29.5 | 0.662 | 0.337 | 130 |
| 6 | Chemical Formula 75 | 3.6 | 30.7 | 0.663 | 0.336 | 170 |
| 7 | Chemical Formula 87 | 3.6 | 28.1 | 0.661 | 0.338 | 110 |

Examples 8 to 10: Fabrication of Green Organic Light-Emitting Diode-Electron-Blocking Layer (G-EBL)

An ITO glass substrate was patterned to have a translucent area of 2 mm×2 mm and cleansed. The ITO glass was mounted in a vacuum chamber that was then set to have a base pressure of $1 \times 10^{-6}$ torr. On the ITO glass substrate, films were formed of DNTPD (700 Å) and α-NPD (300 Å) in that order. The amine compounds of Table 4, synthesized according to the present disclosure, were used to form a film (50 Å) as an electron-blocking layer, followed by sequentially depositing a greenhost (GH)+a green dopant (GD) (5%) (300 Å), Alq3 (350 Å), [Chemical Formula E-1](5 Å), and Al (1,000 Å). The organic light-emitting diodes thus obtained were measured at 0.4 mA for luminescence properties.

TABLE 4

| Ex. # | Electron-Blocking Layer | V | Cd/A | CIEx | CIEy | T97 |
|---|---|---|---|---|---|---|
| C. 4 | G-EBL | 4.4 | 75.7 | 0.333 | 0.628 | 140 |
| 8 | Chemical Formula 2 | 4.1 | 72.5 | 0.334 | 0.628 | 360 |
| 9 | Chemical Formula 42 | 4.2 | 71.2 | 0.334 | 0.627 | 330 |
| 10 | Chemical Formula 146 | 4.2 | 54.2 | 0.333 | 0.628 | 300 |

As is understood from the data of Table 1, the amine compounds of the present disclosure enable the light-emitting diodes to operate at lower voltages with higher light emission efficiency than the conventional compound α-NPB usually used as a hole transport material. Also, when used in an electron-blocking layer, the organic compounds of the present disclosure exhibited higher light emission efficiency, a longer lifespan, and a lower driving voltage than conventional materials, as shown in Tables 2 to 4.

Compared to conventional organic light-emitting diodes, as described hitherto, the organic light-emitting diode in which the amine compound of the present disclosure is used for a hole transport layer, a hole injection layer, or an electron-blocking layer exhibits excellent device properties, such as higher light emission efficiency, a longer lifespan, and a lower driving voltage.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An amine compound, represented by the following [Chemical Formula B]:

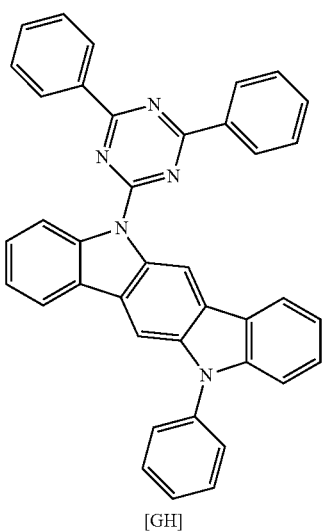

[GH]

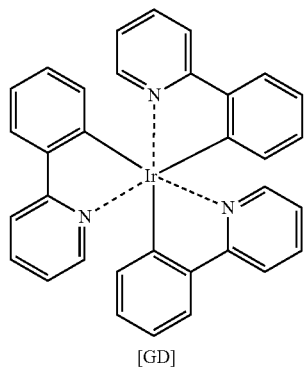

[GD]

Comparative Example 4

An organic light-emitting diode was fabricated in the same manner as in Examples 8 to 10, with the exception that [G-EBL] was used for the electron-blocking layer. The structure of [G-EBL] is as follows.

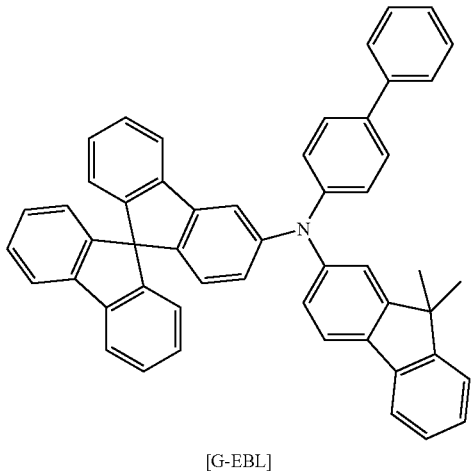 [SMILES: CC1(C)c2ccccc2-c2ccc(N(c3ccc(-c4ccccc4)cc3)c3ccc4c(c3)-c3ccccc3C43c4ccccc4-c4ccccc43)cc21]

[G-EBL]

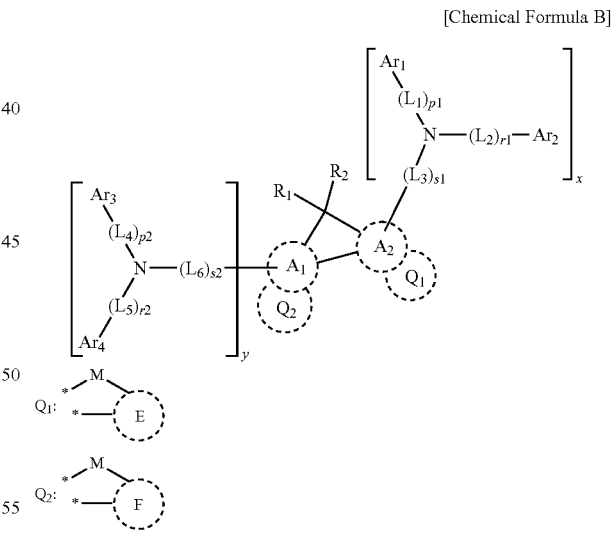

[Chemical Formula B]

wherein, $A_1$, E, and F are the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which the substituents $R_1$ and $R_2$ are bonded, and $A_2$ is an unsubstituted aromatic hydrocarbon ring of 6 to 50 carbon atoms in case of excluding an amine group

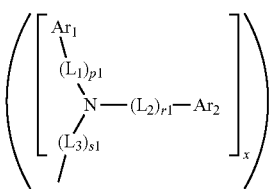

is bonded to the $A_2$ ring;

linkers $L_1$ to $L_6$ are the same or different, and are each independently a direct bond or a substituted or unsubstituted arylene of 6 to 60 carbon atoms;

M is any one selected from among N-$R_3$, $CR_4R_5$, $SiR_6R_7$, O, and S; $R_1$ to $R_7$, and $Ar_1$ to $Ar_4$ are the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms, a cyano, a nitro, and a halogen;

with the proviso that $R_1$ and $R_2$ together may form a mono- or polycyclic aliphatic or aromatic ring, which may be a heterocyclic ring containing a heteroatom selected from among N, O, P, Si, S, Ge, Se, and Te as a ring member;

p1, p2, r1, r2, s1, and s2 are each independently an integer of 1 to 3, with the proviso that when any of them is 2 or greater, the corresponding linkers may be the same or different;

$Ar_1$ may form a ring with $Ar_2$, and $Ar_3$ may form a ring with $Ar_4$;

x is 1 and y is 0;

two adjacent carbon atoms of the $A_1$ ring moiety may occupy respective positions * of structural Formula $Q_2$ to form a fused ring, and two adjacent carbon atoms of the $A_2$ ring moiety of Chemical Formula B may occupy respective positions of * of Structural Formula $Q_1$ to form a fused ring, wherein the term 'substituted' in the expression 'substituted or unsubstituted' for Chemical Formula B means having at least one substituent selected from the group consisting of a deuterium, a cyano, a halogen, a nitro, an alkyl of 1 to 24 carbon atoms, a halogenated alkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkylsilyl of 1 to 24 carbon atoms, an arylsilyl of 6 to 24 carbon atoms, and an aryloxy of 6 to 24 carbon atoms.

2. The amine compound of claim 1, wherein $A_1$, E, and F may be same or different, and are each independently a substituted or unsubstituted aromatic hydrocarbon ring of 6 to 50 carbon atoms.

3. The amine compound of claim 2, wherein the substituted or unsubstituted aromatic hydrocarbon ring of 6 to 50 carbon atoms is selected from among compounds represented by the following [Structural Formula 10] to [Structural Formula 21]:

[Structural Formula 10]

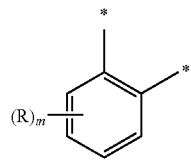

[Structural Formula 11]

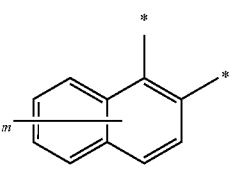

[Structural Formula 12]

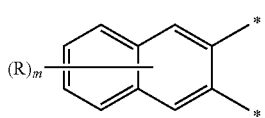

[Structural Formula 13]

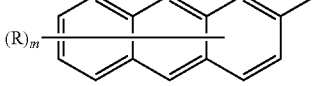

[Structural Formula 14]

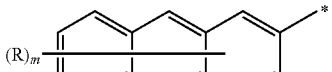

[Structural Formula 15]

[Structural Formula 16]

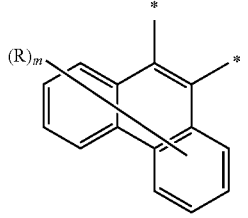

[Structural Formula 17]

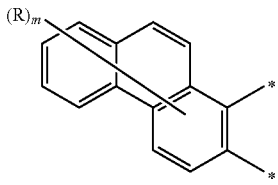

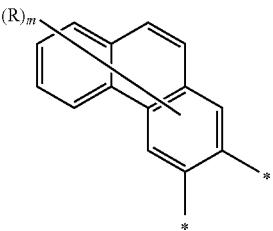

[Structural Formula 18]

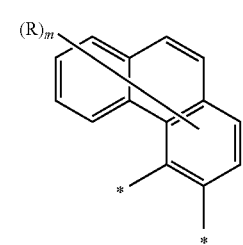

[Structural Formula 19]

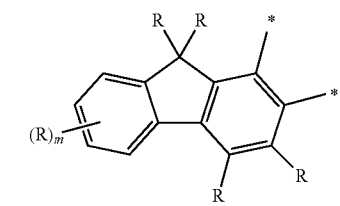

[Structural Formula 20]

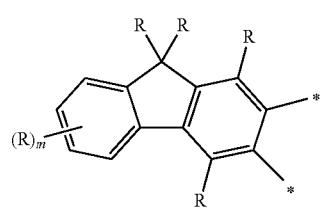

[Structural Formula 21]

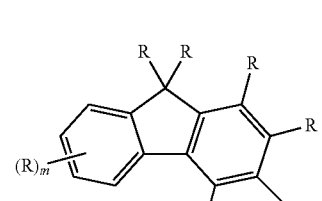

[Structural Formula 22]

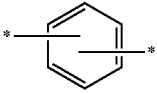

[Structural Formula 23]

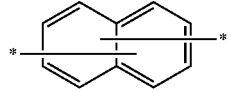

[Structural Formula 25]

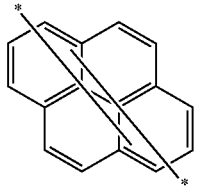

[Structural Formula 27]

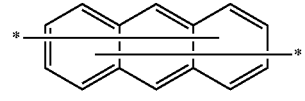

[Structural Formula 28]

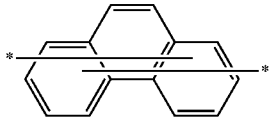

[Structural Formula 30]

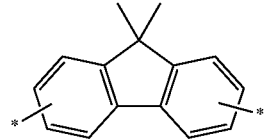

wherein

"-*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R's are the same or different, and are each independently any one selected from among hydrogen, deuterium, a cyano, a halogen, a nitro, an alkyl of 1 to 24 carbon atoms, an aryl of 6 to 24 carbon atoms, a heteroaryl of 2 to 24 carbon atoms, an alkylsilyl of 1 to 24 carbon atoms, an arylsilyl of 6 to 24 carbon atoms, m is an integer of 1 to 8, with a proviso that when m is 2 or greater or when two or more R's exist, the corresponding R's may be same or different.

4. The amine compound of claim 1, wherein linkers $L_1$ to $L_6$ of Chemical Formula B are each a single bond, or any one selected from the following [Structural Formula 22], [Structural Formula 23], [Structural Formula 25], [Structural Formula 27], [Structural Formula 28], and [Structural Formula 30], and p1, p2, r1, r2, s1, and s2 are each 1 or 2:

wherein each of the unsubstituted carbon atoms of the aromatic ring moiety is bound with a hydrogen atom or a deuterium atom.

5. The amine compound of claim 1, wherein the amine compound is selected from the group consisting of compounds represented by the following Chemical Formulas 16 to 23, 43, 49, 50, 55, 56, 60, 109 to 116, 118, 120, 122, 123, 160, 161, and 163 to 165:

<Chemical Formula 16>

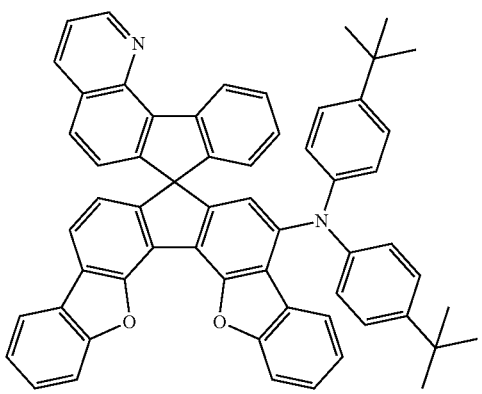

<Chemical Formula 17>
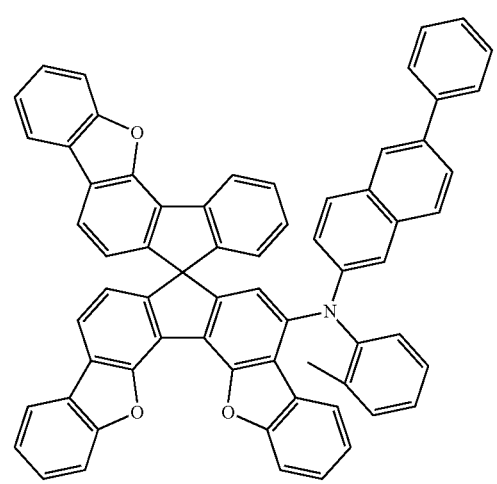
<Chemical Formula 18>
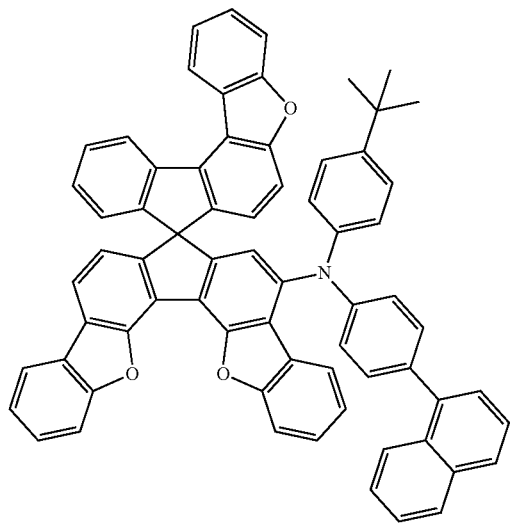
<Chemical Formula 19>
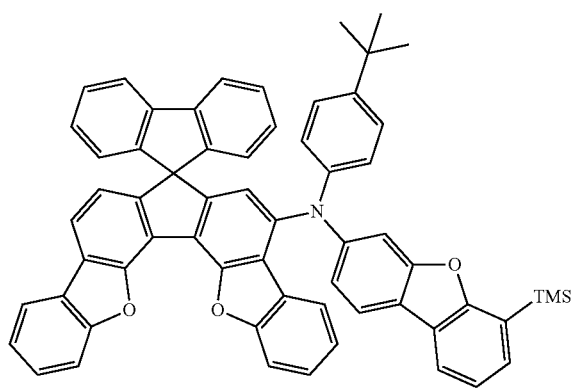
<Chemical Formula 20>
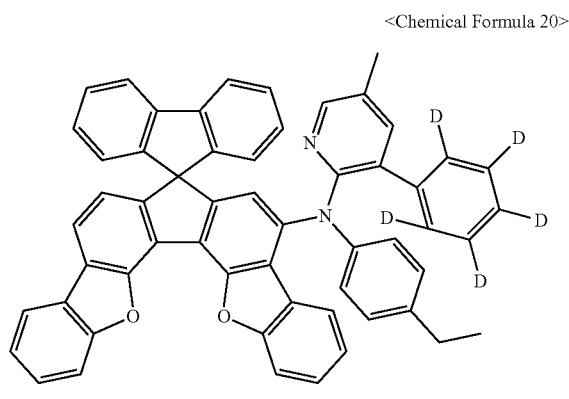
<Chemical Formula 21>
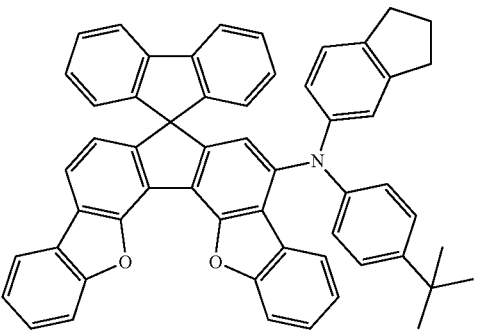
<Chemical Formula 22>
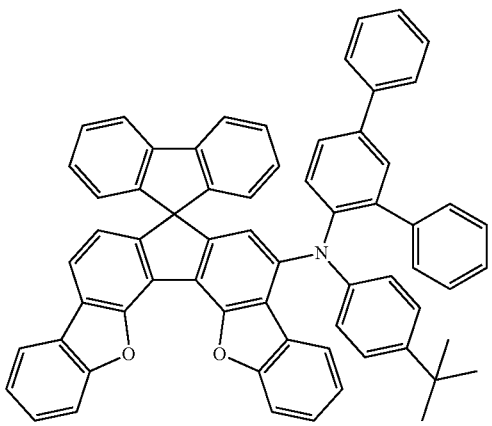
<Chemical Formula 23>
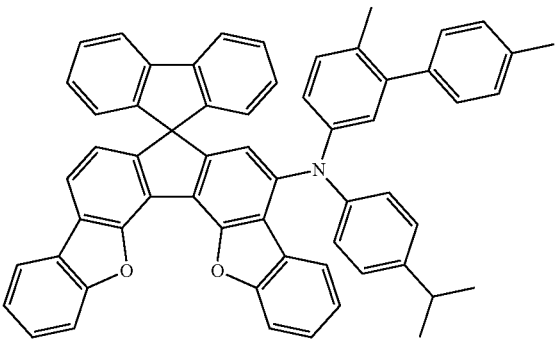

<Chemical Formula 43>
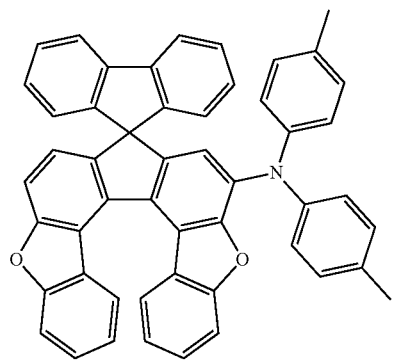
<Chemical Formula 49>
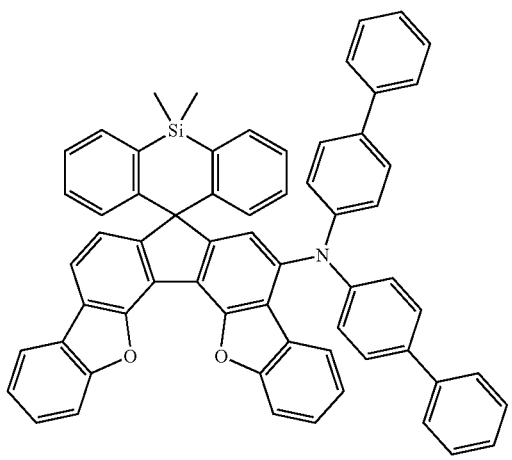
<Chemical Formula 50>
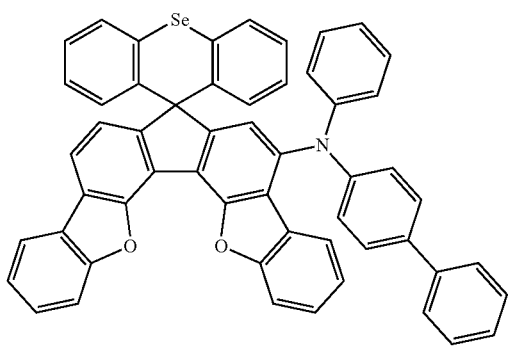
<Chemical Formula 55>
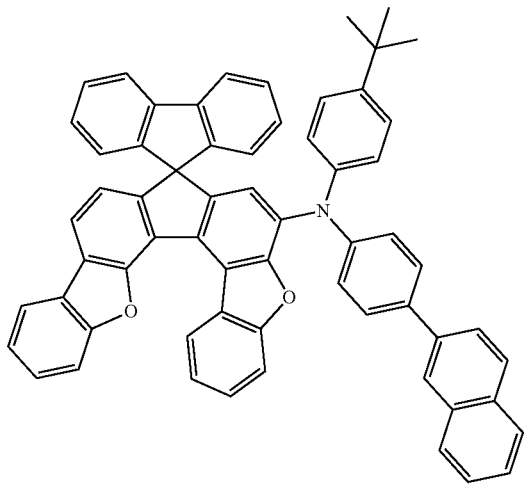
<Chemical Formula 56>
<Chemical Formula 60>
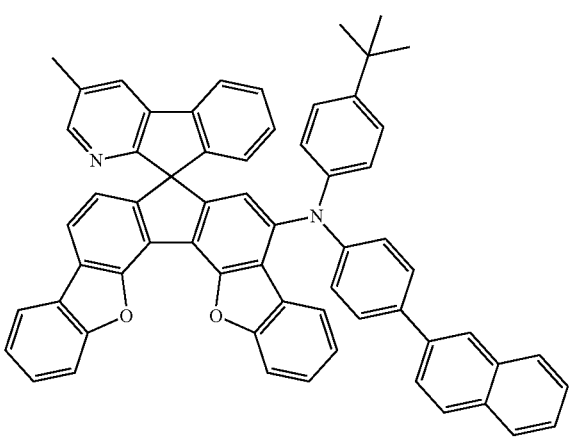

<Chemical Formula 109>
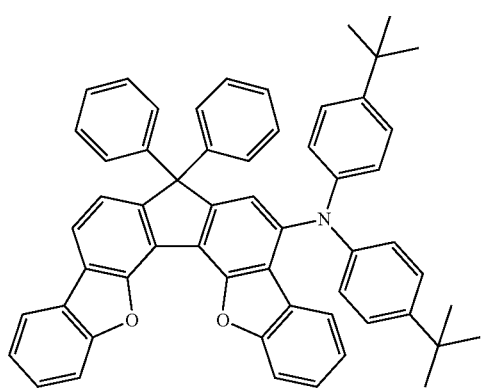
<Chemical Formula 110>
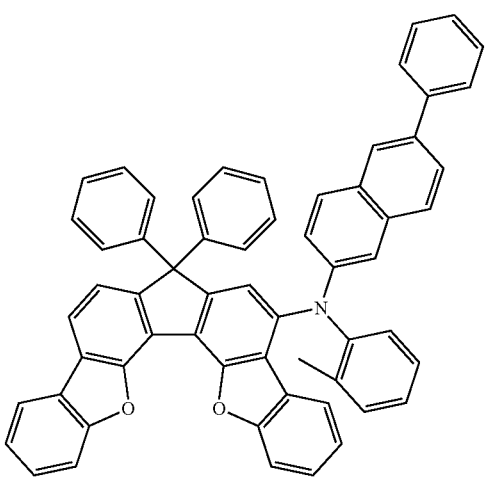
<Chemical Formula 111>
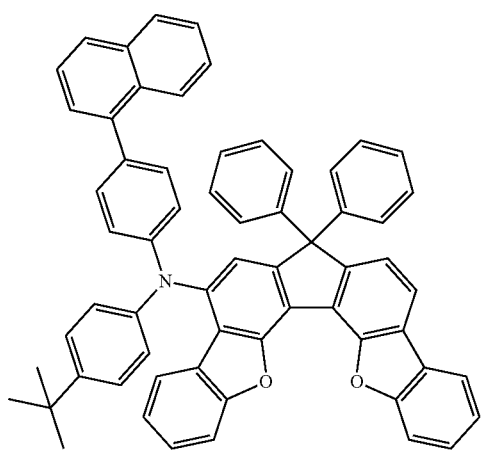
<Chemical Formula 112>
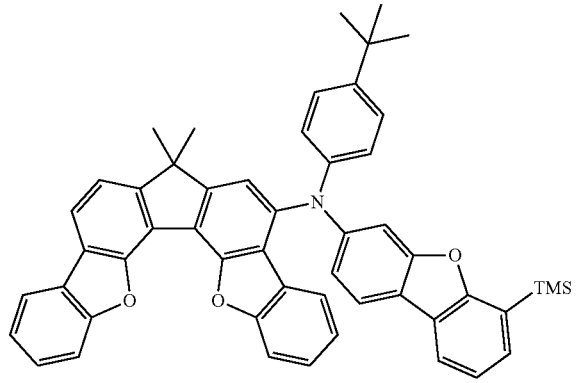
<Chemical Formula 113>
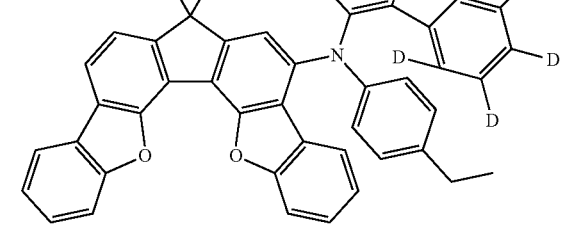
<Chemical Formula 114>
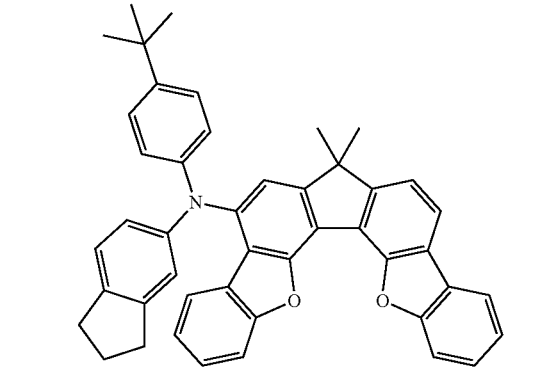
<Chemical Formula 115>
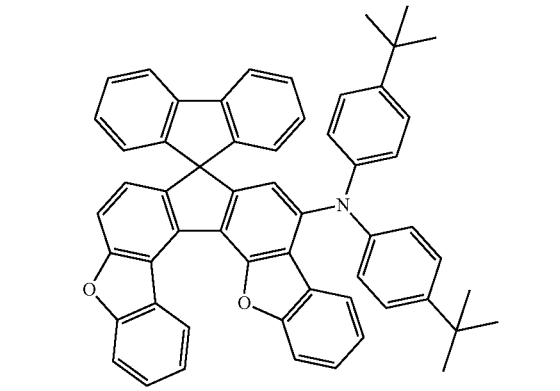

<Chemical Formula 116>
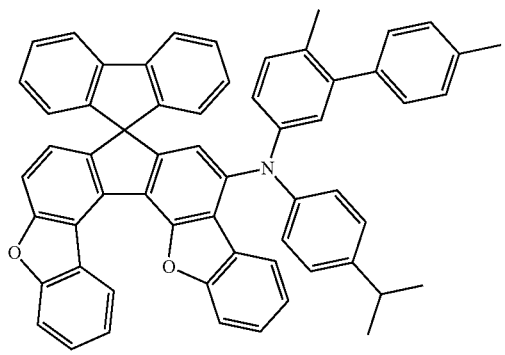
<Chemical Formula 118>
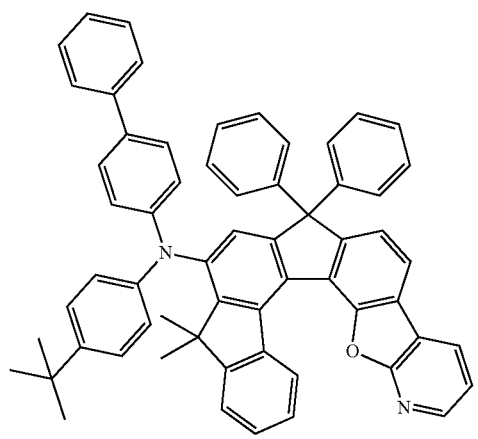
<Chemical Formula 120>
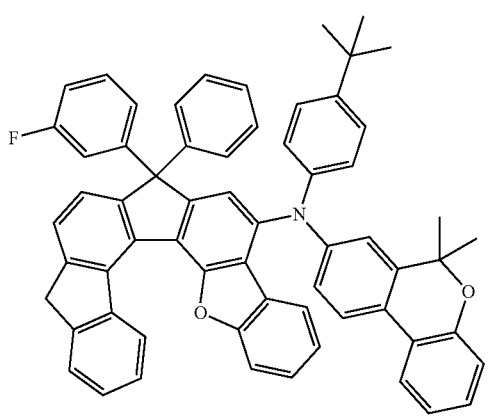
<Chemical Formula 122>
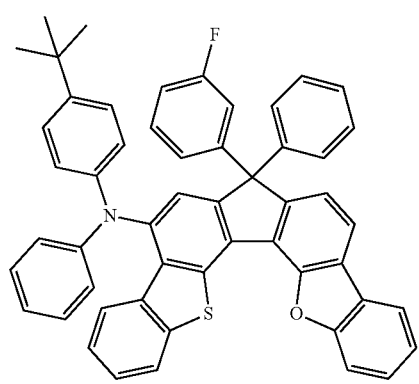
<Chemical Formula 123>
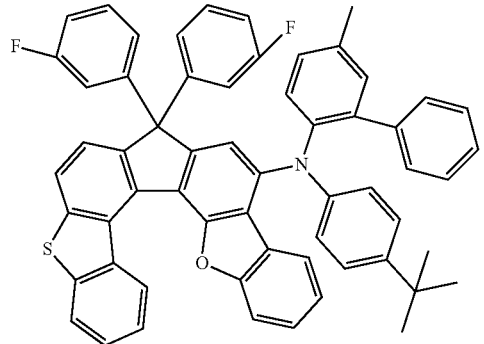
<Chemical Formula 160>
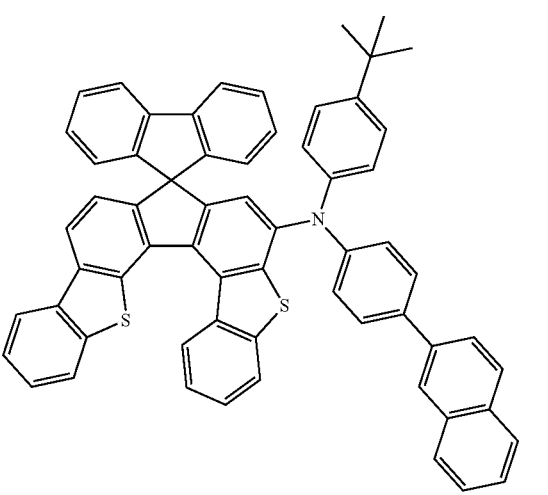
<Chemical Formula 161>
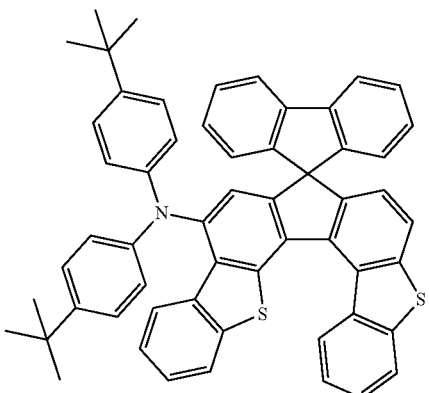
<Chemical Formula 163>
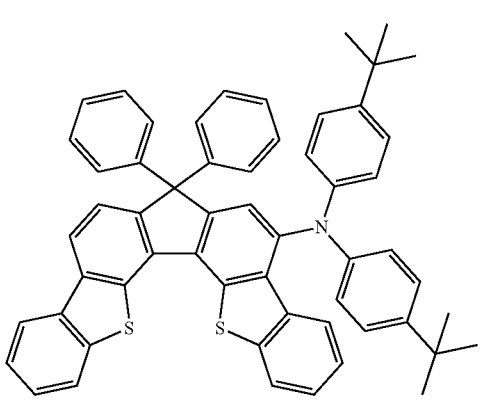

-continued

<Chemical Formula 164>

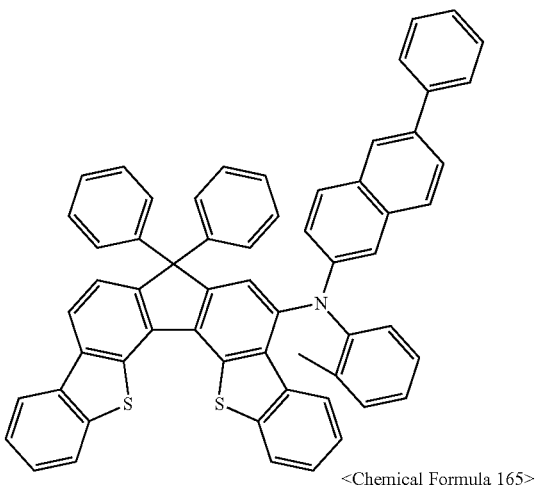

<Chemical Formula 165>

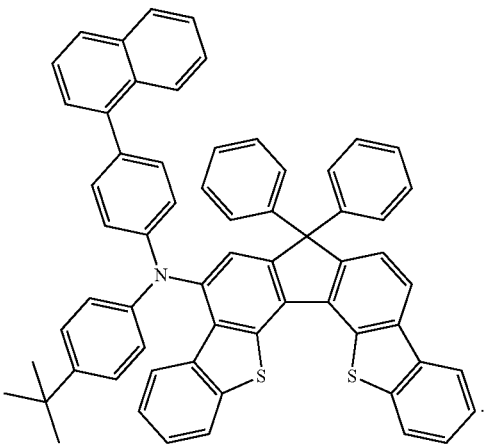

6. An organic light-emitting diode, comprising:
a first electrode;
a second electrode facing the first electrode; and
an organic layer interposed between the first electrode and the second electrode, wherein the organic layer comprises the amine compound of claim 1.

7. The organic light-emitting diode of claim 6, wherein the organic layer comprises at least one layer selected from among a hole injection layer, a hole transport layer, an electron-blocking layer, a light-emitting layer, an electron transport layer, and an electron injection layer.

8. The organic light-emitting diode of claim 7, wherein the organic layer interposed between the first electrode and the second electrode is a hole injection layer or a hole transport layer, and the amine compound is used in the hole injection layer or the hole transport layer.

9. The organic light-emitting diode of claim 7, wherein the at least one layer is formed using a deposition process or a solution process.

10. The organic light-emitting diode of claim 6, wherein the organic light-emitting diode is used for a device selected from among a flat display device, a flexible display device, a monochrome or white flat illumination device, and a monochrome or white flexible illumination device.

11. The organic light-emitting diode of claim 7, wherein the organic layer interposed between the first electrode and the second electrode is an electron-blocking layer, and the amine compound is used in the electron-blocking layer.

* * * * *